US007858091B2

(12) United States Patent
Yamano et al.

(10) Patent No.: US 7,858,091 B2
(45) Date of Patent: Dec. 28, 2010

(54) ANTIBODIES TO INSULIN-LIKE GROWTH FACTOR BINDING PROTEIN AND USES THEREOF

(75) Inventors: Kazuya Yamano, Machida (JP); Susumu Sekine, Machida (JP); Mitsuo Satoh, Machida (JP); Toshio Ota, Machida (JP); Akiko Furuya, Machida (JP); Kenji Shibata, Machida (JP); Yuki Kobayashi, Machida (JP); Miho Takebayashi, Machida (JP); Yusuke Nakamura, Yokohama (JP); Sumio Sugano, Suginami-ku (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

(21) Appl. No.: 12/013,293

(22) Filed: Jan. 11, 2008

(65) Prior Publication Data
US 2008/0241960 A1 Oct. 2, 2008

Related U.S. Application Data

(62) Division of application No. 11/396,430, filed on Mar. 30, 2006, now Pat. No. 7,332,301, which is a division of application No. 10/311,129, filed as application No. PCT/JP01/05112 on Jun. 15, 2001, now Pat. No. 7,071,160.

(30) Foreign Application Priority Data
Jun. 15, 2000 (JP) ............................. 2000-180214

(51) Int. Cl.
*A61K 39/395* (2006.01)
*C12N 5/12* (2006.01)
*G01N 33/53* (2006.01)

(52) U.S. Cl. .............. 424/145.1; 424/130.1; 435/70.21; 435/7.1

(58) Field of Classification Search ........................ None
See application file for complete search history.

(56) References Cited

U.S. PATENT DOCUMENTS 5,597,700 A * 1/1997 Konstantinov et al. ..... 435/7.92
6,391,588 B1 * 5/2002 Andress et al. ........... 435/69.4
2003/0148485 A1 8/2003 Taupier et al.

FOREIGN PATENT DOCUMENTS

WO WO 00/36105 A1 6/2000
WO WO 01/83705 A1 11/2001
WO WO 01/93983 A1 12/2001

OTHER PUBLICATIONS

Binkert et al., "Cloning, sequence analysis and expression of a cDNA encoding a novel insulin-like growth factor binding protein (IGFBP-2)" *The EMBO Journal*, 1989, pp. 2497-2502, vol. 8(9).

Burger et al., "Down Regulation of T1A12/mac25, a novel insulin-like growth factor binding protein related gene, is associated with disease progression in breast carcinomas", *Oncogene*, 1998, pp. 2459-2467, vol. 16.
Butkus et al., "Thromboxane Production And Platelet Aggregation In Diabetic Subjects With Clinical Complications", *Thrombosis Research*, 1980, pp. 211-223, vol. 19.
Clemmons, "IGF Binding Proteins and Their Functions", *Molecular Reproduction and Development*, 1993, pp. 368-375, vol. 35.
Damon et al., "Developmental Regulation of Mac25/Insulin-like Growth Factor-Binding Protein-7 Expression in Skeletal Myogenesis", *Experimental Cell Research*, 1997, pp. 192-195, vol. 237.
Degeorges et al., "Human Prostate Cancer Expresses the Low Affinity Insulin-like Growth Factor Binding Protein IGFBP-rP1", *Cancer Research*, 1999, pp. 2787-2790, vol. 59.
Dollery et al., "Circulating Prostacyclin May Be Reduced in Diabetes", *The Lancet*, 1979, p. 1365.
Halushka et al., "Increased platelet thromboxane synthesis in diabetes mellitus", *J. Lab. Clin. Med.*, 1981, 87-96, vol. 97(1).
Harrison et al., "Decreased Vascular Prostacyclin in Experimental Diabetes", *Life Sciences*, 1978, pp. 351-356, vol. 23.
Haugk et al., "Insulin-Like Growth Factor (IGF)-Binding Protein-Related Protein-1: An Autocrine/Paracrine Factor That Inhibits Skeletal Myoblast Differentiation but Permits Proliferation in Response to IGF", *Endocrinology*, 2000, pp. 100-110, vol. 141(1).
Hensby et al., "Prostacyclin Deficiency In Thrombotic Thrombocytopenic Purpura", *The Lancet*, 1979, p. 748.
How et al., Insulin-Like Growth Factor Binding Proteins (IGFBPs) and IGFBP-Related Protein 1-Levels in Cerebrospinal Fluid of Children with Acute Lymphoblastic Leukemia, *The Journal of Clinical Endocrinology & Metabolism*, 1999, pp. 1283-1287, vol. 84(4).
Hwa et al., "Characterization of Insulin-Like Growth Factor-Binding Protein Related Protein-1 in Prostate Cells", *Journal of Clinical Endocrinology and Metabolism*, 1998, pp. 4355-4361, vol. 83(12).
Hwa et al., "The Insulin-Like Growth Factor-Binding Protein (IGFBP) Superfamily", *Endocrine Review*, 1999, pp. 761-787, vol. 20(6).
Inoguchi et al., "Abnormality in Prostacyclin-Stimulatory Activity in Sera From Diabetics" *Metabolism*, 1989, pp. 837-842, vol. 38(9).
Inoguchi et al., "Reduced Serum-Stimulatory Activity on Prostacyclin Production by Cultured Aortic Endothelial Cells in Diabetes mellitus", *Haemostasis*, 1986, pp. 447-452, vol. 16.
Inoguchi et al., "Stimulatory activity on prostacyclin production decreases in sera from streptozotocin-induced diabetic rats", *Diabetes Research and Clinical Practice*, 1987, pp. 243-248, vol. 3.
Johnson et al., "Vascular Prostacyclin May Be Reduced In Diabetes In Man", *The Lancet*, 1979, pp. 325-326.

(Continued)

*Primary Examiner*—Christine J Saoud
(74) *Attorney, Agent, or Firm*—Townsend and Townsend and Crew LLP

(57) ABSTRACT

Using the proteins of the present invention, DNAs encoding the proteins, and antibodies recognizing the proteins, detection methods for diseases relating to the novel insulin-like growth factor binding proteins of the present invention, as well as diagnostic agents, preventive agents, and therapeutic agents for diseases relating to the proteins of the present invention can be provided.

9 Claims, 14 Drawing Sheets

OTHER PUBLICATIONS

Kiefer et al., "Molecular Cloning of a New Human Insulin-Like Growth Factor Binding Protein", *Biochemical and Biophysical Research Communications*, 1991, pp. 219-225, vol. 176(1).

Kiefer et al., "Identification and Molecular Cloning of Two New 30-kDa Insulin-like Growth Factor Binding Proteins Isolated from Adult Human Serum", *Journal of Biochemical Chemistry*, 1991, pp. 9043-9049, vol. 266(14).

Kim et al., "Identification of a family of low-affinity insulin-like growth factor binding proteins (IGFBPs): Characterization of connective tissue growth factor as a member of the IGFBP superfamily", 1997, pp. 12981-12986, vol. 94.

Komatsu et al., "Methylation and Downregulated Expression of mac25/Insulin-like Growth Factor Binding Protein-7 Is Associated with Liver Tumorigenesis in SV40T/t Antigen Transgenic Mice, Screened by Restriction Landmark Genomic Scanning for Methylation (RLGS-M)" *Biochemical and Biophysical Research Communications*, 2000, pp. 109-117, vol. 267.

Latour et al., "Inhibitory Insulin-Like Growth Factor-Binding Protein: Cloning, Complete Sequence, and Physiological Regulation", *Molecular Endocrinology*, 1990, pp. 1806-1814, vol. 4(12).

Lee, "Insulin-Like Growth Factor (IGF) Binding Protein Complementary Deoxyribonucleic Acid from Human HEP G2 Hepatoma Cells: Predicted Protein Sequence Suggests an IGF Binding Domain Different from Those of the IGF-1 and IGF-II Receptors", *Molecular Endocrinology*, 1998, pp. 404-411, vol. 2(5).

MacIntyre et al., "Localisation and stimulation of prostacyclin production in vascular cells", *Nature*, 1978, vol. 271.

Masakado et al., "Immunohistochemical Localization of a Novel Peptide, Prostacyclin-Stimulating Factor (PSF), in Human Tissues", *Thrombosis and Haemastasis*, 1995, pp. 1407-1410, vol. 74(6).

Mehls et al., "Therapeutic Value of Recombinant Human Growth Hormone in Children with Chronic Renal Failure", *Miner Electrolyte Metab.*, 1992, pp. 320-324, vol. 18.

Moncada, "Biological Importance of Prostacyclin", *Br. J. Pharmac.*, 1982, pp. 3-31, vol. 76.

Murphy, "Insulin-like growth factor-binding proteins: functional diversity or redundancy?", *Journal of Molecular Endocrinology*, 1998, pp. 97-107, vol. 21.

Murphy et al., "Identification and Characterization of Genes Differentially Expressed in Meningiomas", *Cell Growth and Differentiation*, 1993, pp. 715-722, vol. 4(9).

Ono et al., "Effect of high glucose concentrations on prostacyclin-stimulating factor mRNA expression in cultured aortic smooth muscle cells", *Diabetologica*, 1998, pp. 134-140, vol. 41.

Ono et al., "Reduced Expression of a Novel Peptide, Prostacyclin-Stimulating Factor, in the Kidneys of Streptozotocin-Induced Diabetic Rats", *J. Diab. Comp.*, pp. 252-258, vol. 12, 1998.

Pereira et al., "Cortisol Enhances the Expression of mac25/Insulin-Like Growth Factor-Binding Protein-Related Protein-1 in Cultured Osteoblasts", *Endocrinology*, 1999, pp. 228-232, vol. 140(1).

Pereira et al.., "Parathyroid Hormone Increases mac25/Insulin-Like Growth Factor-Binding Protein-Related Related Protein-1 Expression in Cultured Osteoblasts" *Endocrinology*, 1999, pp. 1998-2003, vol. 140(5).

Perks et al., "Insulin-Like Growth Factor Binding Proteins (IGFBPs) in Breast Cancer" *Journal of Mammary Gland Biology and Neoplasia*, 2000, pp. 75-84, vol. 5(1).

Rajaram et al., "Insulin-Like Growth Factor-Binding Proteins in Serum and Other Biological Fluids: Regulation and Functions", *Endocrine Reviews*, 1997, pp. 801-831, vol. 18(6).

Remuzzi et al., "Hæmolytic-Uræmic Syndrome: Deficiency of Plasma Factor(s) Regulating Prostacyclin Activity?", *The Lancet*, pp. 871-872, 1978.

Rutanen et al., "Insulin-Like Growth Factors and Their Binding Proteins in Benign and Malignant Uterine Diseases", *The British Library*, 1993, pp. 74-77, vol. 3.

Sekiguchi et al., "Immunohistochemical Study of Prostacyclin-Stimulating Factor (PSF) in the Diabetic and Atherosclerotic Human Coronary Artery", *Diabetes*, 1997, pp. 1627-1632, vol. 46.

Schneider et al., "Transgenic mouse models for studying the functions of insulin-like growth-factor binding proteins", *Faseb Journal*, 2000, pp. 629-640, vol. 14.

Shimasaki et al., "Identification and Molecular Characterization of Insulin-Like Growth Factor Binding Proteins (IBFBP-1,-2,-3,-4,-5 and -6", *Progress in Growth Factor Research*, 1991, pp. 243-266, vol. 3.

Shimasaki et al., "Identification of Five Different Insulin-like Growth Factor Binding Proteins (IGFBPs) from Adult Rat Serum and Molecular Cloning of a Novel IGFBP-5 in Rat and Human", *The Journal of Biological Chemistry*, 1991, pp. 10646-10653, vol. 266(16).

Silberbauer et al., "Decreased Vascular Prostacyclin in Juvenile-Onset Diabetes", *The New England Journal of Medicine*, 1979, pp. 366-367, vol. 300(7).

Sprenger et al., "Insulin-like Growth Factor Binding Protein-related Protein 1 (IGFBP-rP1) Is a Potential Tumor Suppressor Protein for Prostate Cancer", *Cancer Research*, 1999, pp. 2370-2375, vol. 59.

Swisshelm et al., "Enhanced expression of an insulin growth factor-like binding protein (mac25) in senescent human mammary epithelial cells and induced expression with retinoic acid", *Proc. Natl. Acad. Sci. USA*, 1995, pp. 4472-4476, vol. 92.

Taylor et al., "Humoral regulation of intestinal adaptation", *Baillière's Clinical Endocrinology and Metabolism*, 1994, pp. 165-183, vol. 8(1).

Umeda et al., "Prostacyclin-Stimulating Factor, Novel Protein, and Diabetic Angiopathy", *Diabetes*, 1996, pp. S111-S113, vol. 45(3).

Umeda et al., "Increased mRNA expression of a novel prostacyclin-stimulating factor in human colon cancer", *J Gastroenterol*, 1998, pp. 213-217, vol. 33.

Wetterau et al., "Novel Aspects of the Insulin-like Growth Factor Binding Proteins", *Molecular Genetics and Metabolism*. 1999, pp. 161-181, vol. 68.

Wood et al., "Cloning and Expression of the Growth Hormone-Dependent Insulin-Like Growth Factor-Binding Protein", *Molecular Endocrinology*, 1988, pp. 1176-1185.

Yamauchi et al., "Purification and molecular cloning of prostacyclin-stimulating factor from serum-free conditioned medium of human diploid fibroblast cells", *Biochem J.*, 1994, pp. 591-598, vol. 303.

EMBL Accession No. BC007758; *In:* Strausberg et al., "Generation and initial analysis of more than 15,000 full-length human and mouse cDNA sequences"; *Proc. Natl. Acad. Sci. U.S.A.*; 2002; pp. 16899-16903; vol. 99(26).

EMBL Accession No. AX358831;*In:* WO 01/93983; Baker et al., "Secreted and transmembrane polypeptides and nucleic acids encoding the same"; Dec. 13, 2001.

\* cited by examiner

FIG. 1

SIGNAL SEQUENCE

```
1  M------SEVPVAR-- ----VWLVLLLTVQ VGVTAGAP----------  27  :IGFBP1
1  MLPRVGCPALPLPPPP LLPLLPLLLLLLGAS ----GGGG----------  35  :IGFBP2
1  MQR--------ARPT LWAAALTLLVLLRG- -PPV-ARAGAS-------  30  :IGFBP3
1  MLP------------ L-CLVAALLL----A ------------AGPG   17  :IGFBP4
1  M-------------V LLTAV-LLLAAYAG -P---A----------    18  :IGFBP5
1  MIPH---------R LLPP--LLLLLALL- AAS--------------   20  :IGFBP6
1  MER----A--SLRAL LFGPAGLLLLLLPLS -----SSSSSDT-----  31  :IGFBP7
1  MLPPPR-PAAA---- LALPV-LLLLLWLT PPPTGARPSPGPDYLRRGW 43  :C-hsi13412
                                                          /C-kaia397
```

```
28  -------WQCAPCSAEKLALCPPVS-AS---------------CSEVTRS  54  :IGFBP1
36  GARAEVLFRCPPCTPERLAACGPPPVAPPAAVAAVAGGARMPCAELVRE  84  :IGFBP2
31  SGGLGPVVRCEPCDARALAQCAPP----------------PAVCAELVRE  64  :IGFBP3
18  PSLGDEAIHCPPCSEEKLARCRP-----------------PVGCEELVRE  50  :IGFBP4
19  -QSLGSFVHCEPCDEKALSMCPP-S---------------PLGC-ELVKE  50  :IGFBP5
21  --PGGALARCPGCGQGVQAGC------PGGCVEEDGGSP--------A  53  :IGFBP6
22  -------CGPCEPA--S-CPPLP----------------PLGCLLGETR  54  :IGFBP7
44  MRLLAEGEGCAPCRPE--E-CA----A---------------PRGCLAGRVR  73  :C-hsi13412
                                                           /C-kaia397
```

```
55  A GCGCCPMC ALPLGAACGV--ATAR---C   78  :IGFBP1
85  P GCGCCSVC ARLEGEACGV--YTPR---C  108  :IGFBP2
65  P GCGCCLTC ALSEGQPCGI--YTER---C   88  :IGFBP3
51  P GCGCCATC ALGLMPCGV--YTPR---C   74  :IGFBP4
51  P GCGCCMTC ALAEGQSCGV--YTER---C   74  :IGFBP5
54  E GCAEAEGC LRREGQECGV--YTPN---C   77  :IGFBP6
55  D ACGCCPMC ARGEGEPCGG--GGAGRGYC  81  :IGFBP7
74  D AGGCCWEC ANLEGQLCDL-DPSAHYCHC 101  :C-hsi13412    /C-kaia397
```

INSULIN-LIKE GROWTH FACTOR
BINDING MOTIF

+: With glucosidase
-: No glucosidase
n: Untreated by enzyme reaction

FIG. 11

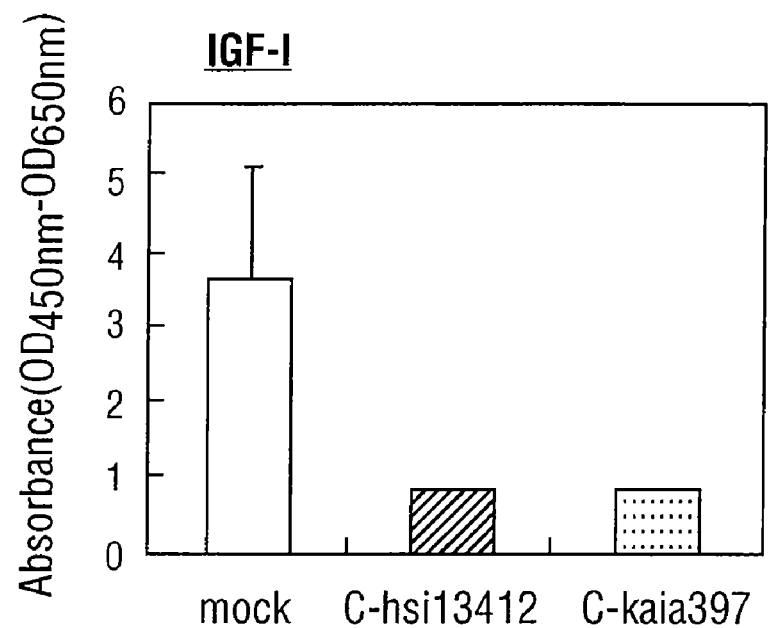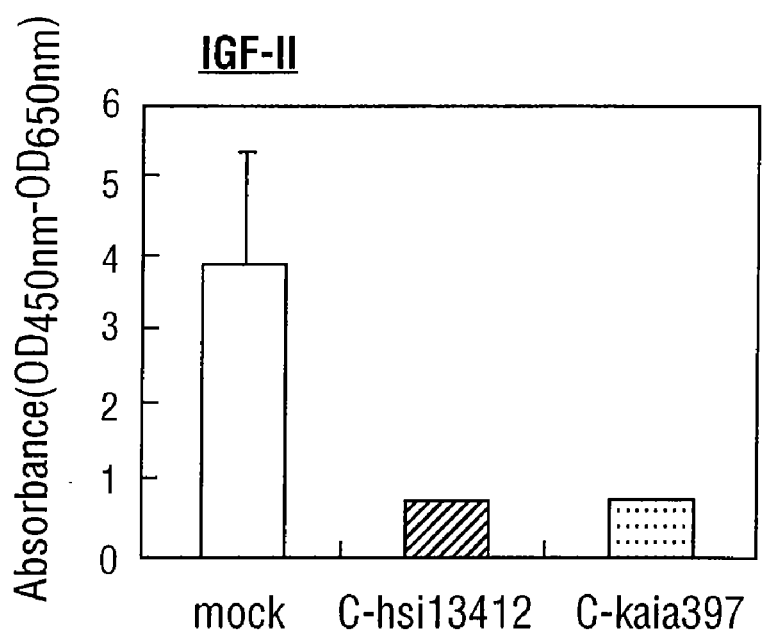
FIG. 13

//ANTIBODIES TO INSULIN-LIKE GROWTH FACTOR BINDING PROTEIN AND USES THEREOF

CROSS-REFERENCES TO RELATED APPLICATIONS

This application is a divisional of application Ser. No. 11/396,430, filed Mar. 30, 2006, which is a divisional of application Ser. No. 10/311,129, filed Apr. 9, 2003, which is the National Stage of International Application No. PCT/JP01/05112, filed Jun. 15, 2001 and claims priority to Japanese Patent Application Number 2000-180214, filed Jun. 15, 2000. Each of the aforementioned applications are hereby incorporated by reference in their entirety and for all purposes.

BACKGROUND OF THE INVENTION

1. Technical Field

The present invention relates to novel insulin-like growth factor binding proteins, DNAs encoding the proteins, and antibodies recognizing the proteins, as well as detection methods, diagnostic agents, and preventive agents or therapeutic agents for diseases associated with the proteins.

2. Background Art

Insulin-like growth factor binding proteins (hereinafter, referred to as "IGFBP") are a group of molecules that were discovered due to the fact that the insulin-like growth factor (hereinafter, referred to as "IGF") exists in the body fluid as a macromolecular complex. 10 types of these molecules, IGFBP-1 to 10, have been reported to exist until now, and are known to constitute a superfamily (Endocr. Rev., 18, 801 (1997); Prog. Growth Factor Res., 3, 243 (1991); Mol. Reprod. Dev., 35, 368 (1993); Proc. Natl. Acad. Sci. USA, 94, 12981 (1997)).

The existence of direct action by binding to integrin and the like has been also suggested as the function of IGFBP. However, the main action is predicted to be exhibited by the binding to IGF and insulin to regulate their activity, distribution, metabolism, and the like (Endocr. Rev., 18, 801 (1997); Bio Science Terminology Library Cytokines and Growth Factors, revised edition p 14-17 (1988)). Specifically, the IGFBP is expected to exhibit its function by suppressing the transport into blood, extravasation and degradation of IGF, by regulating receptor binding, and the like.

6 types of molecules, IGFBP-1 to 6, among the IGFBP superfamily have structural similarity and bind with higher affinity to IGF than to insulin. Therefore, they are classified into a subfamily as high-IGF-affinity IGFBPs (Mol. Endocrinol., 2, 404 (1988); EMBO J., 8, 2497 (1989); Mol. Endocrinol., 2, 1176 (1989); Mol. Endocrinol., 4, 1806 (1990); Biochem. Biophys. Res. Commun., 176, 219 (1991); J. Biol. Chem., 266, 9043 (1991); J. Biol. Chem., 266, 10646 (1991)).

In humans, the amino acid sequence homology among the molecules belonging to the high-IGF-affinity IGFBP subfamily is 49 to 60%. Furthermore, 18 cysteine residues are conserved in five of the IGFBPs, excluding IGFBP-6, and three of these residues to the N-terminal side form a homologous sequence represented by Gly-Cys-Gly-Cys-Cys-X-X-Cys (SEQ ID NO:26) (X represents an arbitrary amino acid; this homologous sequence is called insulin-like growth factor binding motif (hereinafter, referred to as "IGFBP motif")) and has been revealed to be involved in IGF binding (Prog. Growth Factor Res., 3, 243 (1991)).

IGFBP-1 and 3 are known to both suppress and enhance the action of IGF. Whereas IGFBP-2, 4, and 6 are inhibitory IGF binding proteins and IGFBP-5 as a promoting IGF binding protein. There are two types of IGFs, namely, (1) IGF-I: produced in a growth hormone dependent manner in liver, bone tissue, and the like, and functions as a growth factor that promotes physical growth; and (2) IGF-II: expressed in large amounts in central nervous system, bone tissue, and the like, and is presumed to play an important role in growth, mainly during the embryonal period. IGFBP-1, 3, and 4 indicate a binding activity similar toward IGF-1 and IGF-II, while IGFBP-2, 5, and 6 indicate a strong binding activity mainly toward IGF-II.

The tissue distribution of high-IGF-affinity IGFBP subfamily molecules differ depending on the molecules. IGFBP-1 is known to mainly exist in amniotic fluid and fetal serum; IGFBP-2 mainly in fetal liver and adult brain; IGFBP-3 mainly in liver and serum; IGFBP-4 mainly in renal glomeruli, skin, and intestinal epithelium; IGFBP-5 mainly in intestinal epithelium and bone; and IGFBP-6 mainly in skin and heart.

The following findings have been reported regarding the relationship between IGFBPs and pathology of diseases.

The fluctuations of IGF and IGFBP expressions are directly associated with the pathophysiology of dwarfism and acromegaly patients. On the other hand, although failure to thrive are often seen among patients of infantile chronic renal failure, their growth hormone and IGF expression levels are normal, and most of the cause is the functional disorder of IGF due to the increase of IGFBP-2 and/or IGFBP-3 (Miner. Electrolyte Mrtab., 18, 320 (1992)). IGFBP-4 and 5 have important functions in bone metabolism. It has been reported that the expression level of IGFBP-5 decreases in osteoporosis, and the expression of IGFBP-4 elevates in women fracture patients of old age accompanied with the elevation of parathyroid hormone. Furthermore, although enhancement of paracrine effect of IGF-1 is observed in compensatory hypertrophy after nephrectomy and small intestine resection, the mRNA level of IGF-1 is invariant, and free IGF-I increases due to diminished IGFBP-3 expression (J. Fuller, Baillieres Clin. Endocrinol. Metab., 8, 165 (1994)). Moreover, the expression of IGFBP-1 is decreased in malignant tumors of endometrium, compared to benign tumors (Growth Regul., 3, 74, (1993)).

On the other hand, four molecules in the IGFBP superfamily, IGFBP-7 to 10, are structurally similar and are considered to share a common characteristic of having a low affinity to IGFs. Therefore, they are classified into a separate subfamily as low-IGF-affinity IGFBPs (Proc. Natl. Acad. Sci. USA, 94, 12981 (1997); Cancer Res., 59, 2787 (1999)).

Regarding IGFBP-7, various physiological activities have been reported. Particularly, many reports have been made on the relationship with cancer and its pathology.

While the expression of IGFBP-7 is elevated in aged human epithelial cells (J. Clin. Endocrinol. Metab., 4, 715 (1993)), its expression is diminished in carcinoma cell lines. Therefore, IGFBP-7 is thought to function as a gene involved in cancer suppression activity (Proc. Natl. Acad. Sci. USA, 92, 4472 (1995)). The gene locus of IGFBP-7 on the human chromosome is 4q12, and its expression is known to enhance by the treatment of human epithelial cells with retinoic acid (Proc. Natl. Acad. Sci. USA, 92, 4472 (1995)).

In breast cancer tissues, LOH (loss of heterozygosity) at chromosome 4q12 to 13 was observed at a frequency of approximately 50%, and the expression of IGFBP-7 has been confirmed to be decreased (Oncogene, 16, 2459 (1998)). The IGFBP-7 expression is also decreased at the mRNA level in prostate cancer tissues, and no expression is detected particularly in cell lines derived from malignant prostate cancer (J. Clin. Endocrinol. Metab., 83, 4355 (1998)).

Moreover, when IGFBP-7 is forcedly expressed in prostate cancer cell line in which IGFBP-7 expression is decreased, extension of cell division time, decrease of colony forming ability in soft agar medium, decrease of tumor forming ability in nude mouse transplantation, and elevation of apoptosis induction rate by drug treatment have been observed, which suggests a relationship between the IGFBP-7 expression and degree of malignancy of prostate cancer (Cancer Res., 59, 2370 (1999)).

Concentrations of IGFBP-7 and IGFBP-3 in the cerebrospinal fluid have been reported to rise in leukemia patients, and their relationship to the pathology of leukemia is receiving attention (J. Clin. Endocrinol. Metab., 84, 1283 (1999)).

Due to the enhanced expression of IGFBP-7 in large intestinal cancer tissues and cell lines, the relationship of IGFBP-7 with the pathology of colon cancer is receiving attention (J. Gastroenterology, 33, 213 (1998)).

IGFBP-7 expression is decreased in large uterine leiomyoma sites, and the expression of IGFBP-7 is reported to be elevated in patients who have received gonadotropin-releasing hormone therapy (J. Reprod. Immunol., 43, 53 (2000)).

The 5' upstream region of IGFBP-7 gene is methylated and its expression level is decreased in mouse liver cancer cells that have been induced with SV40T antigen. Therefore, a mechanism involving methylation of the gene has been proposed for the regulation of the IGFBP-7 expression associated with canceration (Biochem. Biophys. Res. Commun., 267, 109 (2000)).

The relation between IGFBP-7 and diabetes has also been reported.

A factor (PGI2-stimulating factor, hereinafter, referred to as "PSF") promoting the production of prostacyclin PGI2 by acting on vascular endothelial cells was shown to be identical to IGFBP-7 (Biochem. J., 303, 591, (1994)). The expression of this factor, which is expressed in vascular endothelial cells and smooth muscle cells (Thromb Haemost., 74, 1407 (1995)), is reported to be decreased in kidneys and angiopathy sites of a type I diabetes model established by streptozotocin administration (Diabetes, 45, S111 (1996); J. Diabetes & its Complications, 12, 252 (1998)). Furthermore, decreased expression of IGFBP-7 at the protein level has also been observed in coronary artery smooth muscle cells of type II diabetes patient (Diabetes, 46, 1627 (1997)). Moreover, the expression level of IGFBP-7 has been confirmed to decrease at the mRNA and protein levels by culturing smooth muscle cells derived from bovine arteries in high-glucose medium (Diabetes, 46, 1627 (1997); Diabetologia, 41, 134 (1998)).

The expression of IGFBP-7 in osteoblasts rises by TGF-β (transforming growth factor-β), parathyroid hormone (PTH), and prostaglandin E2 (PGE2). Therefore, IGFBP-7 appears to have physiological effect on osteoblasts (Endocrinology, 140, 1998 (1999)). Furthermore, treatment of osteoblasts with glucocorticoids is reported to suppress the expression of IGF-I, while enhancing the expression of IGFBP-7 (Endocrinology, 140, 228 (1999)).

Furthermore, IGFBP-7 is indicated to have an effect on the differentiation into skeletal muscles by suppressing the differentiation-promoting action of IGF (Exp. Cell Res., 237, 192 (1997); Endocrinology, 141, 100 (2000)).

Since IGFBP-7 was the same molecule as the factor PSF that promotes prostacyclin PGI2 production, a part of the physiological function of IGFBP-7 is considered to perform as the effector molecule for PGI2.

PGI2, a type of prostaglandin, has strong platelet aggregation inhibitory effect and vasorelaxing effect, and is known to function antagonistically with TXA2 that has the opposite effect to maintain the homeostasis within a living body (Br. J. Pharmac., 76, 3 (1982)). Imbalance in TXA2 and PGI2 production, especially decrease in PGI2 production causes development of angiopathy in thrombosis and arteriosclerosis (Br. J. Pharmac., 76, 3 (1982)). Regarding the development and progression of diabetic angiopathy, in addition to the enhancement of platelet-derived TXA2 production (Thromb. Res., 19, 211 (1980); J. Lab. Clin. Med., 97, 87 (1981)), decrease of blood vessel-derived PGI2 production has been confirmed to enhance platelet aggregation in diabetes patients and in laboratory animals with diabetes (Lancet, 1, 325 (1979); Lancet, 2, 1365 (1979); N. Engl. J. Med., 300, 366 (1979); Life Sci., 23, 351 (1978)).

Furthermore, PSF is a factor that exists in the blood stream and is reported to stimulate the production of PGI2 in vascular wall (Nature, 271, 549 (1978)). Moreover, the level of this factor in blood is reported to be decreased in hemolytic uremic syndrome (Lancet, 2, 871 (1978)), thrombotic thrombocytopenic purpa (Lancet, 2, 748 (1979)), sickle cell anemia (Br. J. Haematol., 48, 545 (1981)), acute myocardial infarction (Coronary, 2, 49 (1985)), diabetic angiopathy (Metabolism, 38, 837 (1989); Haemostasis, 16, 447 (1986); Diab. Res. Clin. Pract., 3, 243 (1987)), and arteriosclerotic diseases.

More specifically, IGFBP-7 has been demonstrated to exert platelet aggregation inhibitory effect, smooth muscle relaxation effect, and gastric acid secretion inhibitory effect by elevating the PGI2 concentration in blood via the promotion of PGI2 production of vascular endothelial cells.

As mentioned above, factors belonging to the IGFBP superfamily have been revealed to be involved in various biological phenomena including regulation of IGF and insulin function, pregnancy, compensatory effect in exhaustive diseases, bone metabolism, differentiation of skeletal muscle cells, promotion of PGI2 production in vascular endothelial cells, PGI2-mediated inhibition of platelet aggregation, vascular smooth muscle relaxation, bronchial smooth muscle relaxation, and inhibition of gastric acid secretion. Furthermore, they are shown to be associated with diseases, such as dwarfism, acromegaly, infantile chronic renal failure, osteoporosis, breast cancer, prostate cancer, acute leukemia, large intestine cancer, uterine leiomyoma, liver cancer, type I diabetes, type II diabetes, thrombosis, arteriosclerosis, hemolytic uremic syndrome, thrombotic thrombocytopenic purpa, sickle cell anemia, acute myocardial infarction, and diabetic angiopathy.

Therefore, proteins having the activity of IGFBP that belong to the IGFBP superfamily, genes encoding the proteins, antisense DNAs, and antibodies recognizing the proteins are considered to serve as medicaments for detecting, treating, or preventing diseases accompanying abnormal cell growth, diseases accompanying angiopathy, diseases accompanying abnormal bone metabolism, diseases accompanying disorders of IGF and growth hormone action, diseases accompanying abnormal differentiation or growth of smooth muscle cells, diseases accompanying abnormal differentiation or growth of skeletal muscle cells, diseases accompanying abnormal gastric acid secretion, or inflammatory diseases accompanying abnormal lymphocyte invasion. Thus, great attention, as useful targets for development of new drugs, has been paid on factors belonging to the IGFBP superfamily.

Furthermore, the possibility on the existence of novel factors belonging to the IGFBP superfamily was indicated. By obtaining a novel IGFBP gene, the function of this IGFBP can be estimated by comparing the amino acid sequence of the novel IGFBP with that of known IGFBPs, or by studying the expression distribution of transcription products of the IGFBP gene, to finally provide useful information for drug development. In addition, when a novel IGFBP gene is obtained, substances that suppress the expression or function of the IGFBP can be screened. Compounds obtained by this screening procedure are expected to serve as useful drugs.

BRIEF SUMMARY OF THE INVENTION

Disclosure of the Invention

The present invention provides novel insulin-like growth factor binding proteins, DNAs encoding the proteins, and antibodies recognizing the proteins, as well as detection methods, diagnostic agents, preventive agents, and therapeutic agents for diseases associated with the proteins.

Upon extensive analysis to solve the above-mentioned objective, the present inventors succeeded in obtaining novel insulin-like growth factor binding proteins belonging to the IGFBP family and DNAs encoding the proteins, and accomplished the present invention.

More specifically, the present invention provides the following (1) to (60).

(1) An insulin-like growth factor binding protein, which comprises the amino acid sequence represented by SEQ ID NO: 1.

(2) An insulin-like growth factor binding protein, which comprises the amino acid sequence represented by SEQ ID NO: 2.

(3) A protein selected from the group of:
(A) a protein comprising an amino acid sequence, wherein one or more amino acids have been deleted, substituted, or added in the amino acid sequence represented by SEQ ID NO: 1, which protein substantially has an identical activity to the protein according to (1); and
(B) a protein comprising an amino acid sequence, wherein one or more amino acids have been deleted, substituted, or added in the amino acid sequence represented by SEQ ID NO: 2, which protein substantially has an identical activity to the protein according to (2).

(4) A protein selected from the group of:
(A) a protein comprising an amino acid sequence with 60% or higher identity with the amino acid sequence represented by SEQ ID NO: 1, wherein the protein substantially has an identical activity to the protein according to (1); and
(B) a protein comprising an amino acid sequence with 60% or higher identity with the amino acid sequence represented by SEQ ID NO: 2, wherein the protein substantially has an identical activity to the protein according to (2).

(5) A protein selected from the group of:
(A) a protein comprising an amino acid sequence that includes the 75th to the 82nd amino acid residues of the amino acid sequence represented by SEQ ID NO: 1, wherein the protein substantially has an identical activity to the protein of (1); and
(B) a protein comprising an amino acid sequence that includes the 75th to the 82nd amino acid residues of the amino acid sequence represented by SEQ ID NO: 2, wherein the protein substantially has an identical activity to the protein of (2).

(6) A protein selected from the group of:
(A) a protein comprising an amino acid sequence wherein one or more amino acids are deleted, substituted, or added in the amino acid sequence according to (A) of (5), which protein substantially has an identical activity to the protein according to (1); and
(B) a protein comprising an amino acid sequence wherein one or more amino acids are deleted, substituted, or added in the amino acid sequence according to (B) of (5), which protein substantially has an identical activity to the protein according to (2).

(7) A protein selected from the group of:
(A) a protein comprising an amino acid sequence with 60% or higher identity with the amino acid sequence according to (A) of (5), which protein substantially has an identical activity to the protein of (1); and
(B) a protein comprising an amino acid sequence with 60% or higher identity with the amino acid sequence according to (B) of (5), which protein substantially has an identical activity to the protein of (2).

(8) A protein selected from the group of:
(A) the protein according to (A) of (5) comprising a partial amino acid sequence that includes the 171st to the 304th amino acid residues in the amino acid sequence represented by SEQ ID NO: 1, which protein substantially has an identical activity to the protein according to (1); and
(B) the protein according to (B) of (5) comprising a partial amino acid sequence that includes the 171st to the 197th amino acid residues in the amino acid sequence represented by SEQ ID NO: 2, which protein substantially has an identical activity to the protein according to (2).

(9) A protein selected from the group of:
(A) a protein comprising an amino acid sequence wherein one or more amino acids are deleted, substituted, or added in the amino acid sequence according to (A) of (8), which protein substantially has an identical activity to the protein according to (1); and
(B) a protein comprising an amino acid sequence wherein one or more amino acids are deleted, substituted, or added in the amino acid sequence according to (B) of (8), which protein substantially has an identical activity to the protein according to (2).

(10) A protein selected from the group consisting of:
(A) a protein comprising an amino acid sequence with 60% or higher identity with the amino acid sequence according to (A) of (8), which protein substantially has an identical activity to the protein according to (1); and
(B) a protein comprising an amino acid sequence with 60% or higher identity with the amino acid sequence according to (B) of (8), which protein substantially has an identical activity to the protein according to (2).

(11) A polypeptide selected from the group of:
(A) a polypeptide comprising an amino acid sequence that includes at least 5 or more continuous amino acids in the amino acid sequence represented by SEQ ID NO: 1; and
(B) a polypeptide comprising an amino acid sequence that includes at least 5 or more continuous amino acids in the amino acid sequence represented by SEQ ID NO: 2.

(12) A polypeptide selected from the group of:
(A) a polypeptide comprising an amino acid sequence that includes at least 5 or more continuous amino acids of the 171st to the 304th amino acid residues in the amino acid sequence represented by SEQ ID NO: 1; and
(B) a polypeptide comprising an amino acid sequence that includes at least 5 or more continuous amino acids of the 171st to the 197th amino acid residues in the amino acid sequence represented by SEQ ID NO: 2.

(13) A DNA encoding the protein or the polypeptide according to any one of (1) to (12).

(14) A DNA containing the coding region of the nucleotide sequence represented by SEQ ID NO: 3.

(15) A DNA containing the coding region of the nucleotide sequence represented by SEQ ID NO: 4.

(16) A DNA selected from the group of:
 (A) a DNA that hybridizes under stringent conditions to the DNA encoding the protein according to (1), the DNA encoding the protein or the polypeptide of (A) according to any one of (3) to (12), or the DNA comprising the coding region of the nucleotide sequence represented by SEQ ID NO: 3, wherein the DNA encodes a protein that substantially has an identical activity to the protein according to (1); and
 (B) a DNA that hybridizes under stringent conditions to the DNA encoding the protein according to (2), the DNA encoding the protein or the polypeptide of (B) according to any one of (3) to (12), or the DNA comprising the coding region of the nucleotide sequence represented by SEQ ID NO: 4, wherein the DNA encodes a protein that substantially has an identical activity to the protein according to (2).

(17) A recombinant DNA obtained by ligating the DNA according to any one of (13) to (16) with a vector.

(18) A transformant obtained by introducing the recombinant DNA according to (13) into a host cell.

(19) The transformant according to (18), wherein the host cell is a cell selected from the group consisting of bacteria, yeast, insect cell, plant cell, and animal cell.

(20) A transformant FERM BP-7181 containing the DNA according to (14).

(21) A transformant FERM BP-7180 containing the DNA according to (15).

(22) A process for producing the protein or the polypeptide according to any one of (1) to (12), which comprises the steps of: culturing a transformant according to any one of (18) to (21) in a media so as to produce and accumulate the protein or the polypeptide according to any one of (1) to (12) in a culture; and recovering the protein or the polypeptide from the culture.

(23) An antibody recognizing the protein according to any one of (1) to (10).

(24) An antibody recognizing the protein according to any one of (1) or (A) of (3) to (10), but which does not recognize the protein according to any one of (2) or (B) of (3) to (10).

(25) An antibody recognizing the protein according to any one of (2) or (B) of (3) to (10), but which does not recognize the protein according to any one of (1) or (A) of (3) to (10).

(26) A method for producing an antibody recognizing the protein according to any one of (1) or (A) of (3) to (10), wherein the polypeptide according to (A) of (11) or (A) of (12) is used as the antigen.

(27) A method for producing an antibody recognizing the protein according to any one of (2) or (B) of (3) to (10), wherein the polypeptide according to (B) of (11) or (B) of (12) is used as the antigen.

(28) An antibody obtained by the method according to (26), wherein the antibody specifically recognizes the protein according to any one of (1) or (A) of (3) to (10).

(29) An antibody obtained by the method according to (27), wherein the antibody specifically recognizes the protein according to any one of (2) or (B) of (3) to (10).

(30) A monoclonal antibody produced by a hybridoma with the accession number FERM BP-7603.

(31) A monoclonal antibody produced by a hybridoma with the accession number FERM BP-7604.

(32) A method for immunologically detecting or quantifying the protein according to any one of (1) to (10), wherein the antibody according to any one of (23) to (25) or (28) to (31) is used.

(33) An oligonucleotide having a sequence comprising 5 to 60 continuous nucleotides of the nucleotide sequence of the DNA according to any one of (13) to (16), an oligonucleotide having a sequence complementary to said oligonucleotide, or derivatives thereof.

(34) A method for detecting or quantifying the expression of a gene encoding the protein according to any one of (1) to (10), wherein hybridization is conducted using the DNA according to any one of (13) to (16), or the oligonucleotide or the oligonucleotide derivatives according to (33) as a probe.

(35) A method for detecting or quantifying the expression of a gene encoding the protein according to any one of (1) to (10), wherein polymerase chain reaction is conducted using the oligonucleotide or the oligonucleotide derivative according to (33) as a primer.

(36) A method for detecting the mutation of a gene encoding the protein according to any one of (1) to (10), wherein the hybridization is conducted using the DNA according to any one of (13) to (16), or the oligonucleotide or the oligonucleotide derivative according to (33).

(37) A method for detecting the mutation of a gene encoding the protein according to any one of (1) to (10), wherein polymerase chain reaction is conducted using the oligonucleotide or the oligonucleotide derivative according to (33).

(38) A method for detecting a disease selected from the group of:
 (A) a method for detecting a disease, wherein the mutation is detected or the expression level is measured for the DNA encoding the protein according to any one of (1) to (10), and then compared with that of a healthy individual; and
 (B) a method for detecting a disease, wherein the mutation is detected or the expression level is measured for the protein according to any one of (1) to (10), and then compared with that of a healthy individual.

(39) A method for detecting a disease selected from the group of:
 (A) a method for detecting a disease, wherein the mutation or expression level of the DNA encoding the protein according to any one of (1) or (A) of (3) to (10) is compared with that of the DNA encoding the protein according to any one of (2) or (B) of (3) to (10); and
 (B) a method for detecting a disease, wherein the mutation or expression level of the protein according to any one of (1) or (A) of (3) to (10) is compared with that of the protein according to any one of (2) or (B) of (3) to (10).

(40) The detection method according to (38) or (39), wherein the disease is selected from the group consisting of: diseases accompanying abnormal cell growth, diseases accompanying angiopathy, diseases accompanying abnormal bone metabolism, diseases accompanying disorders of insulin-like growth factors or growth hormone action, diseases accompanying abnormal differentiation or growth of smooth muscle cells, diseases accompanying abnormal differentiation or growth of skeletal muscle cells, diseases accompanying abnormal gastric acid secretion, and inflammatory diseases accompanying abnormal lymphocyte invasion.

(41) The detection method according to (40), wherein the disease accompanying abnormal cell growth is selected from the group consisting of: acute myelogenous leukemia, breast cancer, prostate cancer, colon cancer, hepatic cancer, myeloma, uterine leiomyoma, malignant tumor, and solid tumor; the disease accompanying angiopathy is selected from the group consisting of: myocardial infarction, cerebral infarction, peripheral vascular atresia, angina pectoris, hypertension, hyperlipidemia, diabetes, diabetic retinopathy, glomerulonephritis, arteriosclerosis, thrombosis, hemolytic uremic syndrome, thrombotic thrombocytopenic purpa, ischemic heart disease, ischemic encephalopathy, heart failure, hemostasis, and choroid circulatory dysfunction; the disease accompanying abnormal bone metabolism is osteoporosis; the disease accompanying disorders of insulin-like growth factors or growth hormone action is selected from the group consisting of dwarfism, acromegaly, and infantile chronic renal failure; the disease accompanying abnormal differentiation or growth of smooth muscle cells is selected from the group consisting of: arteriosclerosis, bronchial disease, and restenosis; the disease accompanying abnormal differentiation or growth of skeletal muscle cells is myasthenia gravis; the disease accompanying abnormal gastric acid secretion is gastric ulcer; and the inflammatory disease accompanying abnormal lymphocyte invasion is selected from the group consisting of: microbial infection, chronic hepatitis B, chronic rheumatoid arthritis, sepsis, graft versus host disease, insulin dependent diabetes mellitus, nephritis, traumatic brain damage, inflammatory enteropathy, allergy, atopy, asthma, pollinosis, airway hypersensitivity, and autoimmune disease.

(42) The detection method according to any one of (38) to (41), wherein the detection method is conducted by the method selected from the group of:
 (A) the detection method of (36) or (37); and
 (B) the detection or quantification method of (32), (34), or (35).

(43) A medicament containing the protein or the polypeptide according to any one of (1) to (12).

(44) A medicament, which contains the DNA according to any one of (13) to (16), or the oligonucleotide or the oligonucleotide derivative according to (33).

(45) The medicament according to (44), wherein the medicament is a vector for genetic prevention or a vector for gene therapy.

(46) A medicament containing the antibody according to any one of (23) to (25) and (28) to (31).

(47) The medicament according to any one of (43) to (46), wherein the medicament is a diagnostic agent, a preventive agent, or a therapeutic agents for diseases accompanying abnormal cell growth, diseases accompanying angiopathy, diseases accompanying abnormal bone metabolism, diseases accompanying disorders of insulin-like growth factors or growth hormone action, diseases accompanying abnormal differentiation or growth of smooth muscle cells, diseases accompanying abnormal differentiation or growth of skeletal muscle cells, diseases accompanying abnormal gastric acid secretion, or inflammatory diseases accompanying abnormal lymphocyte invasion.

(48) The medicament according to (47), wherein the disease accompanying abnormal cell growth is acute myelogenous leukemia, breast cancer, prostate cancer, colon cancer, hepatic cancer, myeloma, uterine leiomyoma, malignant tumor, or solid tumor; the disease accompanying angiopathy is myocardial infarction, cerebral infarction, peripheral vascular atresia, angina pectoris, hypertension, hyperlipidemia, diabetes, diabetic retinopathy, glomerulonephritis, arteriosclerosis, thrombosis, hemolytic uremic syndrome, thrombotic thrombocytopenic purpa, ischemic heart disease, ischemic encephalopathy, heart failure, hemostasis, or choroid circulatory dysfunction; the disease accompanying abnormal bone metabolism is osteoporosis; the disease accompanying disorders of insulin-like growth factors or growth hormone action is dwarfism, acromegaly, or infantile chronic renal failure; the disease accompanying abnormal differentiation or growth of smooth muscle cells is arteriosclerosis, bronchial disease, or restenosis; the disease accompanying abnormal differentiation or growth of skeletal muscle cells is myasthenia gravis; the disease accompanying abnormal gastric acid secretion is gastric ulcer; and the inflammatory disease accompanying abnormal lymphocyte invasion is microbial infection, chronic hepatitis B, chronic rheumatoid arthritis, sepsis, graft versus host disease, insulin dependent diabetes mellitus, nephritis, traumatic brain damage, inflammatory enteropathy, allergy, atopy, asthma, pollinosis, airway hypersensitivity, or autoimmune disease.

(49) A method of screening for a compound that regulates the expression level of the protein according to any one of (1) to (10), which comprises the steps of: (a) comparing (i) the expression level of the protein according to any one of (1) to (10) in a cell expressing the protein, and (ii) the expression level of the protein in the cell contacted with a test sample; and (b) selecting the compound that regulates the expression level of the protein according to any one of (1) to (10) from the test samples.

(50) A method of screening for a compound that regulates the function of the protein according to any one of (1) to (10), which comprises the steps of: (a) comparing the function of (i) a cell expressing the protein according to any one of (1) to (10) and the function of (ii) the cell contacted to a test sample; and (b) selecting the compound that regulates the function of the protein according to any one of (1) to (10) from the test sample.

(51) A method of screening for a compound that regulates the expression of a gene encoding the protein according to any one of (1) to (10), which comprises the steps of: (a) contacting a transformant transformed with a plasmid containing a DNA wherein a reporter gene is connected downstream of a region regulating the transcription of a gene encoding the protein according to any one of (1) to (10) with a test sample; and (b) selecting the compound that regulates the expression of the gene encoding the protein according to any one of (1) to (10) from the test sample.

(52) A method of screening for a compound that regulates the splicing of a gene encoding the protein according to any one of (1) to (10) from a test sample using the cell expressing the protein according to any one of (1) to (10), which comprises the steps of: (a) contacting the cell expressing said protein with the test sample; and (b) comparing (i) the expression level of the protein according to any one of (1) or (A) of (3) to (10) in said cell, and (ii) the expression level of the protein according to any one of (2) or (B) of (3) to (10) in said cell.

(53) A compound or pharmacologically acceptable salt thereof, which is obtainable by the screening method according to any one of (49) to (52).

(54) A medicament containing the compound or pharmacologically acceptable salt thereof of (53).

(55) The medicament according to (54), wherein the medicament is a preventive agent or a therapeutic agents for diseases accompanying abnormal cell growth, diseases accompanying angiopathy, diseases accompanying abnormal bone metabolism, diseases accompanying disorders of insulin-like growth factors or growth hormone action, diseases accompanying abnormal differentiation or growth of smooth muscle cells, diseases accompanying abnormal differentiation or growth of skeletal muscle cells, diseases accompanying abnormal gastric acid secretion, or inflammatory diseases accompanying abnormal lymphocyte invasion.

(56) The medicament according to (55), wherein the disease accompanying abnormal cell growth is acute myelogenous leukemia, breast cancer, prostate cancer, colon cancer, hepatic cancer, myeloma, uterine leiomyoma, malignant tumor, or solid tumor; the disease accompanying angiopathy is myocardial infarction, cerebral infarction, peripheral vascular atresia, angina pectoris, hypertension, hyperlipidemia, diabetes, diabetic retinopathy, glomerulonephritis, arteriosclerosis, thrombosis, hemolytic uremic syndrome, thrombotic thrombocytopenic purpa, ischemic heart disease, ischemic encephalopathy, heart failure, hemostasis, or choroid circulatory dysfunction; the disease accompanying abnormal bone metabolism is osteoporosis; the disease accompanying disorders of insulin-like growth factors or growth hormone action is dwarfism, acromegaly, or infantile chronic renal failure; the disease accompanying abnormal differentiation or growth of smooth muscle cells is arteriosclerosis, bronchial disease, or restenosis; the disease accompanying abnormal differentiation or growth of skeletal muscle cells is myasthenia gravis; the disease accompanying abnormal gastric acid secretion is gastric ulcer; and the inflammatory disease accompanying abnormal lymphocyte invasion is microbial infection, chronic hepatitis B, chronic rheumatoid arthritis, sepsis, graft versus host disease, insulin dependent diabetes mellitus, nephritis, traumatic brain damage, inflammatory enteropathy, allergy, atopy, asthma, pollinosis, airway hypersensitivity, or autoimmune disease.

(57) A method of screening for a substance that specifically binds to the protein or polypeptide according to any one of (1) to (12), which comprises the steps of: (a) contacting the protein or polypeptide according to any one of (1) to (12) with a test sample; and (b) selecting the substance that specifically binds to the protein or polypeptide from the test sample.

(58) A substance that specifically binds to the protein or polypeptide according to any one of (1) to (12), which is obtained by the screening method of (57).

(59) A non-human knockout animal, wherein the expression of a gene encoding the protein according to any one of (1) to (10) is decreased or completely inhibited.

(60) A non-human knockout animal, wherein the function of the protein according to any one of (1) to (10) is decreased or completely inhibited.

Proteins and polypeptides of the present invention comprise the following:

(a) an insulin-like growth factor binding protein that comprises the amino acid sequence shown in SEQ ID NO: 1;

(b) an insulin-like growth factor binding protein that comprises the amino acid sequence shown in SEQ ID NO: 2;

(c) a protein comprising an amino acid sequence, wherein one or more amino acids have been deleted, substituted, or added in the amino acid sequence shown in SEQ ID NO: 1, and which substantially has an identical activity to the protein of (a);

(d) a protein comprising an amino acid sequence, wherein one or more amino acids have been deleted, substituted, or added in the amino acid sequence shown in SEQ ID NO: 2, and which substantially has an identical activity to the protein of (b);

(e) a protein comprising an amino acid sequence having 60% or higher identity with the amino acid sequence shown in SEQ ID NO: 1, wherein the protein substantially has an identical activity to the protein of (a);

(f) a protein comprising an amino acid sequence having 60% or higher identity with the amino acid sequence shown in SEQ ID NO: 2, wherein the protein substantially has an identical activity to the protein of (b);

(g) a protein comprising an amino acid sequence that includes the 75th to the 82nd amino acid residues of the amino acid sequence shown in SEQ ID NO: 1, wherein the protein substantially has an identical activity to the protein of (a);

(h) a protein comprising an amino acid sequence that includes the 75th to the 82nd amino acid residues of the amino acid sequence shown in SEQ ID NO: 2, wherein the protein substantially has an identical activity to the protein of (b);

(i) a protein comprising an amino acid sequence, wherein one or more amino acids are deleted, substituted, or added in the amino acid sequence of (g), which substantially has an identical activity as the protein of (a);

(j) a protein comprising an amino acid sequence, wherein one or more amino acids are deleted, substituted, or added in the amino acid sequence of (h), which substantially has an identical activity to the protein of (b);

(k) a protein comprising an amino acid sequence having 60% or higher identity with the amino acid sequence of (g), wherein the protein substantially has an identical activity to the protein of (a);

(l) a protein comprising an amino acid sequence having 60% or higher identity with the amino acid sequence of (h), wherein the protein substantially has an identical activity to the protein of (b);

(m) the protein comprising a partial amino acid sequence that includes the 171st to the 304th amino acid residues of the amino acid sequence shown in SEQ ID NO: 1, wherein the protein substantially has an identical activity to the protein of (a);

(n) the protein comprising a partial amino acid sequence that includes the 171st to the 197th amino acid residues of the amino acid sequence shown in SEQ ID NO: 2, wherein the protein substantially has an identical activity to the protein of (b);

(o) a protein comprising an amino acid sequence, wherein one or more amino acids are deleted, substituted, or added in the amino acid sequence of (m), which substantially has an identical activity to the protein of (a);

(p) a protein comprising an amino acid sequence, wherein one or more amino acids are deleted, substituted, or added in the amino acid sequence of (n), which substantially has an identical activity to the protein of (b);

(q) a protein comprising an amino acid sequence having 60% or higher identity with the amino acid sequence of (m), wherein the protein substantially has an identical activity to the protein of (a);

(r) a protein comprising an amino acid sequence having 60% or higher identity with the amino acid sequence of (n), wherein the protein substantially has an identical activity to the protein of (b);

(s) a polypeptide comprising an amino acid sequence that includes at least 5 or more continuous amino acids in the amino acid sequence shown in SEQ ID NO: 1;

(t) a polypeptide comprising an amino acid sequence that includes at least 5 or more continuous amino acids in the amino acid sequence shown in SEQ ID NO: 2;

(u) a polypeptide comprising an amino acid sequence that includes at least 5 or more continuous amino acids of the 171st to the 304th amino acid residues in the amino acid sequence shown in SEQ ID NO: 1; and (v) a polypeptide comprising an amino acid sequence that includes at least 5 or more continuous amino acids of the 171st to the 197th amino acid residues in the amino acid sequence shown in SEQ ID NO: 2.

A factor belonging to the insulin-like growth factor binding protein superfamily has the affinity to IGF or insulin and an insulin-like growth factor binding motif (IGFBP motif). The motif is conserved in the N-terminal region of proteins belonging to the insulin-like growth factor binding protein superfamily, and refers to a region of the protein consisting of the amino acid sequence represented by Gly-Cys-Gly-Cys-Cys-X-X-Cys (SEQ ID NO:26) (X refers to an arbitrary amino acid).

At least 10 cysteine residues are conserved, mainly as the IGFBP motif, in proteins belonging to the insulin-like growth factor binding protein, and these proteins show an affinity to IGF or insulin via the IGFBP motif region. The amino acid sequence represented by the 75th to the 82nd amino acid in the amino acid sequence shown in SEQ ID NO: 1, and the 75th to the 82nd amino acid residues in the amino acid sequence shown in SEQ ID NO: 2 are the IGFBP motifs.

Examples of the above-mentioned proteins having substantially identical activity to the protein having the amino acid sequence shown in SEQ ID NO: 1 or SEQ ID NO: 2 include those which bind to the same protein, such as integrin, IGF, insulin, or receptors, as the protein having the amino acid sequence shown in SEQ ID NO: 1 or SEQ ID NO: 2. The term "substantially identical" indicates that the activity is qualitatively identical. Therefore, quantitative factors, such as the degree of binding activity and molecular weight of the protein, may be different.

A protein which comprises an amino acid sequence wherein one or more amino acids are deleted, substituted, or added in the amino acid sequence shown in SEQ ID NO: 1 coding for the protein of the present invention, and which substantially has an identical activity to the protein of SEQ ID NO: 1, or a protein which comprises an amino acid sequence wherein one or more amino acids are deleted, substituted, or added in the amino acid sequence shown in SEQ ID NO: 2 coding for the protein of the present invention, and which substantially has an identical activity to the protein of SEQ ID NO: 2 can be obtained by site-directed mutagenesis of a DNA coding for a protein having an amino acid sequence shown in, for example, SEQ ID NO: 1 or 2, using the method for site-directed mutagenesis described, for example, in Molecular Cloning, A Laboratory Manual, Second Edition, Cold Spring Harbor Laboratory Press (1989) (hereinafter, abbreviated as Molecular Cloning Second Edition); Current Protocols in Molecular Biology, John Wiley & Sons (1987-1997) (hereinafter, abbreviated as Current Protocols in Molecular Biology); Nucleic Acids Research, 10, 6487 (1982); Proc. Natl. Acad. Sci., USA, 79, 6409 (1982); Gene, 34, 315 (1985); Nucleic Acids Research, 13, 4431 (1985); and Proc. Natl. Acad. Sci., USA, 82, 488 (1985). The numbers of amino acid(s) which is/are deleted, substituted, or added is more than 1 and there is no particular limitation on the numbers so long as they can be deleted, substituted or added by conventional methods, such as site-directed mutagenesis described above, for example, one to several tens amino acid(s), preferably one to twenty amino acid(s), more preferably one to ten amino acid(s), still more preferably one to five amino acid(s). Furthermore, the proteins of the present invention include not only such artificially prepared variants but also naturally-occurring variants.

So that a protein substantially has an identical activity to the protein consisting of the amino acid sequence shown in SEQ ID NO: 1 or 2, it is preferred that the protein consists of an amino acid sequence having at least 60% or more, preferably 70% or more, more preferably 80% or more, still more preferably 90% or more, particularly more preferably 95% or more, and most preferably 97% or more identity to the amino acid sequence shown in SEQ ID NO: 1 or 2.

The identity of amino acid sequences or nucleotide sequences can be determined with the BLAST algorithms of Karlin and Altschul (Proc. Natl. Acad. Sci. USA, 90, 5873-5877 (1993)) and FASTA (Methods Enzymol., 183, 63 (1990)). Based on the BLAST algorithm, the programs, BLASTN and BLASTX, have been developed (J. Mol. Biol., 215, 403 (1990)). When nucleotide sequences are analyzed by BLASTN based on BLAST, the parameters are set, for example, as follows: score=100; and wordlength=12. Alternatively, when amino acid sequences are analyzed by BLASTX based on BLAST, the parameters are set, for example, as follows: score=50; and wordlength=3. When BLAST and the Gapped BLAST program are used for the analysis, the default parameters are used in each program. The specific techniques used in these analysis methods are already known (www.ncbi.nlm.nih.gov.).

The proteins of the present invention are proteins that have a partial amino acid sequence of the above-mentioned protein of the present invention, and includes proteins that substantially have identical activity to the protein having the amino acid sequence shown in SEQ ID NO: 1 or 2.

So that a protein substantially has an identical activity to the protein having the amino acid sequence shown in SEQ ID NO: 1 or 2, it is preferred that the protein comprises a partial amino acid sequence containing the 75th to the 82nd amino acid residues of the amino acid sequence shown in SEQ ID NO: 1, or the 75th to the 82nd amino acid residues in the amino acid sequence shown in SEQ ID NO: 2.

A protein having an amino acid sequence wherein one or more amino acids in the amino acid of such protein are deleted, substituted, or added, is also included in the protein of the present invention. An example of the protein includes the above-mentioned protein wherein a number of amino acids that can be deleted, substituted, or added by well-known site directed mutagenesis method are modified and which substantially has an identical activity to the protein having the amino acid sequence shown in SEQ ID NO: 1 or 2.

An example of a protein of the present invention comprising an amino acid sequence wherein one or more amino acids are deleted in the amino acid sequence shown in SEQ ID NO: 1 or 2 which substantially has an identical activity to a protein consisting of the amino acid sequence shown in SEQ ID NO: 1 or 2, includes a protein wherein the signal peptide has been removed.

Furthermore, proteins having 60% or higher identity with the above-mentioned protein of (g), (h), (m), or (n), which substantially have an identical activity to the protein having the amino acid sequence shown in SEQ ID NO: 1 or 2, are also included in the proteins of the present invention. So that a protein substantially has an identical activity to a protein having the amino acid sequence shown in SEQ ID NO: 1 or 2, its identity with the amino acid sequence of the protein of (g), (h), (m), or (n) is at least 60% or higher, preferably 70% or higher, more preferably 80% or higher, even more preferably 90% or higher, especially preferably 95% or higher, and most preferably 97% or higher, when the identity is calculated by, for example, analysis software, such as BLAST described above.

There are no limitations on the polypeptides of the present invention so long as the polypeptides can be used as antigenic polypeptides for producing antibodies that recognize the above-mentioned proteins of the present invention. However, specific examples include polypeptides comprising 5 or more continuous amino acids of the amino acid sequence shown in SEQ ID NO: 1 or 2, preferably 10 or more, and more preferably 15 or more. For producing antibodies that can distinguish proteins consisting of the amino acid sequence shown in SEQ ID NO: 1 and SEQ ID NO: 2, particularly useful polypeptides include those consisting of 5 or more, preferably 10 or more, and more preferably 15 or more continuous amino acids of the 171st to the 304th amino acid residues in the amino acid sequence shown in SEQ ID NO: 1 or the 171st to the 197th amino acid residues in the amino acid sequence shown in SEQ ID NO: 2.

The DNA of the present invention includes the following:
(1) a DNA having the nucleotide sequence shown in SEQ ID NO: 3;
(2) a DNA having the nucleotide sequence shown in SEQ ID NO: 4;
(3) a DNA encoding the protein of the present invention according to (a), (c), (e), (g), (i), (k), (m), (o), or (q) defined above;
(4) a DNA encoding the protein of the present invention according to (b), (d), (f), (h), (o), (l), (n), (p), or (r) defined above;
(5) a DNA that hybridizes under stringent conditions to the DNA of (3) or a DNA comprising the nucleotide sequence shown in SEQ ID NO: 3 from the 177th to the 1088th bases, which encodes a protein that substantially has an identical activity to the protein having the amino acid sequence shown in SEQ ID NO: 1;
(6) a DNA that hybridizes under stringent conditions to the DNA of (4) or a DNA comprising a nucleotide sequence shown in SEQ ID NO: 4 from the 926th to the 1516th bases, which encodes a protein that substantially has an identical activity to the protein having the amino acid sequence shown in SEQ ID NO: 2;
(7) a DNA encoding the polypeptide of (s) or (u) defined above; and
(8) a DNA encoding the polypeptide of (t) or (v) defined above.

The "DNA that hybridizes under stringent conditions" refers to a DNA that can be obtained by colony hybridization, plaque hybridization, Southern blot hybridization, or the like, using the DNA of the present invention, such as those having the nucleotide sequence shown in SEQ ID NO: 3 or 4, or fragments thereof as a probe. Specifically, such DNA includes a DNA that can be identified by carrying out hybridization at 65° C. in the presence of 0.7 to 1.0 mol/L NaCl using a filter, on which a DNA derived from a colony or plaque is immobilized; and then washing the filter under a condition of 65° C. with 0.1× to 2×SSC solution (1×SSC solution consists of 150 mmol/L NaCl, 15 mmol/L sodium citrate). The hybridization can be performed according to the method described in, for example, "Molecular Cloning, Second Edition"; "Current Protocols in Molecular Biology"; and "DNA Cloning 1: Core Techniques, A Practical Approach, Second Edition", Oxford University Press (1995). Specific examples of hybridizing DNAs include a DNA exhibiting at least 60% or higher, preferably 70% or higher, more preferably 80% or higher, still more preferably 90% or higher, particularly preferably 95% or higher, most preferably 98% or higher identity with the nucleotide sequence shown in SEQ ID NO: 3 or 4, when the identity is computed by, for example, analysis software such as BLAST described above.

The above-mentioned DNAs of (7) and (8) are DNAs encoding the polypeptides of the present invention, and thus can be used for producing the polypeptides of the present invention, and for detecting the expression or measuring the expression level of DNAs containing the coding region of the nucleotide sequence shown in SEQ ID NO: 3 or 4. In particular, DNAs encoding the polypeptides of the above-mentioned (u) and (v) are useful for diagnosis of a disease characterized by an abnormal expression ratio of the protein of SEQ ID NO: 1 to the protein of SEQ ID NO: 2, wherein the expression levels of a DNA containing the coding region of the nucleotide sequence shown in SEQ ID NO: 3 and a DNA containing the coding region of the nucleotide sequence shown in SEQ ID NO: 4 are compared.

DETAILED DESCRIPTION OF THE INVENTION

The present invention is described in detail below.

1. Preparation of DNAs of the Present Invention

A DNA of the present invention can be prepared by isolating human tissue-derived mRNAs, for example, human small intestine-derived mRNA; preparing their cDNA library; and then screening the cDNA library to obtain a clone of interest.

Commercially available human small intestine mRNAs (for example, those from Clontech) may be used, or human small intestine mRNAs may be prepared from human small intestine tissues as described below. In the latter case, first, total RNA is prepared from small intestine tissue, and then mRNA can be isolated from the total RNA.

Examples of methods for preparing total RNA from small intestine tissue include the guanidine thiocyanate-cesium trifluoroacetate method (Methods in Enzymology, 154, 3 (1987)), and the acid guanidine thiocyanate-phenol-chloroform (AGPC) method (Analytical Biochemistry, 162, 156 (1987); Experimental Medicine, 9, 1937 (1991)). Examples of methods for preparing mRNA as poly(A)+ RNA from total RNA include the oligo(dT) immobilized cellulose column method (Molecular Cloning, 2nd edition), and the like. Alternatively, mRNA can be prepared using a kit such as Fast Track mRNA Isolation Kit (Invitrogen) and Quick Prep mRNA Purification Kit (Pharmacia).

A cDNA library is constructed from the prepared human small intestine tissue mRNA. Examples of methods for constructing the cDNA library include methods described in Molecular Cloning, second edition, Current Protocols in Molecular Biology, and the like, or methods using commercially available kits, for example, SuperScript Plasmid System for cDNA Synthesis and Plasmid Cloning (Life Technologies), and ZAP-cDNA Synthesis Kit (STRATAGENE).

Phage vectors, plasmid vectors, and such can be used as the cloning vector for constructing the cDNA library so long as they can self-replicate in *Escherichia coli* K12 cell line. Specific examples include: ZAP Express (STRATAGENE; Strategies, 5, 58 (1992)); pBluescript II SK(+) (Nucleic Acids Research, 17, 9494 (1989)); Lambda ZAP II (STRATAGENE); λgt10; λgt11 (DNA cloning, A Practical Approach, 1, 49 (1985)); λTriplEx (Clontech); λExCell (Pharmacia); pT7T318U (Pharmacia); pcD2 (Mol. Cell. Biol., 3, 280 (1993)); pUC18 (Gene, 33, 103 (1985)); and the like.

Any host microorganism can be used, as long as it belongs to the genus *Escherichia*, in particular, to *Escherichia coli*. Specifically, *Escherichia coli* XL1-Blue MRF' (STRATAGENE, Strategies, 5, 81 (1992)), *Escherichia coli* C600 (Genetics, 39, 440 (1954)), *Escherichia coli* Y1088 (Science, 222, 778 (1983)), *Escherichia coli* Y1090 (Science, 222, 778 (1983)), *Escherichia coli* NM522 (J. Mol. Biol., 166, 1 (1983)), *Escherichia coli* K802 (J. Mol. Biol., 16, 118 (1966)), *Escherichia coli* JM105 (Gene, 38, 275 (1985)), and the like are used.

The cDNA library may be used directly for the following analyses, or a cDNA library prepared according to the oligo-capping method developed by Kanno et al. (Gene, 138, 171 (1994); Gene, 200, 149 (1997); Protein, Nucleic Acid, and Enzyme, 41, 603 (1996); Experimental Medicine, 11, 2491 (1993); "cDNA Cloning", Yodosha (1996); "Idenshi Raiburari no Sakuseiho (Method for Producing Gene Libraries)", Yodosha (1994)) to efficiently obtain full-length cDNA while lowering the proportion of cDNAs with incomplete-length may be used.

The nucleotide sequence of a DNA is determined by isolating each clone from the prepared cDNA library; and analyzing the nucleotide sequence of the cDNA for each clone from the end by ordinarily used nucleotide sequence analysis methods, for example, the dideoxy method of Sanger et al. (Proc. Natl. Acad. Sci. USA, 74, 5463 (1977)), or using nucleotide sequence analyzer, such as ABIPRISM377 DNA sequencer (PE Biosystems).

Whether respective cDNA nucleotide sequences have a novel sequence or not can be determined by confirming the absence of a nucleotide sequence with such an obvious homology that indicates a completely matching nucleotide sequence to a gene existing in the database by searching nucleotide sequence database, such as GenBank, EMBL, and DDBJ, using a homology search program, such as BLAST.

An example of nucleotide sequences of cDNAs containing a novel sequence obtainable by the above-mentioned method includes the nucleotide sequence shown in SEQ ID NOS: 3 and 4.

The protein (the protein consisting of the amino acid sequence shown in SEQ ID NO: 1) that is obtained by translating the DNA consisting of the nucleotide sequence shown in SEQ ID NO: 3 shows 38% homology to human IGFBP-7, a protein belonging to the IGFBP superfamily, according to the homology analysis using BLAST2 (Nuc. Acid. Res., 25, 3389 (1997)).

The protein (the protein consisting of the amino acid sequence shown in SEQ ID NO: 2) that is obtained by translating the DNA consisting of the nucleotide sequence shown in SEQ ID NO: 4 shows 35% homology to human IGFBP-7, a protein belonging to the IGFBP superfamily, according to the homology analysis using BLAST2.

Positions of at least 10 cysteine residues, mainly in the insulin-like growth factor binding motif region and the IGFBP motif that are important for binding with IGF or insulin, are known to be conserved in the IGFBP superfamily. Similarly, in the proteins consisting of the amino acid sequences shown in SEQ ID NO: 1 and 2, an amino acid sequence consisting of Ala-Gly-Gly-Cys-Cys-Trp-Glu-Cys (SEQ ID NO:27) that is extremely similar to the amino acid sequence of Gly-Cys-Gly-Cys-Cys-X-X-Cys (SEQ ID NO:26) (X indicates an arbitrary amino acid), a representative insulin-like growth factor binding motif, exists at the region corresponding to the insulin-like growth factor binding motif; and 10 cysteine residues, mainly in this motif region, exist at positions that are conserved among factors belonging to the IGFBP superfamily. Therefore, it is clear that proteins consisting of the amino acid sequences shown in SEQ ID NO: 1 and SEQ ID NO: 2 have the activity of a protein belonging to the IGFBP superfamily.

Proteins belonging to the IGFBP superfamily are reported to be associated with diseases including diseases accompanying abnormal cell growth, such as acute myelogenous leukemia, breast cancer, prostate cancer, colon cancer, hepatic cancer, myeloma, uterine leiomyoma, malignant tumor, and solid tumor; diseases accompanying angiopathy, such as myocardial infarction, cerebral infarction, peripheral vascular atresia, angina pectoris, hypertension, hyperlipidemia, diabetes, diabetic retinopathy, glomerulonephritis, arteriosclerosis, thrombosis, hemolytic uremic syndrome, thrombotic thrombocytopenic purpa, ischemic heart disease, ischemic encephalopathy, heart failure, hemostasis, and choroid circulatory dysfunction; diseases accompanying abnormal bone metabolism, such as osteoporosis; diseases accompanying disorders of insulin-like growth factors or growth hormone action, such as dwarfism, acromegaly, and infantile chronic renal failure; diseases accompanying abnormal differentiation or growth of smooth muscle cells, such as arteriosclerosis, bronchial disease, and restenosis; diseases accompanying abnormal differentiation or growth of skeletal muscle cells, such as myasthenia gravis; diseases accompanying abnormal gastric acid secretion, such as gastric ulcer; and inflammatory diseases accompanying abnormal lymphocyte invasion, such as microbial infection, chronic hepatitis B, chronic rheumatoid arthritis, sepsis, graft versus host disease, insulin dependent diabetes mellitus, nephritis, traumatic brain damage, inflammatory enteropathy, allergy, atopy, asthma, pollinosis, airway hypersensitivity, and autoimmune disease. Therefore, the proteins of the present invention are also predicted to be associated with the above-mentioned diseases.

Due to a comparison of the nucleotide sequence shown in SEQ ID NO: 3 with that shown in SEQ ID NO: 4, it can be seen that they share a common sequence. In such a case, to confirm that these molecules were not artificially formed during the cDNA library production, the human genome library is screened using sequences specific to the nucleotide sequence shown in SEQ ID NO: 3 or 4, and the nucleotide sequence of the obtained genomic clones are determined.

Commercially available products (for example, BAC library from Research Genetics) can be used as the human genome library of the present invention; or it may be prepared from human cells or tissues using known methods (methods described in Genomics, 29, 413 (1995); Genomics, 24, 527 (1994); etc.).

Examples of methods for screening human genome library using a sequence specific to the nucleotide sequence shown in SEQ ID NO: 3 or 4 include: PCR methods using primers specific to the nucleotide sequence shown in SEQ ID NO: 3 or 4 (PCR Protocols, Academic Press (1990)); colony hybridization or plaque hybridization methods (Molecular Cloning 2nd edition) using oligonucleotides specific to the nucleotide sequence shown in SEQ ID NO: 3 or 4; and the like.

According to the above-mentioned method, a genomic DNA clone (for example, human genome BAC clone) containing both of the nucleotide sequences shown in SEQ ID NO: 3 and SEQ ID NO: 4 can be obtained. Determination of the nucleotide sequence of this genomic DNA followed by the comparison with the nucleotide sequences shown in SEQ ID NO: 3 and SEQ ID NO: 4 reveal that the nucleotide sequence shown in SEQ ID NO: 3 and the nucleotide sequence shown in SEQ ID NO: 4 exist over a span of approximately 7 kb on the same human genome separated into 5 and 7 regions, respectively. That is, the protein having the amino acid sequence shown in SEQ ID NO: 1 is composed of 5 exons and the protein having the amino acid sequence shown in SEQ ID NO: 2 is composed of 7 exons; and the second and fourth exons of the genes are completely concordant to each other. However, the beginning of the third exon and the end of the fifth exon are different from each other, which result in the difference observed by comparing the amino acid sequences shown in SEQ ID NOS: 1 and 2. Therefore, the protein having the amino acid sequence shown in SEQ ID NO: 1 and the protein having the amino acid sequence shown in SEQ ID NO: 2 are shown to be discrete products of alternately spliced forms derived from the same gene, which show an unique characteristic of having different amino acid sequences from each other.

Once the DNA consisting of the nucleotide sequence shown in SEQ ID NO: 3 or 4 is obtained and the nucleotide sequence thereof is determined, a DNA of the present invention can be obtained by preparing primers based on the 5' end and 3' end nucleotide sequences of such nucleotide sequence, and amplifying DNA by PCR method (PCR Protocols, Academic Press (1990)) using cDNAs or a cDNA library synthesized from mRNAs contained in tissues or cells, such as small intestine of human or non-human animal as a template.

Alternatively, a DNA of the present invention can be obtained using a full length DNA shown in SEQ ID NO: 3 or 4, or parts thereof as a probe to conduct colony hybridization or plaque hybridization (Molecular Cloning, 2nd edition) against cDNAs or cDNA libraries synthesized from mRNAs contained in tissues or cells, such as small intestine of human or non-human animal.

Furthermore, based on the determined nucleotide sequence of the DNA, a DNA of the present invention can be obtained by chemical synthesis using DNA synthesizer, such as DNA synthesizer model 392 from Perkin Elmer, utilizing the phosphoramidite method.

The obtained DNA can be confirmed as a DNA encoding a protein having the activity as the IGFBP superfamily by expressing the protein using a transformant that can be obtained by transforming a recombinant vector containing the DNA into a host cell, or by comparing the identity and the cysteine residue positions between the amino acid sequence encoded by such DNA and the amino acid sequence of human IGFBP-1, human IGFBP-2, human IGFBP-3, human IGFBP-4, human IGFBP-5, human IGFBP-6, human IGFBP-7, human IGFBP-8, human IGFBP-9, or human IGFBP-10.

Based on the information relating to the nucleotide sequences shown in SEQ ID NOS: 3 and 4 or the nucleotide sequence of a fragment thereof, oligonucleotides that have the nucleotide sequence of the present DNA, for example, one corresponding to 5 to 60, preferably 10 to 40 continuous bases of the nucleotide sequence shown in SEQ ID NO: 3 or 4, and oligonucleotides corresponding to sequences that are complementary to the above oligonucleotides (hereinafter, referred to as antisense oligonucleotide) can be prepared using ordinary methods or DNA synthesizer.

Examples of oligonucleotides of the present invention include oligonucleotides, such as oligo-DNA and oligo-RNA, derivatives of such oligonucleotides (hereinafter, referred to as oligonucleotide derivatives), and so on.

Such oligonucleotides or antisense oligonucleotides are exemplified by sense primers corresponding to the 5' end nucleotide sequence of a part of the nucleotide sequence of a mRNA to be detected, antisense primers corresponding to the 3' end nucleotide sequence of the mRNA, and so on. However, the base corresponding to uracil of the mRNA is thymidine in the oligonucleotide primer.

Examples of the sense primers and antisense primers include oligonucleotides, whose melting temperature (Tm) and number of bases do not change excessively, and the number of bases is 5 to 60, preferably 10 to 50.

The oligonucleotide derivatives are exemplified by oligonucleotide derivatives wherein the phosphodiester bond of the oligonucleotide has been converted to a phosphorothioate bond; oligonucleotide derivatives wherein phosphodiester bond in the oligonucleotide has been converted to a N3'-P5' phosphoramidate bond; oligonucleotide derivatives wherein the phosphodiester bond between ribose and phosphate in the oligonucleotide has been converted to a peptide-nucleic acid bond; oligonucleotide derivatives wherein uracil of the oligonucleotide has been substituted with C-5 propynyluracil; oligonucleotide derivatives wherein uracil of the oligonucleotide has been substituted with C-5 thiazoleuracil; oligonucleotide derivatives wherein cytosine of the oligonucleotide has been substituted with C-5 propynylcytosine; oligonucleotide derivatives wherein cytosine of the oligonucleotide has been substituted with phenoxazine-modified cytosine; oligonucleotide derivatives wherein ribose of the oligonucleotide has been substituted with 2'-O-propylribose; oligonucleotide derivatives wherein ribose of the oligonucleotide has been substituted with 2'-methoxyethoxyribose, and the like (Cell Technology, 16, 1463 (1997)).

2. Production of protein or polypeptide of the present invention

A protein or polypeptide of the present invention may be produced by expression of a DNA of the present invention in host cells using methods described in Molecular Cloning Second Edition, Current Protocols in Molecular Biology, and the like, for example, by the following manner.

Based on a full-length cDNA, if necessary, a DNA fragment of an appropriate length containing a region coding for the protein is prepared.

The DNA fragment or the full-length cDNA is inserted downstream of a promoter of an appropriate expression vector to prepare a recombinant vector.

By introducing the recombinant vector into host cells suitable for the expression vector, a transformant which produces the protein of the present invention can be obtained.

With regard to a host cell, any cell may be used as long as it is capable of expressing the desired gene. Such a host cell includes bacteria, yeast, animal cells, insect cells, plant cells, etc.

An expression vector that can be used is autonomously replicable in the above host cell or is able to be integrated into chromosomes and contains a promoter at the position where the DNA coding for the protein of the present invention is transcribed.

When a prokaryote such as bacteria is used as a host cell, it is preferred that the recombinant vector containing the DNA coding for the protein of the present invention is autonomously replicable in prokaryote and that it is a vector containing a promoter, a ribosome-binding sequence, the gene coding for the protein of the present invention, and a transcription termination sequence. The vector may also contain a gene that regulates the promoter.

Examples of the expression vector are pBTrp2, pBTac1, and pBTac2 (all sold by Boehringer-Mannheim); pKK233-2 (Pharmacia); pSE280 (Invitrogen); pGEMEX-1 (Promega); pQE-8 (Qiagen); pKYP10 (Japanese Published Unexamined Patent Application No. 110600/83); pKYP200 [Agric. Biol. Chem., 48, 669 (1984)]; pLSA1 [Agric. Biol. Chem., 53, 277 (1989)]; pGEL1 [Proc. Natl. Acad. Sci. USA, 82, 4306 (1985)]; pBluescript II SK(−)(Stratagene); pTrs30 [prepared from *Escherichia coli* JM109/pTrS30 (FERM BP-5407)]; pTrs32 [prepared from *Escherichia coli* JM109/pTrS32 (FERM BP-5408)]; pGHA2 [prepared from *Escherichia coli* IGHA2 (FERM B-400), Japanese Published Unexamined Patent Application No. 221091/85]; pGKA2 [prepared from *Escherichia coli* IGKA2 (FERM BP-6798), Japanese Published Unexamined Patent Application No. 221091/85]; pTerm2 (U.S. Pat. Nos. 4,686,191, 4,939,094, and 5,160,735); pSupex, pUB 110, pTP5, pC194, and pEG400 [J. Bacteriol., 172, 2392 (1990)]; pGEX (Pharmacia); pET system (Novagen); and pSupex.

With regard to a promoter, any promoter may be used as long as it is able to function in host cells, and its examples are promoters derived from *Escherichia coli*, phage, and the like, including trp promoter ($P_{trp}$), lac promoter, $P_L$ promoter, $P_R$ promoter, and T7 promoter. It is also possible to use artificially designed and modified promoters, such as a promoter where two $P_{trp}$ are connected in tandem ($P_{trp}$×2), tac promoter, lacT7 promoter, and letI promoter.

It is preferred to use a plasmid where the distance between an initiation codon and Shine-Dalgarno sequence, which is a ribosome-binding sequence, is adjusted appropriately (for example, 6 to 18 nucleotides).

It is possible to improve the productivity of the desired protein by substituting nucleotide(s) in the nucleotide sequence in the region coding for the protein so as to give a codon which is optimum for the expression of the protein in the host.

In the recombinant vector of the present invention, although a transcription termination sequence is not always necessary for the expression of a DNA of the present invention, it is preferred to place a transcription termination sequence immediately downstream of the structural gene.

Examples of the host cell are microorganisms belonging to the genus *Escherichia*, the genus *Serratia*, the genus *Bacillus*, the genus *Brevibacterium*, the genus *Corynebacterium*, the genus *Microbacterium*, and the genus *Pseudomonas*, such as *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Serratia ficaria*, *Serratia fonticola*, *Serratia liquefaciens*, *Serratia marcescens*, *Bacillus subtilis*, *Bacillus amyloliquefaciens*, *Brevibacterium immariophilum* ATCC 14068, *Brevibacterium saccharolyticum* ATCC 14066, *Brevibacterium flavum* ATCC 14067, *Brevibacterium ammoniagenes*, *Brevibacterium lactofermentum* ATCC 13869, *Corynebacterium glutamicum* ATCC 13032, *Corynebacterium acetoacidophilum* ATCC 13870, *Microbacterium ammoniaphilum* ATCC 15354, *Pseudomonas* sp. D-0110, and the like.

A recombinant vector can be introduced into the above-mentioned host cells by any of methods for the introduction of DNA, for example, the method using calcium ion [Proc. Natl. Acad. Sci. USA, 69, 2110 (1972)], protoplast method (Japanese Published Unexamined Patent Application No. 248394/88), and the methods described in Gene, 17, 107 (1982) and Molecular & General Genetics, 168, 111 (1979).

When yeast is used as a host cell, examples for expression vector are YEP13 (ATCC 37115), YEp24 (ATCC 37051), and YCp50 (ATCC 37419).

With regard to a promoter, any promoter may be used as long as it is able to function in yeast cell lines, and its examples are promoters of genes of a glycolytic pathway such as hexokinase, PHO5 promoter, PGK promoter, GAP promoter, ADH promoter, gal 1 promoter, gal 10 promoter, heat shock protein promoter, MFα1 promoter, and CUP 1 promoter.

Examples of the host cell are microorganisms belonging to the genus *Saccharomyces*, the genus *Kluyveromyces*, the genus *Trichosporon*, and the genus *Schwanniomyces*, such as *Saccharomyces cerevisiae*, *Schizosaccharomyces pombe*, *Kluyveromyces lactis*, *Trichosporon pullulans*, and *Schwanniomyces alluvius*.

A recombinant vector can be introduced into yeast by any method as long as it enables introduction of DNA into yeast. Such a method includes the electroporation method [Methods. Enzymol., 194, 182 (1990)], the spheroplast method [Proc. Natl. Acad. Sci. USA, 84, 1929 (1978)], the lithium acetate method [J. Bacteriology, 153, 163 (1983)], and the method described in Proc. Natl. Acad. Sci. USA, 75, 1929 (1978).

When an animal cell is used as a host, examples of expression vectors include pcDNAI, pcDM8 (Funakoshi), pAGE107 [Japanese Published Unexamined Patent Application No. 22979/91; Cytotechnology, 3, 133 (1990)], pAS3-3 (Japanese Published Unexamined Patent Application No. 227075/90), pCDM8 [Nature, 329, 840 (1987)], pcDNAI/Amp (Invitrogen), pREP4 (Invitrogen), pAGE103 [J. Biochemistry, 101, 1307 (1987)], and pAGE210.

With regard to a promoter, any promoter may be used as long as it is able to function in animal cells, such as the promoter of immediate early (IE) gene of cytomegalovirus (CMV), early promoter of SV40, promoter of retrovirus, metallothionein promoter, heat shock promoter, and SRα promoter. It is also possible to use an enhancer for IE gene of human CMV together with a promoter.

Examples of the host cell are Namalwa cell, which is a human cell; COS cell, which is a simian cell; CHO cell, which is a cell of Chinese hamster; and HBT5637 (Japanese Published Unexamined Patent Application No. 299/88).

A recombinant vector can be introduced into animal cells by any method as long as the method enables introduction of DNA into animal cells, and its examples are the electroporation method [Cytotechnology, 3, 133 (1990)], the calcium phosphate method (Japanese Published Unexamined Patent Application No. 227075/90), and the lipofection method [Proc. Natl. Acad. Sci. USA, 84, 7413 (1987)].

When an insect cell is used as a host, it is possible to express a protein by the method described in, for example, "Current Protocols in Molecular Biology"; "Baculovirus Expression Vectors, A Laboratory Manual", W.H. Freeman and Company, New York (1992); and Bio/Technology, 6, 47 (1988).

Thus, a recombinant gene-introducing vector and a baculovirus are co-transfected into an insect cell to give a recombinant virus in a supernatant of insect cell culture, and then a recombinant virus is further infected to another insect cell to express a protein.

Examples of the gene-introducing vector used in such a method are pVL 1392, pVL 1393, and pBlueBacIII (all from Invitrogen).

Baculoviruses that can be used include, for example, *Autographa californica* nuclear polyhedrosis virus, which is a virus infecting to insects belonging to the subfamily Hadeninae.

Examples of an insect cell include Sf9 and Sf21, which are ovary cells of *Spodoptera frugiperda* ["Baculovirus Expression Vectors, A Laboratory Manual", W.H. Freeman and Company, New York (1992)]; and High 5 (Invitrogen), which is an ovary cell of *Trichoplusia ni*.

The above-mentioned recombinant gene-introducing vector and the above-mentioned baculovirus can be co-transfected into an insect cell for the preparation of a recombinant virus by, for example, the calcium phosphate method (Japanese Published Unexamined Patent Application No. 227075/90), the lipofection method [Proc. Natl. Acad. Sci. USA, 84, 7413 (1987)], and the like.

When a plant cell is used as a host cell, examples of an expression vector are Ti plasmid and tobacco mosaic virus vector.

Any promoter may be used as long as it is able to function in a plant cell, and its examples are 35S promoter of cauliflower mosaic virus (CaMV) and rice actin 1 promoter.

Examples of the host cell are cells of plants such as tobacco, potato, tomato, carrot, soybean, rape, alfalfa, rice, wheat, and barley.

A recombinant vector can be introduced by any method as long as the method enables introduction of DNA into a plant cell, and its examples are methods using *Agrobacterium* (Japanese Published Unexamined Patent Application No.

140885/84 and 70080/85 and WO94/00977), the electroporation method (Japanese Published Unexamined Patent Application No. 251887/85), and methods using particle gun (Japanese Patent NOS. 2606856 and 2517813).

When yeast, animal cells, insect cells, or plant cells are used as host cells, it is possible to obtain the protein or the polypeptide to which sugar or sugar chain is added.

The transformant prepared as above is cultured in a medium, and the protein or the polypeptide of the present invention is produced and accumulated therein and then recovered from the culture, to produce the protein or the polypeptide of the present invention. The culturing the transformant of the present invention in a medium can be carried out according to common methods used for culturing the host.

A medium for culturing a transformant obtained using prokaryotes, such as *Escherichia coli*, or eukaryotes, such as yeast, as a host, may be any of natural and synthetic media as long as the medium contains carbon source, nitrogen source, inorganic salts, and the like, which can be assimilated by the organism and enables culturing the transformant efficiently.

Any source may be used as a carbon source as long as the organism is able to assimilate it, and its examples are carbohydrates, such as glucose, fructose, sucrose, molasses containing them, starch and hydrolyzed starch; organic acids, such as acetic acid and propionic acid; and alcohols, such as ethanol and propanol.

Examples of a nitrogen source include ammonia; ammonium salts of inorganic or organic acid, such as ammonium chloride, ammonium sulfate, ammonium acetate, and ammonium phosphate; other nitrogen-containing compounds; peptone; meat extract; yeast extract; corn steep liquor; hydrolyzed casein; soybean cake; hydrolyzed soybean cake; various fermented cells and digested products thereof; and the like.

Examples of an inorganic substance include potassium dihydrogen phosphate, dipotassium hydrogen phosphate, magnesium phosphate, magnesium sulfate, sodium chloride, ferrous sulfate, manganese sulfate, copper sulfate, calcium carbonate, and the like.

Usually, the transformant is cultured under an aerobic condition, for example, by shaking culture or submerged-aerated spinner culture. Temperature for the culturing is preferably 15 to 40° C., and time for the culturing is usually from 16 hours to seven days. The pH during the culturing is kept at pH 3.0 to pH 9.0. The pH is adjusted with inorganic or organic acid, an alkaline solution, urea, calcium carbonate, ammonia, etc.

During the culturing, antibiotic, such as ampicillin or tetracycline, may be added to the medium if necessary.

In the case of culturing a microorganism transformed with a recombinant vector in which an inducible promoter is used as a promoter, an inducer may be added to the medium if necessary. For example, when a microorganism transformed with a recombinant vector containing lac promoter is cultured, isopropyl-β-D-thiogalactopyranoside and the like may be added to the medium. When a microorganism transformed with a recombinant vector containing trp promoter is cultured, indole acrylic acid and the like may be added to the medium.

As the medium for a transformant obtained using animal cell as a host, the commonly used RPMI1640 medium [The Journal of the American Medical Association, 199, 519 (1967)], Eagle's MEM medium [Science, 122, 501 (1952)], modified Dulbecco's MEM medium [Virology, 8, 396 (1959)], 199 medium [Proceeding of the Society for the Biological Medicine, 73, 1 (1950)], a medium prepared by adding fetal calf serum, etc. to any of these media, and the like can be used.

The culturing is usually carried out for 1 to 7 days under the conditions, for example, of pH 6 to 8 at 30 to 40° C. in the presence of 5% $CO_2$.

During the culturing, antibiotics, such as kanamycin or penicillin, may be added to the medium if necessary.

As a medium for a transformant obtained using insect cell as a host, the commonly used TNM-FH medium (Pharmingen); Sf-900 II SFM medium (Life Technologies); ExCell400 and ExCell405 (both JRH Biosciences); Grace's Insect Medium (Grace, T. C. C., Nature, 195, 788 (1962)); and the like can be used.

The culturing is usually carried out for 1 to 5 days under the conditions, for example, of pH 6 to 7 at 25 to 30° C.

During the culturing, antibiotics, such as gentamycin, may be added to the medium if necessary.

A transformant obtained using plant cell as a host can be cultured in the form of cell or differentiated cell or organ of the plant. As the medium for the transformant, the commonly used Murashige and Skoog (MS) medium, White medium, or a medium prepared by adding phytohormone, such as auxin or cytokinin, to any of these medium, and the like can be used.

The culturing is usually carried out for 3 to 60 days under the conditions of pH 5 to 9 at 20 to 40° C.

During the culturing, antibiotics, such as kanamycin or hygromycin, may be added to a medium if necessary.

As mentioned above, a transformant derived from a microorganism, animal cell, or plant cell having a recombinant vector into which the DNA coding for the protein of the present invention has been incorporated is cultured by a conventional culturing method, and the protein or the polypeptide is produced and accumulated therein and is recovered therefrom to prepare the protein or the polypeptide.

The method for producing the protein or the polypeptide of the present invention includes intracellular production by host cells, extracellular secretion by host cells, production as a fusion protein, or production on outer membranes by host cells, and the method can be selected depending on the host cells used or on alteration of the structure of the protein to be produced.

When the protein of the present invention is produced inside of the host cell or on an outer membrane of the host cell, it is possible to secrete the protein extracellular portion of the host cell according to the method of Paulson et al. [J. Biol. Chem., 264, 17619 (1989)]; the method of Row et al. [Proc. Natl. Acad. Sci., USA, 86, 8227 (1989); Genes Develop., 4, 1288 (1990)], or the methods described in Japanese Published Unexamined Patent Application No. 336963/2003 and WO94/23021, etc.

Specifically, it is possible to secrete the protein of the present invention extracellular portion of the host cell vigorously by expressing the protein to which a signal peptide has been added to the upstream of the protein containing the active site of the protein by means of genetic engineering technique.

It is also possible to increase the production amount of the protein utilizing a gene-amplification system using a dihydrofolate reductase gene or such according to the method described in Japanese Published Unexamined Patent Application No. 227075/91.

Furthermore, by redifferentiating gene-transferred cells of animals or plants, individual gene-transferred animals (transgenic non-human animals) or plants (transgenic plants) are prepared, and using these individuals, a protein of the present invention can be produced.

When the transformant is an individual animal or plant, the protein can be produced by raising or cultivating the individual, generating and accumulating the protein, and then recovering the protein from the individual animal or plant according to conventional methods.

For example, a method for producing a protein of the present invention using an individual animal includes a method for producing the protein of the present invention in an animal produced by transferring a gene following known procedures (American Journal of Clinical Nutrition, 63, 639S (1996); American Journal of Clinical Nutrition, 63, 627S (1996); Bio/Technology, 9, 830 (1991)).

In the case of individual animals, the protein can be produced, for example, by raising a transgenic non-human animal transfected with DNA encoding the protein of the present invention; producing and accumulating the protein in the animal; and recovering the protein from the animal. For example, the place of production and accumulation in the animal may be milk (Japanese Published Unexamined Patent Application No. 309192/88), egg, and the like of the animal. Any promoter can be used so long as it can be expressed in the animal, and preferably includes, for example, mammary cell specific promoters such as α-casein promoter, β-casein promoter, β-lactoglobulin promoter, and whey acidic protein promoter.

Methods for producing a protein of the present invention using individual plants include, for example, a method wherein the protein is produced by cultivating a transgenic plant transfected with a DNA encoding the protein of the present invention according to known procedures (Tissue Culture, 20 (1994); Tissue Culture 21 (1995); Trends in Biotechnology, 15, 45 (1997)), producing and accumulating the protein within the plant, and then recovering the protein from the plant.

For example, when a protein of the present invention is expressed in a solubilized form within a cell, after cultivation, the cells are recovered by centrifugation; suspended into an aqueous buffer; homogenized by an ultrasonic homogenizer, French press, Manton Gaulin homogenizer, Dynomill, and the like; and the protein produced by the transformant of the present invention is obtained as a cell free extract solution. A purified preparation can be obtained from the supernatant obtained by centrifugation of the cell-free extract solution using either any one of conventional enzyme isolation and purification methods or in combination, such as the solvent extraction methods; the alt precipitation methods by ammonium sulfate and the like; desalting methods; precipitation by organic solvents; anion exchange chromatography methods using resins, such as diethylaminoethyl (DEAE)-sepharose, and DIAION HPA-75 (Mitsubishi Chemicals); cation exchange chromatography methods using resins, such as S-Sepharose FF (Pharmacia); hydrophobic chromatography methods using resins, such as butyl sepharose and phenyl sepharose; gel filtration methods using molecular sieves; affinity chromatography methods; chromatofocusing methods; and electrophoretic methods, such as isoelectric electrophoresis.

Furthermore, when a protein is expressed as insoluble bodies within a cell, similarly, the cells are recovered, homogenized, and then centrifuged to obtain the insoluble bodies of the protein as a precipitated fraction. The recovered insoluble bodies of the protein are solubilized with a protein denaturant. After restoring the normal three-dimensional structure of the protein by diluting or dialyzing the solubilized solution, a purified preparation of the protein can be obtained by isolation and purification methods similar to those mentioned above.

When a protein of the present invention or the derivative thereof, such as glycosylation products, is secreted outside of the cell, the protein or the derivative thereof, such as sugar chain adducts, can be recovered as the culture supernatant. Specifically, a soluble fraction is obtained by treating the culture with techniques, such as centrifugation, similar to those mentioned above, and then the purified preparation can be obtained from the soluble fraction using isolation and purification methods similar to those mentioned above.

An example of a protein obtained in this manner is, for example, a protein having the amino acid sequence shown in SEQ ID NO: 1 or SEQ ID NO: 2.

Alternatively, a protein of the present invention can be produced by chemical synthesis methods, such as Fmoc method (fluorenylmethoxycarbonyl method) and tBoc method (t-butoxycarbonyl method). Furthermore, chemical synthesis can be performed utilizing peptide synthesizers from Advanced ChemTech, Perkin Elmer, Pharmacia, Protein Technology Instrument, Synthecell-Vega, PerSeptive, Shimadzu, and the like.

3. Preparation of Antibodies Recognizing the Protein of the Present Invention

Using the proteins of the present invention, purified preparations of partial fragment polypeptides of these proteins, or peptides containing a partial amino acid sequence of the protein of the present invention as antigens, antibodies, such as polyclonal antibodies and monoclonal antibodies, recognizing the proteins of the present invention can be produced.

(1) Preparation of Polyclonal Antibody

The proteins of the present invention, purified samples of a partial polypeptide fragment of the proteins, and peptides comprising a partial amino acid sequences of the proteins of the present invention can be used as an antigen and administered into an animal to prepare a polyclonal antibody.

Such animals that can be utilized for the administration include rabbit, goat, rat, mouse, hamster, etc.

It is preferred to use the antigen in an administration dose of 50 μg to 100 μg per animal.

When a peptide is used for this purpose, it is preferred to use the peptide as an antigen after covalently linked to a carrier protein, such as keyhole limpet haemocyanin (KLH) or bovine thyroglobulin. The peptide to be used as the antigen can be synthesized by a peptide synthesizer.

After the first administration, the antigen is given 3 to 10 times at 1 to 2-week intervals. 3 to 7 days after each time of administration, blood is sampled from the venous plexus of eyegrounds. Then the serum is tested for the reactivity to the antigen used for the immunization by a method of enzyme immuno-assay ("Methods of Enzyme Immuno-Assay (ELISA): Igakushoin, 1976; "Antibodies: A Laboratory Manual", Cold Spring Harbor Laboratory Press (1988)), etc.

It is possible to obtain the polyclonal antibody by collecting the sera from non-human mammals that have exhibited sufficiently high antibody titers in their sera against the antigen used for the immunization, and separating and purifying the sera.

Such methods for the separation and purification include centrifugal separation, salting out with 40% to 50% saturated ammonium sulfate, precipitation by caprylic acid ("Antibodies: A Laboratory Manual", Cold Spring Harbor Laboratory (1988)), and a procedure using chromatographic methods, e.g., using DEAE-Sepharose column, anion exchange column, protein-A or -G column, gel filtration column, etc. singly or in combination.

(2) Preparation of Monoclonal Antibody (a) Preparation of Antibody-Producing Cells Rats, whose sera have exhibited sufficiently high titers of antibody against a partial polypeptide fragment of the present invention used for the immunization, are provided as the source of antibody-producing cells.

3 to 7 days after the final administration of the antigen substance to the rats that have exhibited such light titers of antibody, their spleens are removed from them.

The spleens are sectioned into small pieces in MEM medium (Nissui Pharmaceutical Co., Ltd.) and loosened by forceps. After centrifugation at 1,200 rpm for 5 minutes, the supernatant is discarded.

The resulting precipitated fraction of spleen cells is treated with Tris-ammonium chloride buffer (pH 7.65) for 1 to 2 minutes to remove red blood cells, and then the spleen cells are washed 3 times with MEM. The spleen cells prepared are used as antibody-producing cells.

(b) Preparation of Myeloma Cells

Myeloma cell to be used is a cell line established from mouse or rat. For example, 8-azaguanine resistant mouse (BALB/c-derived) myeloma cell lines that are usable include P3-X63Ag8-U1 (hereinafter, abbreviated as "P3-U1") (Curr. Topics Microbiol. Immunol., 81, 1 (1978); Eur. J. Immunol., 6, 511 (1976)), SP2/0-Ag14(SP-2) (Nature, 276, 269 (1978)), P3-X63-8653(653) (J. Immunol., 123, 1548 (1979)), P3-X63-Ag(×63) (Nature, 256, 495 (1975)), and the like. Cells of these lines are passaged in 8-azaguanine medium [RPMI1640 medium containing glutamine (1.5 mmol/L), 2-mercaptomethanol ($5 \times 10-5$ mol/L), gentamicin (10 µg/ml), and fetal calf serum (FCS) (CSL, 10%) (hereinafter referred to as normal medium) further containing 8-azaguanine (15 µg/ml)], but 3 to 4 days before the cell fusion the cells are cultured in the normal medium. $2 \times 10^7$ or more cells are used for the fusion.

(c) Preparation of Hybridoma

The antibody-producing cells prepared as described in (a) and myeloma cells in (b) are washed well with MEM or PBS (1.83 g of disodium phosphate, 0.21 g of potassium dihydrogenphosphate, 7.65 g of sodium chloride, 1 L of distilled water; pH 7.2); mixed with each other at a ratio of the numbers of antibody-producing cells: myeloma cells=5 to 10:1. After the mixture was subjected to centrifugation at 1,200 rpm for 5 minutes, the supernatant is discarded.

The mixed cells prepared from the precipitated fraction are well dispersed. While the cells are being stirred at 37° C., 0.2 to 1 ml (per 108 antibody-producing cells) of a solution of 2 g Polyethyleneglycol-1000 (PEG-1000), 2 ml MEM, and 0.7 ml dimethylsulfoxide (DMSO) is added to the cell mixture; then 1 to 2 ml of MEM is added thereto several times at 1 to 2-minute intervals. After the addition, the cells are so prepared by further adding MEM medium that the total volume becomes 50 ml. The prepared mixture is subjected to centrifugation at 900 rpm for 5 minutes, and then the supernatant is discarded. The cells from the resulting precipitated fraction are gently dispersed, suspended by gentle pipetting with a measuring pipette in 100 ml of HAT medium (a medium for which hypoxanthine ($10^{-4}$ mol/L), thymidine ($1.5 \times 10^{-5}$ mol/L), and aminopterin ($4 \times 10^{-7}$ mol/L) have been added to the normal medium).

A 100-µl aliquot of the suspension was dispensed into each well of a 96-well culture plate. Then the cells are cultured in an incubator with 5% $CO_2$ at 37° C. for 7 to 14 days.

After the culture is completed, an aliquot of the culture supernatant is utilized for the selection of hybridomas specifically reacting with a partial polypeptide fragment of the protein of the present invention according to enzyme immuno-assay methods described in "Antibodies, A Laboratory Manual" (Cold Spring Harbor Laboratory, Chapter 14 (1988)), and the like.

A specific example of the enzyme immuno-assay method is as follows.

An appropriate plate is coated with a partial peptide fragment of a protein of the present invention used as an antigen for the immunization. The hybridoma culture supernatant or purified antibody obtained in (d) as described below is reacted as a primary antibody, and an anti-rat immunoglobulin or an anti-mouse immunoglobulin antibody labeled with biotin, enzyme, chemically-luminescent substance, radioisotope, or the like is further reacted as a secondary antibody in the plate. Subsequently a reaction is carried out according to the label substance and cells exhibiting the specific reactivity to the protein of the present invention are selected as hybridomas producing monoclonal antibody against the protein of the present invention.

The hybridomas are cloned twice by the limiting dilution method [with HT medium (HAT medium without aminopterin) in the first cloning, and with the normal medium in the second]. Cells that stably exhibit high antibody titers are selected as hybridoma lines producing monoclonal antibody of the present invention.

(d) Preparation of Monoclonal Antibody

The hybridoma cells obtained in (c) producing the protein monoclonal antibody of the present invention are intraperitoneally injected (5 to $20 \times 10^6$ cells per mouse) to 8 to 10-week mice or nude mice treated with pristane (which have been subjected to intraperitoneal administration of 0.5 ml of 2,6, 10,14-tetramethylpentadecane (pristane) and have been bred for 2 weeks). The hybridomas form ascites carcinoma in 10 to 21 days.

The ascites is collected from each mouse having ascites tumor, and then is subjected to centrifugation at 3000 rpm for 5 minutes to remove the solid material.

The monoclonal antibodies can be purified and prepared from the resulting supernatant by the same method as used for the preparation of polyclonal antibody.

Subtyping of antibody can be performed using a typing kit for mouse or rat monoclonal antibody. The quantity of protein can be calculated according to Lowry method or by using absorbance at 280 nm.

4. Use of DNAs, Proteins, or Antibodies of the Present Invention (1) Method for Detecting Diseases by Detecting and Quantifying the Expression of DNA Encoding a Protein of the Present Invention Diseases, which are listed below, that are reported to be related to proteins belonging to the IGFBP superfamily can be detected by performing Northern hybridization method (Molecular Cloning 2nd edition); PCR method, and RT (reverse-transcribed)-PCR method (both in PCR Protocols, Academic Press (1990)) (all together referred to as PCR method); and the like using the DNAs or oligonucleotides of the present invention to detect the expression of DNAs encoding a protein of the present invention: diseases accompanying abnormal cell growth, such as acute myelogenous leukemia, breast cancer, prostate cancer, colon cancer, hepatic cancer, myeloma, uterine leiomyoma, malignant tumor, and solid tumor; diseases accompanying angiopathy, such as myocardial infarction, cerebral infarction, peripheral vascular atresia, angina pectoris, hypertension, hyperlipidemia, diabetes, diabetic retinopathy, glomerulonephritis, arteriosclerosis, thrombosis, hemolytic uremic syndrome, thrombotic thrombocytopenic purpa, ischemic heart disease, ischemic encephalopathy, heart failure, hemostasis, and choroid circulatory dysfunction; diseases accompanying abnormal bone metabolism such as osteoporosis; diseases accompanying disorders of insulin-like growth factors or growth hormone action, such as dwarfism, acromegaly, and infantile chronic renal failure; diseases accompanying abnormal differentiation or growth of smooth muscle cells, such as arteriosclerosis, bronchial disease, and restenosis; diseases accompanying abnormal differentiation or growth of skeletal muscle cells, such as myasthenia gravis; diseases accompanying abnormal gastric acid secretion such as gastric ulcer; and inflammatory diseases accompanying abnormal lymphocyte invasion, such as microbial infection, chronic hepatitis B, chronic rheumatoid arthritis, sepsis, graft versus host disease, insulin dependent diabetes mellitus, nephritis, traumatic brain damage, inflammatory enteropathy, allergy, atopy, asthma, pollinosis, airway hypersensitivity; etc.

Since RT-PCR method is a simple and convenient method, it is especially useful as a method for detecting the expression of DNAs.

For example, the above-mentioned diseases can be detected by performing Northern hybridization using a DNA having the same sequence as 100 to 1772 continuous bases in the nucleotide sequence shown in SEQ ID NO: 3, a DNA having a complementary sequence to such DNA, a DNA having the same sequence as 100 to 2698 continuous bases in the nucleotide sequence shown in SEQ ID NO: 4, or a DNA having a sequence complementary to such DNA as probes; quantifying the expression level of the DNA of SEQ ID NO: 3 or 4; and comparing the level to that of a healthy subject.

The following methods can be exemplified as specific methods for the detection.

Total RNAs (10 to 20 μg) or mRNAs thereof (1 to 5 μg) derived from leukocytes or tissues of a test subject and a healthy subject are denatured in denaturing solution (50% (v/v) formamide, 2.2 mol/L formaldehyde, 20 mmol/L MOPS (3-(N-morpholino)propanesulfonic acid) (pH 7.0), 5 mmol/L sodium acetate, 1 mmol/L EDTA) by heating at 65° C. for 5 minutes; and electrophoresis is performed using 1% agarose gel containing 2.2 mol/L formaldehyde.

After the electrophoresis, the RNAs in the gel are blotted onto a nitrocellulose filter (Optimal BA-S85; Schleicher & Schuell) and is immobilized by heating at 80° C. for 1 hour under reduced pressure.

Pre-hybridization is performed by soaking this filter in hybridization solution (5×SSPE (750 mmol/L NaCl, 50 mmol/L $NaH_2PO_4$, 5 mmol/L EDTA; pH 7.4), 5×Denhardt's solution (0.1% ficoll, 0.1% polyvinyl pyrrolidone, 0.1% bovine serum albumin, 1% SDS (sodium dodecyl sulfate), 0.2 mg/ml Salmon Sperm DNA (Pharmacia Biotech).

After the prehybridization, probes are added to the solution, and hybridization is performed at 65° C.

As a probe, for example, the DNA fragment of SEQ ID NO: 3 or the DNA fragment of SEQ ID NO: 4 that are labeled with $^{32}P$ using Multiprime DNA Labeling System (Amersham) can be used.

After hybridization, the filter is washed in the following order:
  (a) washing in 2×SSC solution (300 mmol/L NaCl, 30 mmol/L sodium citrate) containing 0.1% SDS at room temperature for 15 minutes, which is repeated several times;
  (b) washing in 1×SSC solution (150 mmol/L NaCl, 15 mmol/L sodium citrate) containing 0.1% SDS at 50 to 70° C. for 15 minutes, which is repeated several times; and
  (c) washing in 0.1×SSC solution (15 mmol/L NaCl, 1.5 mmol/L sodium citrate) containing 0.1% SDS at 50 to 70° C. for 15 minutes, which is repeated several times.

After washing the filter, expression of the DNA of SEQ ID NO: 3 or 4 can be detected and quantified with Bioimaging Analyzer BAS2000 (Fuji Photo Film) by performing autoradiography using an imaging plate.

Furthermore, the above-mentioned diseases can be detected, for example by performing PCR using a pair of oligonucleotides specific to a DNA encoding a protein of the present invention as a primer and cDNAs prepared from total RNAs derived from leukocytes or tissues of a test subject and a healthy subject, mRNAs thereof, or cDNAs prepared from these RNAs as templates; detecting and quantifying the amplified fragments; and comparing the expression levels of the DNAs of the test subject and the healthy subject.

The oligonucleotides of the present invention can be used as such oligonucleotides.

Total RNA or mRNA, which serves as a template for PCR, can be extracted from various leukocytes separated and obtained from blood or from tissues, such as tissues suspected of a disease.

Examples of leukocytes include polymorphonuclear leukocytes, monocytes, lymphocytes, T cells, B cells, and so on.

Polymorphonuclear leukocytes and mononuclear leukocytes can be separated and obtained from peripheral blood of a subject using Polymorphprep™, a kit manufactured by Nycomed Pharma.

From the obtained mononuclear leukocytes, monocytes and lymphocytes can be separated and obtained by methods according to J. Immunol., 130, 706 (1983), and the like. T cells and B cells can be separated and obtained by methods according to Tissue Antigen, 9, 153 (1977); J. Immunol., 11, 273 (1976); the instructions by Nycomed relating to isolation methods of blood cells, and the like.

T cells can be obtained using the nylon wool method (Eur. J. Immunol., 3, 645 (1973)). Alternatively, each of the cells can be separated and obtained using magnetic beads (for example Dynabeads from Dynal) bound to antibodies specific to T cells, B cells, and monocytes/macrophage, respectively.

Examples of methods for preparing total RNA from leukocytes or tissues include the guanidine thiocyanate-cesium trifluoroacetate method (Methods in Enzymol., 154, 3 (1987)), and the like.

Examples of methods for preparing poly(A)+ RNA from total RNA include the oligo(dT)-immobilized cellulose column method (Molecular Cloning, 2nd edition), and the like.

Furthermore, mRNA can be prepared using kits, such as Fast Track mRNA Isolation Kit (Invitrogen), and Quick Prep mRNA Purification Kit (Pharmacia).

Single-stranded cDNA can be synthesized from total RNA or mRNA using single-stranded cDNA synthesis kit, Superscript preamplification system (BRL). Synthesis can be performed according to the instructions attached to the kit.

The expression level of a gene encoding the protein of the present invention can be quantified by RT-PCR method (PCR Protocols, Academic Press (1990)) using total RNA, mRNA, or cDNA that can be prepared as mentioned above.

(2) Method for Detecting Diseases by Detecting Mutations of a Gene Encoding a Protein of the Present Invention Using the oligonucleotides of the present invention as a probe, mutations of a gene encoding a protein of the present invention can be detected by performing Southern hybridization method (Molecular Cloning, 2nd edition), PCR method, and the like on genomic DNA. The detection method can be used for detecting diseases that have been reported to be associated with a protein belonging to the IGFBP family including, for example, diseases accompanying abnormal cell growth, such as acute myelogenous leukemia, breast cancer, prostate cancer, colon cancer, hepatic cancer, myeloma, uterine leiomyoma, malignant tumor, and solid tumor; diseases accompanying angiopathy, such as myocardial infarction, cerebral infarction, peripheral vascular atresia, angina pectoris, hypertension, hyperlipidemia, diabetes, diabetic retinopathy, glomerulonephritis, arteriosclerosis, thrombosis, hemolytic uremic syndrome, thrombotic thrombocytopenic purpa, ischemic heart disease, ischemic encephalopathy, heart failure, hemostasis, and choroid circulatory dysfunction; diseases accompanying abnormal bone metabolism, such as osteoporosis; diseases accompanying disorders of insulin-like growth factors or growth hormone action, such as dwarfism, acromegaly, and infantile chronic renal failure; diseases accompanying abnormal differentiation or growth of smooth muscle cells, such as arteriosclerosis, bronchial disease, and restenosis; diseases accompanying abnormal differentiation or growth of skeletal muscle cells, such as myasthenia gravis; diseases accompanying abnormal gastric acid secretion, such as gastric ulcer; and inflammatory diseases accompanying abnormal lymphocyte invasion, such as microbial infection, chronic hepatitis B, chronic rheumatoid arthritis, sepsis, graft versus host disease, insulin dependent diabetes mellitus, nephritis, traumatic brain damage, inflammatory enteropathy, allergy, atopy, asthma, pollinosis, airway hypersensitivity, and autoimmune disease.

Specifically, the presence or absence of mutations in the coding region can be determined, for example, by amplifying the coding region of a DNA encoding a protein of the present invention carried by a patient by PCR method, determining the nucleotide sequence, and comparing the nucleotide sequence to the DNA carried by a healthy subject.

The cDNA that serves as the template for the PCR method can be obtained by the method of (1). The nucleotide sequence of the obtained cDNA can be determined using DNA Sequencer 377 from Perkin Elmer and reaction kit (ABI Prism™ BigDye™ Terminator Cycle Sequencing Ready Reaction kit: Applied Biosystems).

(3) Method for Detecting Diseases by Immunological Detection Method and Quantitative Determination Method Using an antibody of the present invention, diseases mentioned below can be detected by immunologically detecting or quantitatively determining the expression of a protein of the present invention in blood or tissues of a test subject and a healthy subject, and then comparing the results between the test subject and the healthy subject.

Examples of methods for immunological detection are ELISA method using microtiter plates, fluorescent antibody method, Western Blotting method, immunohistological staining method, and the like.

Examples of methods for immunological quantitative determination are the sandwich ELISA method using two types of monoclonal antibodies having different epitopes from among antibodies reacting with a protein of the present invention in a liquid phase; the radioimmunoassay method using a protein of the present invention labeled with a radioisotope, such as $^{125}$I, and antibodies recognizing this protein; and the like.

The immunological methods can be used for detecting diseases reported to be associated with a protein belonging to the IGFBP family including, for example, diseases accompanying abnormal cell growth, such as acute myelogenous leukemia, breast cancer, prostate cancer, colon cancer, hepatic cancer, myeloma, uterine leiomyoma, malignant tumor, and solid tumor; diseases accompanying angiopathy, such as myocardial infarction, cerebral infarction, peripheral vascular atresia, angina pectoris, hypertension, hyperlipidemia, diabetes, diabetic retinopathy, glomerulonephritis, arteriosclerosis, thrombosis, hemolytic uremic syndrome, thrombotic thrombocytopenic purpa, ischemic heart disease, ischemic encephalopathy, heart failure, hemostasis, and choroid circulatory dysfunction; diseases accompanying abnormal bone metabolism, such as osteoporosis; diseases accompanying disorders of insulin-like growth factors or growth hormone action, such as dwarfism, acromegaly, and infantile chronic renal failure; diseases accompanying abnormal differentiation or growth of smooth muscle cells, such as arteriosclerosis, bronchial disease, and restenosis; diseases accompanying abnormal differentiation or growth of skeletal muscle cells, such as myasthenia gravis; diseases accompanying abnormal gastric acid secretion, such as gastric ulcer; and inflammatory diseases accompanying abnormal lymphocyte invasion, such as microbial infection, chronic hepatitis B, chronic rheumatoid arthritis, sepsis, graft versus host disease, insulin dependent diabetes mellitus, nephritis, traumatic brain damage, inflammatory enteropathy, allergy, atopy, asthma, pollinosis, airway hypersensitivity, and autoimmune disease.

Furthermore, using antibodies that specifically bind to the protein consisting of the amino acid sequence shown in SEQ ID NO: 1 and antibodies that specifically bind to the protein consisting of the amino acid sequence shown in SEQ ID NO: 2, diseases characterized by differences in the expression ratios of these proteins can be determined from the above-mentioned diseases by the above-mentioned immunological methods.

(4) Method for Detecting Diseases by Analyzing the Expression Pattern of a DNA or a Protein of the Present Invention By quantitatively determining and comparing the expression levels of a DNA encoding a protein comprising the amino acid sequence shown in SEQ ID NO: 1 and a DNA encoding a protein comprising the amino acid sequence shown in SEQ ID NO: 2 in blood or tissue of a test subject and a healthy subject using any one of the method of the above-mentioned (1) to (3) for quantitatively measuring the expression levels of the DNA or the protein of the present invention, diseases characterized by a different expression level ratio of the DNAs or the proteins between the test subject and the healthy subject can be determined.

The detection methods as described above can be used for detecting diseases reported to be associated with proteins belonging to the IGFBP family including, for example, diseases accompanying abnormal cell growth, such as acute myelogenous leukemia, breast cancer, prostate cancer, colon cancer, hepatic cancer, myeloma, uterine leiomyoma, malignant tumor, and solid tumor; diseases accompanying angiopathy, such as myocardial infarction, cerebral infarction, peripheral vascular atresia, angina pectoris, hypertension, hyperlipidemia, diabetes, diabetic retinopathy, glomerulonephritis, arteriosclerosis, thrombosis, hemolytic uremic syndrome, thrombotic thrombocytopenic purpa, ischemic heart disease, ischemic encephalopathy, heart failure, hemostasis, and choroid circulatory dysfunction; diseases accompanying abnormal bone metabolism, such as osteoporosis; diseases accompanying disorders of insulin-like growth factors or growth hormone action, such as dwarfism, acromegaly, and infantile chronic renal failure; diseases accompanying abnormal differentiation or growth of smooth muscle cells, such as arteriosclerosis, bronchial disease, and restenosis; diseases accompanying abnormal differentiation or growth of skeletal muscle cells, such as myasthenia gravis; diseases accompanying abnormal gastric acid secretion, such as gastric ulcer;

and inflammatory diseases accompanying abnormal lymphocyte invasion, such as microbial infection, chronic hepatitis B, chronic rheumatoid arthritis, sepsis, graft versus host disease, insulin dependent diabetes mellitus, nephritis, traumatic brain damage, inflammatory enteropathy, allergy, atopy, asthma, pollinosis, airway hypersensitivity, and autoimmune disease.

(5) Prevention and Treatment of Diseases by Suppressing Transcription or Translation of DNAs Encoding a Protein of the Present Invention Regarding the relationship between the rise in the expression level of IGFBP and diseases, reports have been made that report the increases in IGFBP-2 and 3 as the cause of infantile chronic renal failure (Electroiyte Mrtab., 18, 320 (1992)); the rise in IGFBP-4 expression of women fracture patients of old age accompanying rise in parathyroid hormone; the rise in IGFBP-7 and IGFBP-3 concentrations in the cerebrospinal fluid of leukemia patients (J. Clin. Endocrinol. Metab., 84, 1361 (1996)); in colon cancer, the rise in IGFBP-7 expression in colon cancer tissues and in colon cancer cell lines (J. Gastroenterology, 33, 213 (1998)); and the like.

Furthermore, IGFBP-7 is also thought to be involved in diseases relating to bone metabolism and skeletal muscle differentiation due to the facts that IGFBP-7 expression rises in relation to TGF-β and PTHPGE2 (Endocrinology, 140, 1998 (1999)); that the expression of IGF-I is suppressed while IGFBP-7 expression is raised upon treatment of osteoblasts with glucocorticoids (Endocrinology, 140, 228 (1999)); and that IGFBP-7 has an effect on differentiation into skeletal muscles by suppressing the differentiation promoting action of IGF (Exp. Cell Res., 237, 192 (1997), Endocrinology, 141, 100 (2000)).

Therefore, lowering the level of transcription or translation of DNAs encoding a protein of the present invention is useful for prevention and treatment of diseases wherein the increase in the expression level of an IGFBP gene, or enhancement of IGFBP function is one of the causes. Furthermore, even in diseases that are not directly caused by IGFBP, the above-mentioned diseases can be prevented or treated by symptomatic treatment by lowering the level of transcription or translation of genes encoding a protein of the present invention, or by suppressing the function of the protein of the present invention.

Furthermore, a patient whose physiological action via receptors are enhanced due to the increase of IGFBP expression, the physiological action can be suppressed by administering a DNA, oligonucleotide, or derivative thereof of the present invention to the patient. Moreover, even if the increase in IGFBP expression is not the direct cause of the disease, the DNAs, oligonucleotides, or derivatives thereof of the present invention can function as effective preventive agents and therapeutic agents against diseases that are treatable by symptomatic treatment wherein the DNAs, oligonucleotides, or derivatives thereof of the present invention are administered.

Methods for using the preventive agents or therapeutic agents include, for example, antisense RNA/DNA techniques (Bioscience and Industry, 50, 322 (1992); Kagaku, 46, 681 (1991); Biotechnology, 9, 358 (1992); Trends in Biotechnology, 10, 87 (1992); Trends in Biotechnology 10, 152 (1992); Saibo Kogaku 16, 1463 (1997)); triple helix techniques (Trends in Biotechnology, 10, 132 (1992)); ribozyme techniques (Current Opinion in Chemical Biology, 3, 274 (1999); FEMS Microbiology Reviews, 23, 257 (1999); Frontiers in Bioscience, 4, D497 (1999); Chemistry & Biology, 6, R33 (1999); Nucleic Acids Research, 26, 5237 (1998); Trends In Biotechnology, 16, 438 (1998)); and decoy DNA methods (Nippon Rinsho—Japanese Journal of Clinical Medicine, 56, 563 (1998); Circulation Research, 82, 1023 (1998); Experimental Nephrology, 5, 429 (1997); Nippon Rinsho—Japanese Journal of Clinical Medicine, 54, 2583 (1996)). Using these methods, the expression of an arbitrary gene can be suppressed.

When using the DNAs, oligonucleotides, or derivatives thereof of the present invention as the above-mentioned preventive agents and therapeutic agents, the DNAs, oligonucleotides, or derivatives thereof of the present invention themselves or those inserted into appropriate vectors, such as retrovirus vector, adenovirus vector, and adenovirus-associated virus vector, can be made into formulations; prescribed; and administered according to conventional methods mentioned below.

A vector for gene therapy inserted into virus vectors, such as retroviruses and adenoviruses, or other vectors for gene therapy, which is used as an agent or preventive agent for gene therapy, can be produced by formulating the vector for gene therapy and a base agent for gene therapy (Nature Genet., 8, 42 (1994)).

Any base agent can be used for gene therapy so long as it can be used for conventional injections, and includes, for example, distilled water; salt solutions, such as sodium chloride and a mixture of sodium chloride and inorganic salts; sugar solutions of mannitol, lactose, dextran, glucose, etc.; amino acid solutions of glycine, arginine, etc.; mixed solutions comprising organic acid solution or salt solution, and glucose solution. In addition, according to conventional methods, the injection can be prepared as solutions, suspensions, or dispersion solutions using, in addition to the base, auxiliary agents, such as agents for osmoregulation; agents for pH adjustment; vegetable oils, such as sesame oil and soybean oil; or surfactants, such as lecithin or non-ionic surfactants. By operations such as powderization and freeze-drying, these injections can be prepared as formulations to be dissolved just before use. An agent for gene therapy of the present invention in the form of liquid can be directly used for treatment, and those in a solid form by dissolving just before use for gene therapy into the above-mentioned base that is sterilized as necessary. Methods for administration of an agent for gene therapy of the present invention include a method for local administration so that the agent is absorbed into the site to be treated within the patient.

Alternatively, a DNA can be transported to the desired site of treatment by non-viral gene transfection methods.

Examples of non-viral gene transfection methods well known in the art are the calcium phosphate precipitation method (Virology, 52, 456-467 (1973); Science, 209, 1414-1422 (1980)), the microinjection method (Proc. Natl. Acad. Sci. USA, 77, 5399-5403 (1980); Proc. Natl. Acad. Sci. USA, 77, 7380-7384 (1980); Cell, 27, 223-231 (1981); Nature, 294, 92-94 (1981)), the liposome mediated membrane fusion-mediated transfection method (Proc. Natl. Acad. Sci. USA, 84, 7413-7417 (1987); Biochemistry, 28, 9508-9514 (1989); J. Biol. Chem., 264, 12126-12129 (1989); Hum. Gene Ther., 3, 267-275, (1992); Science, 249, 1285-1288 (1990); Circulation, 83, 2007-2011 (1992)), and the direct DNA import and receptor-mediated DNA transfection method (Science, 247, 1465-1468 (1990); J. Biol. Chem., 266, 14338-14342 (1991); Proc. Natl. Acad. Sci. USA, 87, 3655-3659 (1991); J. Biol. Chem., 264, 16985-16987 (1989); BioTechniques, 11, 474-485 (1991); Proc. Natl. Acad. Sci. USA, 87, 3410-3414 (1990); Proc. Natl. Acad. Sci. USA, 88, 4255-4259 (1991);

Proc. Natl. Acad. Sci. USA, 87, 4033-4037 (1990); Proc. Natl. Acad. Sci. USA, 88, 8850-8854 (1991); Hum. Gene Ther., 3, 147-154 (1991)).

It has been reported in studies regarding tumors, that the liposome mediated membrane fusion-mediated transfection method enables localized import and expression of genes in the target tissues by direct administration of liposome preparations to the target tissue (Hum. Gene Ther., 3, 399 (1992)).

(6) Prevention and Treatment of Diseases with Decreased Expression Level or Function of a Protein of the Present Invention Regarding the relationship between diseases and decreased expression of IGFBP, it has been reported that IGFBP-5 expression is decreased in osteoporosis; increase of free IGF-I accompanying lowered IGFBP-3 expression is observed in compensatory hypertrophy after nephrectomy and small intestine resection (Baillieres Clin. Endocrinol. Metab., 8, 165 (1994)); IGFBP-1 expression is decreased in malignant tumors of the endometrium (Growth Regul., 3, 74 (1993)); LOH is observed at a frequency of 50% or more at the gene loci of IGFBP-7 on the human chromosome and IGFBP-7 expression is found to be decreased in breast cancer tissues (Oncogene, 16, 2459 (1996)); IGFBP-7 expression is decreased at the mRNA level in prostate cancer tissues, and IGFBP-7 expression is not detected in malignant prostate cancer-derived cell lines (J. Clin. Endocrinol. Metab., 83, 4355 (1998)); expression of mRNA of IGFBP-7 is lowered in large uterine leiomyoma sites compared to neighboring uterine smooth muscle cells and small uterine smooth muscles wherein the tumor volume is 120 $cm^3$ or less (Am. J. Reprod. Immunol., 43, 53 (2000)); the 5' upstream region of the IGFBP-7 gene is methylated, and its expression level is decreased in mouse hepatic cancer cells induced by SV40T antigen (Biochem. Biophys. Res. Commun., 267, 109 (2000)); IGFBP-7 expression is decreased in kidney and at sites of angiopathy in type I diabetes model due to the administration of streptozotocin (Diabetes, 45, S111 (1996); J. Diabetes & its Complications, 12, 252 (1998)); lowered IGFBP-7 expression is observed at the protein level in coronary artery smooth muscle cells of type II diabetes patients (Diabetes, 46, 1627 (1997)); the expression level of IGFBP-7 is decreased at the mRNA and protein levels when bovine artery-derived smooth muscle cells are cultivated in a glucose-rich medium (Diabetes, 46, 1627 (1997), Diabetologia, 41, 134 (1998)); IGFBP-7 stimulates PGI2 production in vascular wall (Nature, 271, 549 (1978)); and that the level of IGFBP in blood is decreased in hemolytic uremic syndrome (Lancet, 2, 871 (1978)), thrombotic thrombocytopenic purpa (Lancet, 2, 748 (1979)), sickle cell anemia (Br. J. Haematol., 48, 545 (1981)), acute myocardial infarction (Coronary, 2, 49 (1985)), diabetic angiopathy (Metabolism, 38, 837 (1989); Haemostasis, 16, 447 (1986); Diab. Res. Clin. Pract., 3, 243 (1987)), and arteriosclerosis.

Furthermore, IGFBP-7 is also considered to be involved with diseases relating to bone metabolism and skeletal muscle differentiation, due to the facts that IGFBP-7 expression rises in accordance to TGF-β and PTHPGE2 (Endocrinology, 140, 1998 (1999)), that IGF-I expression is suppressed while IGFBP-7 expression is raised upon treatment of osteoblasts with glucocorticoids (Endocrinology, 140, 228 (1999)), and that IGFBP-7 affects differentiation into skeletal muscles by suppressing the differentiation-promoting action of IGF (Exp. Cell Res., 237, 192 (1997); Endocrinology, 141, 100 (2000)).

Due to the elongation of cell division time, decrease in colony forming ability in soft agar medium, decrease of the tumor forming ability in nude mouse transplantation, and elevation of apoptosis induction rate by drug treatment occurring by the forced expression of IGFBP-7 in prostate cancer cell lines with decreased IGFBP-7 expression (Cancer Res., 59, 2370 (1999)); and due to the fact that the forced expression of IGFBP-7 in osteosarcoma cell lines, whose p53 function is lost, leads to the suppression of proliferation of the cell lines similarly to the transfection of the p53 gene (Oncogene, 12, 1361 (1996)), the above-mentioned diseases associated with decreased IGFBP expression can be prevented or treated by increasing the expression of a DNA and protein of the present invention. Furthermore, even for diseases that are not directly caused by IGFBP, the above-mentioned diseases for which symptomatic treatment is possible can be prevented or treated by increasing the level of transcription or translation of a gene encoding a protein of the present invention, or by increasing the amount of a protein of the present invention.

Therefore, the physiological action of a patient with decreased physiological action of a protein of the present invention due to the decreased expression or function of IGFBP can be promoted by administering a DNA, oligonucleotide or its derivative of the present invention or a protein of the present invention to the patient. Furthermore, the DNAs, oligonucleotides, or derivatives thereof of the present invention, or proteins of the present invention are useful as preventive agents and therapeutic agents against the above-mentioned diseases for which symptomatic treatment is possible, even if the decreased expression or function of IGFBP is not the direct cause of the disease.

As methods of administration of preventive agents and therapeutic agents, for example, a patient with decreased expression or mutation of a protein of the present invention for whom normal physiological action of the protein cannot be expected can be treated by (i) administering a DNA encoding the protein of the present invention to the patient and expressing the DNA; (ii) inserting a DNA encoding the protein of the present invention into target cells, expressing the DNA, and then transplanting the cells to the patient; or (iii) administering the protein of the present invention to the patient, to increase the amount of the protein of the present invention in the patient and let sufficiently exert the physiological function of the protein. Therefore, the DNAs encoding the proteins of the present invention or the proteins of the present invention are useful as safe preventive and therapeutic agents with low toxicity against diseases associated with decreased expression level or function of a protein of the present invention, diseases that result from functional abnormality due to mutations of this protein, or diseases that are not directly caused by the protein of the present invention but can be treated by symptomatic treatment by the administration of the protein or a DNA encoding the protein of the present invention.

To use a DNA encoding a protein of the present invention as the above-mentioned preventive agents and therapeutic agents, the DNA of the present invention alone or the DNA inserted into appropriate vectors, such as retrovirus vector, adenovirus vector, and adenovirus associated virus vector, can be formulated, prescribed, and administered following the conventional methods of (5) mentioned above.

In addition, medicaments containing a protein of the present invention as their active ingredient can be administered as the active ingredient alone, but ordinarily, they are mixed with one or more pharmacologically acceptable carriers, and are preferably provided as a medical preparation produced by arbitrary methods well known in the art of pharmaceutical technology. Preferably, water, or sterilized solutions dissolved in water-based carriers, such as aqueous solutions of sodium chloride, glycine, glucose, and human albumin, are used. Pharmacologically acceptable additives, such as buffer agents and isotonic agents may be added to provide a physiological condition for the pharmaceutical solution, including sodium acetate, sodium chloride, sodium lactate, potassium chloride, sodium citrate, and so on. Furthermore, the medicament can be stored after freeze-drying and can be used upon dissolving in an appropriate solvent at the time of use.

The most effective administration route is preferably adopted for treatment, and includes oral administration or parenternal administration, such as oral, tracheobronchial, endorectal, subcutaneous, intramuscular, or intravenous administration. Examples of administration forms are propellants, encapsulated formulations, tablets, granules, syrups, emulsions, suppositories, injections, ointments, tapes, and the like.

Pharmaceutical preparations suitable for oral administration are emulsions, syrups, encapsulated formulations, tablets, powders, granules, and the like. For example, liquid preparations such as emulsions and syrups can be produced using water; sugars, such as sucrose, sorbitol, and fructose; glycols, such as polyethylene glycol and propylene glycol; oils, such as sesame oil, olive oil, and soybean oil; preservatives, such as p-hydroxybenzoic acid esters; flavors, such as strawberry flavor and peppermint; and the like, as additives. Encapsulated formulations, tablets, powders, granules, and the like can be produced using additives including excipients, such as lactose, glucose, sucrose, and mannitol; disintegrators, such as starch and sodium alginate; lubricants, such as magnesium stearate and talc; binders, such as polyvinyl alcohol, hydroxypropyl cellulose, and gelatin; surfactants, such as fatty acid esters; plasticizers, such as glycerin.

Examples of pharmaceutical preparations suitable for parenternal administration are injections, suppositories, propellant, and the like. For example, injections are prepared using carriers and the like comprising salt solutions, glucose solutions, or mixtures of both. Suppositories are prepared using carriers such as cacao butter, hydrogenated fat, or carboxylic acids. Furthermore, propellants are prepared using a protein of the present invention itself, or with carriers that do not stimulate the oral and respiratory tract mucosa of the recipient and which facilitate the absorbance by dispersing the protein as fine particles. More specifically, examples of carriers are lactose, glycerin, and the like. Depending on the characteristic of the used protein and the carriers, pharmaceutical preparations such as aerosols and dry powders are possible. In addition, components cited as examples of additives for oral agents may be added to these parenternal agents.

Although the dose or frequency of administration varies depending on the desired therapeutic effect, administration method, therapeutic duration, age, weight, and the like, it is usually 10 μg/kg to 8 mg/kg per day for an adult.

(7) Methods for Obtaining the Promoter Regions of the Genes Encoding the Proteins of the Present Invention Using the DNAs or oligonucleotides of the present invention as a probe, the promoter regions of the genes can be obtained using known methods (New Cell Engineering Experiment Protocols, University of Tokyo Institute of Medical Science Division of Anti-Cancer Research edition, Shujun-sha (1993)).

The promoter regions include all promoter regions involved in the transcription of the genes encoding the proteins of the present invention in mammalian cells. Such examples are the promoter regions involved in the transcription of a gene encoding a protein of the present invention in the small intestine of human. The promoters can be used for methods of screening for substances that regulate the transcription or translation of the DNAs encoding the proteins of the present invention, which will be mentioned below in (8).

(8) Methods of Screening for Substances that Regulate the Transcription or Translation of the Genes Encoding the Proteins of the Present Invention Proteins belonging to the IGFBP superfamily have been reported to be associated with diseases, for example, diseases accompanying abnormal cell growth, such as acute myelogenous leukemia, breast cancer, prostate cancer, colon cancer, hepatic cancer, myeloma, uterine leiomyoma, malignant tumor, and solid tumor; diseases accompanying angiopathy, such as myocardial infarction, cerebral infarction, peripheral vascular atresia, angina pectoris, hypertension, hyperlipidemia, diabetes, diabetic retinopathy, glomerulonephritis, arteriosclerosis, thrombosis, hemolytic uremic syndrome, thrombotic thrombocytopenic purpa, ischemic heart disease, ischemic encephalopathy, heart failure, hemostasis, and choroid circulatory dysfunction; diseases accompanying abnormal bone metabolism, such as osteoporosis; diseases accompanying disorders of insulin-like growth factors or growth hormone action, such as dwarfism, acromegaly, and infantile chronic renal failure; diseases accompanying abnormal differentiation or growth of smooth muscle cells, such as arteriosclerosis, bronchial disease, and restenosis; diseases accompanying abnormal differentiation or growth of skeletal muscle cells, such as myasthenia gravis; diseases accompanying abnormal gastric acid secretion such as gastric ulcer; and inflammatory diseases accompanying abnormal lymphocyte invasion, such as microbial infection, chronic hepatitis B, chronic rheumatoid arthritis, sepsis, graft versus host disease, insulin dependent diabetes mellitus, nephritis, traumatic brain damage, inflammatory enteropathy, allergy, atopy, asthma, pollinosis, airway hypersensitivity, and autoimmune disease.

Changes in the transcription level of DNAs encoding IGFBPs or functional changes of the proteins of the present invention can be considered as a factor for the above-mentioned diseases. In this case, regulation of the level of transcription or translation of the DNAs encoding the proteins of the present invention is effective for the prevention and treatment of such diseases. Diseases that are not directly caused by IGFBP can be also prevented or treated by symptomatic treatment of the above-mentioned diseases by regulating the level of transcription or translation of the genes encoding the proteins of the present invention.

Therefore, compounds that promote or suppress the process of transcription of the genes encoding the proteins of the present invention, or the process of translation from the transcription products to the proteins can regulate the cell functions exerted through the proteins by regulating the expression of the proteins, and is useful as safe pharmaceutical compositions with low toxicity.

The compounds can be obtained by the following methods of (a) to (c):

(a) A method for selecting and obtaining compounds that have the activity to increase or decrease the amount of a protein of the present invention by [i] culturing cells expressing the protein, or [ii] culturing cells expressing the protein in the presence of a test substance for 2 hours to 1 week by the culturing method of the above-mentioned 2, and then measuring and comparing the amount of the protein in the cells using the antibodies of the present invention according to (3) mentioned above.

Examples of the methods for measurement using the antibodies of the present invention include ELISA method using microtiter plates, fluorescent antibody method, Western Blotting method, detection methods utilizing immunohistological staining method, and the like.

(b) A method for selecting and obtaining compounds that have the activity to increase or decrease the amount of a transcription product of DNA encoding a protein of the present invention by [i] culturing cells expressing the protein or [ii] culturing cells expressing the protein in the presence of a test substance for 2 hours to 1 week by the above-mentioned cultivation method of 2, and then measuring and comparing the amount of transcription product of the DNA encoding the protein in the cell using methods such as the Northern hybridization method or PCR method mentioned in above (1).

(c) First, a plasmid containing DNA wherein a reporter gene is connected downstream of a promoter obtained in the above-mentioned (7) by conventional methods, and then the plasmid is inserted into animal cells according to the above-mentioned method of 2 to obtain a transformant. A method for selecting and obtaining compounds that have the activity to increase or decrease the expression level of the reporter gene by [i] culturing the transformant or [ii] culturing the transformant in the presence of a test substance for 2 hours to 1 week by the above-mentioned culturing method of 2, and then measuring and comparing the expression level of the reporter gene in the cell by conventional methods ("Shin Saibokogaku Jikken Purotokoru (New Cell Engineering Experiment Protocols)", University of Tokyo Institute of Medical Science Division of Anti-Cancer Research edition, Shujun-sha (1993); Biotechniques, 20, 914 (1996); J. Antibiotics, 49, 453 (1996); Trends in Biochemical Sciences, 20, 448 (1995); Saibo Kogaku (Cell Engineering), 16, 581 (1997)).

Examples of reporter genes are, chloramphenicol acetyltransferase gene, β-galactosidase gene, β-lactamase gene, luciferase gene, green fluorescent protein (GFP) gene, and the like.

(9) Methods of Screening for Substances that Regulate the Function of the Proteins of the Present Invention Proteins belonging to the IGFBP superfamily have been reported to be associated with diseases, for example, diseases accompanying abnormal cell growth, such as acute myelogenous leukemia, breast cancer, prostate cancer, colon cancer, hepatic cancer, myeloma, uterine leiomyoma, malignant tumor, and solid tumor; diseases accompanying angiopathy, such as myocardial infarction, cerebral infarction, peripheral vascular atresia, angina pectoris, hypertension, hyperlipidemia, diabetes, diabetic retinopathy, glomerulonephritis, arteriosclerosis, thrombosis, hemolytic uremic syndrome, thrombotic thrombocytopenic purpa, ischemic heart disease, ischemic encephalopathy, heart failure, hemostasis, and choroid circulatory dysfunction; diseases accompanying abnormal bone metabolism, such as osteoporosis; diseases accompanying disorders of insulin-like growth factors or growth hormone action, such as dwarfism, acromegaly, and infantile chronic renal failure; diseases accompanying abnormal differentiation or growth of smooth muscle cells, such as arteriosclerosis, bronchial disease, and restenosis; diseases accompanying abnormal differentiation or growth of skeletal muscle cells, such as myasthenia gravis; diseases accompanying abnormal gastric acid secretion, such as gastric ulcer; and inflammatory diseases accompanying abnormal lymphocyte invasion, such as microbial infection, chronic hepatitis B, chronic rheumatoid arthritis, sepsis, graft versus host disease, insulin dependent diabetes mellitus, nephritis, traumatic brain damage, inflammatory enteropathy, allergy, atopy, asthma, pollinosis, airway hypersensitivity, and autoimmune disease.

Change in the function of IGFBP is thought to be a cause of the above-mentioned diseases, and in such a case, inhibition or enhancement of the function of a protein of the present invention is effective for preventing and treating the diseases. Furthermore, even for diseases that are not directly caused by IGFBPs, the above-mentioned diseases can be prevented or treated by symptomatic treatment by inhibiting or enhancing the function of a protein of the present invention.

Therefore, a patient whose physiological action of cells is decreased or enhanced due to the change in the function of a protein of the present invention, the physiological action can be regulated by administering a compound of the present invention that regulate the function. Furthermore, even if the change in the function of a protein of the present invention is not the direct cause of a disease, diseases for which symptomatic treatment is possible by regulating the function of a protein of the present invention can also be prevented or treated by administering the compound.

Such compounds can be obtained, for example, by the following methods:

a method for selecting and obtaining compounds that have the activity to inhibit or enhance the function of a protein of the present invention by culturing [i] cells that express the protein and [ii] in the presence of a test substance for 2 hours to 1 week by the above-mentioned culturing method of 2, and then detecting and comparing cellular responses caused by the fact that the protein has functioned.

Methods for detecting cellular responses that occur due to the function of a protein of the present invention are, for example, conventional methods for detecting changes of intracellular information transfer, transcription of genes, uptake of sugars, or growth that is dependent on insulin or insulin-like growth factors contained in a culture medium. Further examples are conventional methods for measuring changes in prostaglandin production (Nature, 263, 663, (1976); Rinsho Kagaku (Clinical Science), 17, 958, (1981)).

(10) Methods of Screening for Substances that Specifically Bind to a Protein of the Present Invention Substances that specifically bind to a protein of the present invention can be used to develop preventive agents or therapeutic agents for diseases caused by the protein of the present invention. A receptor of a protein of the present invention binds to the protein of the present invention, and has the function to transmit information into cells and exerts physiological action. Therefore, similarly to substances regulating the proteins of the present invention, or transcription or translation of genes encoding the proteins of the present invention, for example, substances regulating the activity of the receptor, or the transcription or translation of genes encoding the receptor are useful as preventive agents and therapeutic agents for diseases caused by functional abnormality of the protein of the present invention. Examples of these substances are low-molecular-weight compounds, proteins, and the like.

Methods for screening proteins that specifically bind to a protein of the present invention are, for example, methods for expression cloning according to Molecular Cloning, 2nd edition; Current Protocols in Molecular Biology; Science, 255, 989 (1992); and the like. A protein specifically binding to the protein of the present invention can be obtained by selecting, from test samples, proteins that bind to the protein of the present invention when the protein and the test sample are brought in contact.

Specifically, the following methods can be mentioned.

cDNAs are prepared from tissues. Recombinant vectors are constructed by inserting each of the cDNAs downstream of a promoter in an appropriate expression vector to prepare a cDNA library. Transformants expressing one of the genes expressed in the tissues are obtained by transfecting the recombinant vectors into host cells suitable for the expression vector. Transformants that produce proteins that specifically bind to a labeled protein of the present invention are selected.

Proteins that specifically bind to the protein of the present invention can be obtained by determining the genetic sequence encoded by the cDNA introduced into the selected transformant.

Examples of methods for preparing a cDNA library include the above-mentioned methods of 1.

Methods for introducing recombinant vectors, methods for obtaining transformants, and methods for culturing the obtained transformants in a medium are exemplified by the above-mentioned methods of 2.

By co-culturing the transformant and a protein of the present invention that is labeled by a conventional method for labeling proteins, such as radioactive isotope labeling and biotinylation, transformants producing gene products that specifically bind to the labeled protein of the present invention can be selected.

Examples of methods for isolating cDNAs introduced to the selected transformants include the Hirt method or methods for collecting phage vectors and plasmid vectors according to Molecular Cloning, 2nd edition; Current Protocols in Molecular Biology; Mol. Cell. Biol., 8, 2837 (1988); and the like.

Examples of methods for determining the genetic sequences of the isolated cDNAs include the above-mentioned methods of 1.

(11) Medicaments Containing Antibodies of the Present Invention

The antibodies of the present invention are useful as preventive agents and therapeutic agents of diseases relating to a protein of the present invention.

Regarding the relationship between the rise in the expression level of IGFBPs and diseases, it has been reported that increase in IGFBP-2 and 3 is the cause of infantile chronic renal failure (Electroiyte Mrtab., 18, 320 (1992)); IGFBP-4 expression rises in women fracture patients of old age accompanying rise in parathyroid hormone; IGFBP-7 and IGFBP-3 concentrations in cerebrospinal fluid rise in leukemia patients (J. Clin. Endocrinol. Metab., 84, 1361 (1996)); in colon cancer, IGFBP-7 expression rises in colon cancer tissues and in colon cancer cell lines (J. Gastroenterology, 33, 213 (1998)); and the like.

Furthermore, IGFBP-7 is thought to be also involved in diseases relating to bone metabolism and skeletal muscle differentiation due to the facts that IGFBP-7 expression rises in response to TGF-β, PTH, and PGE2 (Endocrinology, 140, 1998 (1999)); that IGF-I expression is suppressed while IGFBP-7 expression is raised upon treatment of osteoblasts with glucocorticoids (Endocrinology, 140, 228 (1999)); and that IGFBP-7 has an effect on differentiation into skeletal muscles by suppressing the differentiation promoting action of IGF (Exp. Cell Res., 237, 192 (1997), Endocrinology, 141, 100 (2000)).

Therefore, regarding diseases wherein the increase in the expression level or enhancement of the function of IGFBP is one of the causes, suppressing the expression levels or inhibiting the function of a protein of the present invention is effective for prevention and treatment of the diseases. Even in diseases that are not directly caused by IGFBPs, the above-mentioned diseases for which symptomatic treatments are possible can be prevented or treated by suppressing the expression level or by inhibiting the function of the protein of the present invention.

Accordingly, a patient with enhanced physiological action of cells due to the increase in the expression level or functional enhancement of IGFBPs, the physiological action can be suppressed by administering an antibody that binds to a protein of the present invention. Furthermore, even when the proteins of the present invention are not the direct cause of the diseases, by suppressing the function of the proteins of the present invention, diseases for which symptomatic treatments are possible can be prevented and treated by administering an antibody of the present invention.

Medicaments containing an antibody as an active ingredient can be provided as pharmaceutical preparations produced by arbitrary methods well known in the art of pharmacological technology, following the above-mentioned methods for producing medicaments containing a protein of the present invention according to (6).

(12) Medicaments Containing a Compound Obtained by the Screening Method of (8)

Compounds that promote or suppress the process of transcription of a gene encoding a protein of the present invention, or the process of translation from a transcription product to the protein are useful as safe pharmaceutical compositions having low toxicity.

Compounds obtained in (8) can be provided as pharmaceutical preparations produced by arbitrary methods well known in the art of pharmacological technology, following the methods for producing medicaments containing a protein of the present invention according to (6).

(13) Production of Non-Human Knockout Animals Using a DNA of the Present Invention Using recombinant vectors comprising a DNA of the present invention, mutant clones, wherein a gene on chromosome encoding a protein of the present invention is inactivated or substituted with an arbitrary sequence by known methods for homologous recombination (for example, Nature 326, 6110, 295 (1987); Cell, 51, 3, 503 (1987)), are produced in embryonic stem cells of desired non-human animals, such as cattle, sheep, goat, pig, horse, mouse, and chicken (for example, Nature 350, 6315, 243 (1991)). Using a mutant clone of embryonic stem cell, a chimeric individual consisting of the embryonic stem cell clone and normal cell can be prepared by methods, such as the aggregation chimera method or the infusion chimera method against blastocysts of fertilized eggs of animals. By crossing the chimeric individual and a normal individual, individuals having an arbitrary mutation on the gene encoding the protein of the present invention located on chromosomes of all cells of the entire body can be obtained. Furthermore, a non-human knockout animal wherein the expression of the gene encoding the protein of the present invention is partially or completely suppressed can be obtained from homomeric individuals that have mutations on both of the homologous chromosomes by crossing such individuals.

Alternatively, non-human knockout animals can be produced by introducing mutations to arbitrary positions of a gene on chromosome encoding a protein of the present invention. For example, the activity of a gene product can be altered by introducing mutations by substitutions, deletions, insertions, and the like of bases in the coding region of the gene on chromosome encoding a protein of the present invention. Furthermore, the degree, timing, tissue specificity and the like, of the expression of the gene can be altered by introducing similar mutations to its expression regulatory region. Furthermore, combination with a Cre-loxP system enables a more active regulation of the timing of expression, expression site, expression level, and the like. An example, using a promoter expressed in a specific region of the brain, wherein a desired gene was deleted only in that region (Cell, 87, 7, 1317 (1996)), and an example wherein a desired gene was deleted organ-specifically at the desired timing using adenoviruses expressing Cre (Science, 278, 5335, (1997)) are known as such examples.

Therefore, for a gene on chromosome encoding a protein of the present invention, a non-human knockout animal wherein the expression is regulated at arbitrary timing and in arbitrary tissues in this manner, or have arbitrary insertions, deletions, and substitutions in their coding regions or expression regulatory regions can be produced.

The non-human knockout animals can induce symptoms of various diseases caused by the protein of the present invention at arbitrary timing, to arbitrary degrees, or at arbitrary sites.

Thus, the non-human knockout animals of the present invention serve as extremely useful animal models for the treatment and prevention of various diseases caused by the protein of the present invention. In particular, they are very useful as models for the evaluation of therapeutic agents and preventive agents against such diseases, as well as functional foods, health foods and the like.

BRIEF DESCRIPTION OF THE DRAWINGS

FIG. 1 shows the comparison of the amino acid sequences of C-hsi13412 and C-kaia397 (SEQ ID NO:35), and IGFBP family factors (SEQ ID NOS:28-34).

FIG. 11 shows the detection by Western Blotting of proteins encoded by C-hsi13412 or C-kaia397 using KM2961 and KM2962. Mock represents the control.

FIG. 13 shows the effect of the protein encoded by C-hsi13412 or C-kaia397 on IGF-dependent growth of HT-29 cells. Mock represents the control.

BEST MODE FOR CARRYING OUT THE INVENTION

Figure 2:
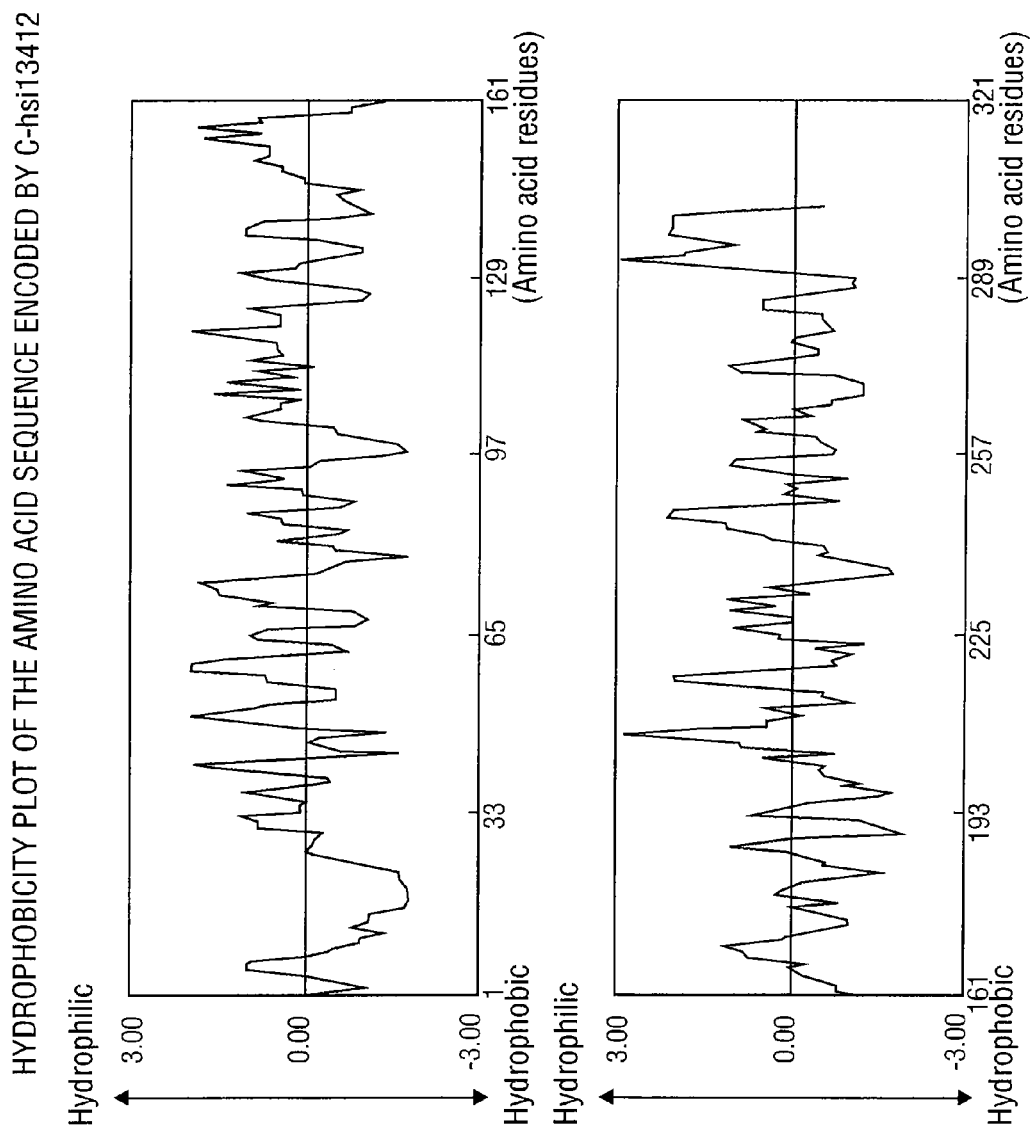
FIG. 2 shows the hydrophobicity plot of the protein encoded by C-hsi13412.

The present invention is illustrated in detail below with reference to Examples. However, these Examples are only provided for illustrations of the present invention, and the present invention should not to be construed as being limited thereto.

Example 1

Preparation of Human Small Intestinal Mucosal Tissue-Derived cDNA Library

According to the method described in Molecular Cloning, 2nd edition, mRNAs were extracted from human small intestinal mucosal tissues. Then, polyA(+)RNAs were purified using oligo dT cellulose. cDNA library was prepared by the oligo-capping method (Gene, 138, 171 (1994)) from the polyA(+)RNAs. Using oligo-cap linker (SEQ ID NO: 5) and oligo dT primer (SEQ ID NO: 6), BAP (Bacterial Alkaline Phosphatase) treatment, TAP (Tobacco Acid Phosphatase) treatment, RNA ligation, synthesis of primary strand cDNAs, and removal of RNAs were carried out according to the method described in the literatures (Protein, Nucleic Acid, and Enzyme, 41, 197 (1996); Gene, 200, 149 (1997)). Next, conversion to double-stranded cDNAs was carried out by PCR (polymerase chain reaction) using 5' end sense primer (SEQ ID NO: 7) and 3' end antisense primer (SEQ ID NO: 8) as PCR primers, and then the double stranded cDNAs were digested with SfiI. The PCR was carried out using a commercially available kit, Geneamp XL PCR kit (Perkin Elmer), by heating at 95° C. for 5 minutes, then repeating 12 reaction cycles of 95° C. for 1 minute, 58° C. for 1 minute, and 72° C. for 10 minutes, and then maintaining the temperature at 4° C. Then, recombinant DNAs were produced by linking the cDNAs in a fixed direction to pME18SFL3 vectors (GeneBank AB009864, Expression vector, 3392 bp) digested with DraIII, to prepare a cDNA library by transforming *Escherichia coli* DH5α with the recombinant DNAs. A sequencing reaction of the nucleotide sequences of the 5' end and 3' end of cDNAs of each plasmid DNA harbored by the obtained transformants was performed using DNA sequencing reagent (Dye Terminator Cycle Sequencing FS Ready Reaction Kit, dRhodamine Terminator Cycle Sequencing FS Ready Reaction Kit or BigDye Terminator Cycle Sequencing FS Ready Reaction Kit, PE Biosystems) according to the instructions, to determine its sequence with DNA sequencer (ABI PRISM 377, PE Biosystems).

Example 2

Identification of Novel Proteins Belonging to the IGFBP Superfamily

Using 10 molecules, human IGFBP-1, human IGFBP-2, human IGFBP-3, human IGFBP-4, human IGFBP-5, human IGFBP-6, human IGFBP-7, human IGFBP-8, human IGFBP-9, and human IGFBP-10 as known proteins that belong to the IGFBP superfamily, registered in protein amino acid database SWISSPROT or nucleotide sequence database GenBank, 2 types of clones, C-hsi13412 and C-kaia397, having amino acid sequence homology to these molecules were selected from the nucleotide sequences of each clone of the produced cDNA library. The amino acid sequence of C-hsi13412 is shown in SEQ ID NO: 1, and its nucleotide sequence is shown in SEQ ID NO: 3. The amino acid sequence of C-kaia397 is shown in SEQ ID NO: 2, and its nucleotide sequence is shown in SEQ ID NO: 4.

In homology analysis using BLAST2, the amino acid sequence of C-hsi13412 showed a significant homology of 38% with a P-value of $4.0 \times 10^{-41}$ to human IGFBP-7 (accession number: I52825), which is a protein belonging to the insulin-like growth factor binding protein family. Similarly, in the homology analysis using BLAST2, the amino acid sequence of C-kaia397 showed a significant homology of 35% with a P-value of $2 \times 10^{-16}$ to human IGFBP-7, which is a protein belonging to the insulin-like growth factor binding protein family. In the insulin-like growth factor binding protein superfamily, there are 10 cysteine residues that are important for the binding to IGF-1, IGF-2, and insulin; and mainly the insulin-like growth factor binding motif (GCGCCXXC (SEQ ID NO:26) (G: glycine residue, C: cysteine residue, X: arbitrary amino acid residue)) containing 4 of these cysteine residues are highly conserved among factors belonging to this family. According to a comparison of the amino acid sequences of C-hsi13412 and C-kaia397 with each factor of the insulin-like growth factor binding protein superfamily, it was revealed that the position and number of cysteine residues are also conserved and the insulin-like growth factor binding motif region was also found to be highly conserved in the amino acid sequences shown in SEQ ID NOS: 1 and 2 (FIG. 1). Furthermore, the signal sequence at the N-terminus was also highly conserved in C-hsi13412, C-kaia397, and among factors belonging to the insulin-like growth factor binding protein superfamily (FIG. 1).

According to the above-mentioned results, C-hsi13412 and C-kaia397 were revealed to be novel proteins belonging to the insulin-like growth factor binding protein superfamily that have the activity of the insulin-like growth factor binding protein superfamily. IGFBP-1, IGFBP-2, IGFBP-3, IGFBP-4, IGFBP-5, IGFBP-6, and IGFBP-7 in FIG. 1 represent human IGFBP-1, human IGFBP-2, human IGFBP-3, human IGFBP-4, human IGFBP-5, human IGFBP-6, and human IGFBP-7, respectively.

Furthermore, the amino acid sequence conserved among C-hsi13412, C-kaia397, and the insulin-like growth factor binding protein superfamily are shown in white on a dark background, and the cysteine residues that are highly conserved within the family are shown with an asterisk.

By searching nucleotide sequence databases, GenBank/EMBL/DDBJ, for the nucleotide sequence shown in SEQ ID NO: 3 using BLAST2, 2 nucleotide sequences that seemed to be ESTs derived from the same gene as the nucleotide sequence encoding the amino acid of C-hsi13412 was found to match to the sequence. The GenBank accession numbers of these ESTs are A1667734 and R30743. Similarly, by searching nucleotide sequence databases, GenBank/EMBL/DDBJ, for the nucleotide sequence shown in SEQ ID NO: 4 using BLAST2, 1 nucleotide sequence that seemed to be an EST derived from the same gene as the nucleotide sequence encoding the amino acid of C-kaia397 was found to match to the sequence. The GenBank accession number of this EST is A1667734. These EST nucleotide sequences do not cover the entire length of C-hsi13412 and C-kaia397. Furthermore, although genes showing homology to the nucleotide sequences of each EST were searched in each of the databases of GenBank, EMBL, and DDBJ using BLAST2, the ESTs did not show a significant homology to the insulin-like growth factor binding protein superfamily. Therefore, C-hsi13412 and C-kaia397 were revealed to be novel genes obtained for the first time by the present invention.

*Escherichia coli* harboring the plasmid C-hsi13412 that contains a cDNA (entire nucleotide sequence shown in SEQ ID NO: 3) encoding the protein having the amino acid sequence shown in SEQ ID NO: 1: *Escherichia coli* DH5α/pME18SFL3-C-hsi13412, and *Escherichia coli* harboring the plasmid C-kaia397 that contains a cDNA (entire nucleotide sequence shown in SEQ ID NO: 4) encoding the protein having the amino acid sequence shown in SEQ ID NO: 2: *Escherichia coli* DH5α/pME18SFL3-C-kaia397 have been deposited under the accession numbers, FERM BP-7181 and FERM BP-7180, respectively, in the National Institute of Advanced Industrial Science and Technology, Patent Microorganism Depositary, AIST Tsukuba Central 6, 1-1-1 Higashi, Tsukuba, Ibaraki, Japan (postal code 305-8366) (old name: National Institute of Bioscience and Human-Technology, National Institute of Advanced Industrial Science and Technology; old address: 1-1-3 Higashi, Tsukuba, Ibaraki, Japan 305-8566) on Jun. 2, 2000.

Example 3

Analysis of the Nucleotide Sequences of C-hsi13412 and C-kaia397

Figure 3:
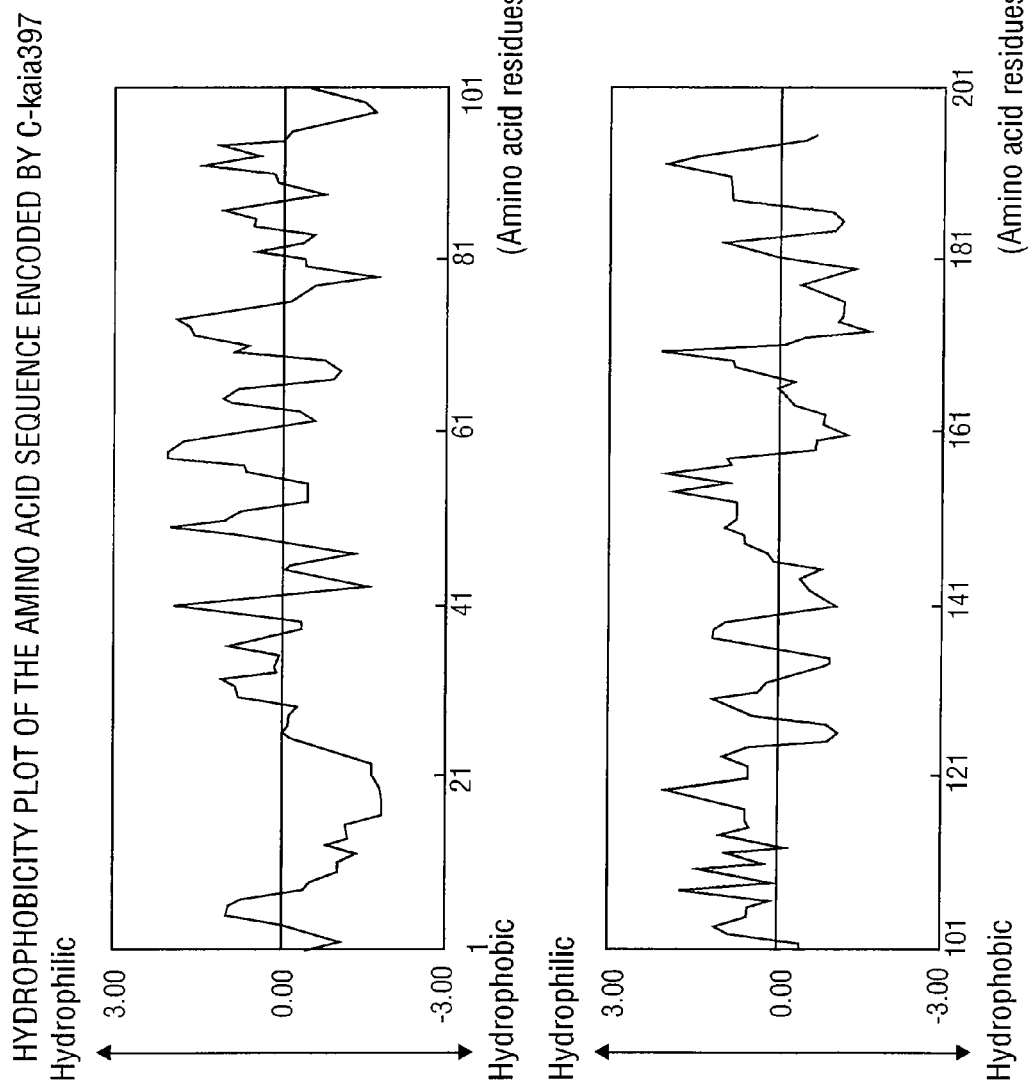
FIG. 3 shows the hydrophobicity plot of the protein encoded by C-kaia397.

Based on the nucleotide sequences of C-hsi13412 set forth in SEQ ID NO: 3 and C-kaia397 set forth in SEQ ID NO: 4, sequences in the vicinity of the initiation codon were analyzed using an initiation codon prediction program ATGPr for proteins (Bioinformatics, 14, 384 (1998)). ATG at positions 177 to 179 was specified as the initiation codon, and TAG at positions 1089 to 1091 was specified as the stop codon, and the protein encoded in the ORF was estimated to be composed of 304 amino acids for C-hsi13412. ATG at positions 926 to 928 was specified as the initiation codon, and TAG at positions 1517 to 1519 was specified as the stop codon, and the protein encoded in the ORF was estimated to be composed of 197 amino acids for C-kaia397. By mapping hydrophobicity plots using GENETYX-MAC 7.3 (SOFTWARE DEVELOPMENT CO., LTD) based on the amino acid sequences encoded by C-hsi13412 set forth in SEQ ID NO: 1 and C-kaia397 set forth in SEQ ID NO: 2, a highly hydrophobic region characteristic of secretory proteins existed in the N-terminal regions of both genes (FIG. 2, FIG. 3).

Example 4

Analysis of Genomic Genes of C-hsi13412 and C-kaia397

Based on the nucleotide sequences of C-hsi13412 set forth in SEQ ID NO: 3 and C-kaia397 set forth in SEQ ID NO: 4, nucleotide sequence information of the human genome DNA region containing both nucleotide sequences shown in SEQ ID NO: 3 and SEQ ID NO: 4 was obtained using GenomeWalker™ kits (Clontech) according to the attached instructions. Furthermore, searching the nucleotide sequence databases GenBank/EMBL/DDBJ using BLAST2, nucleotide sequence information of genomic clone AL133215 containing both of the nucleotide sequences shown in SEQ ID NO: 3 and SEQ ID NO: 4 was obtained.

Figure 4:
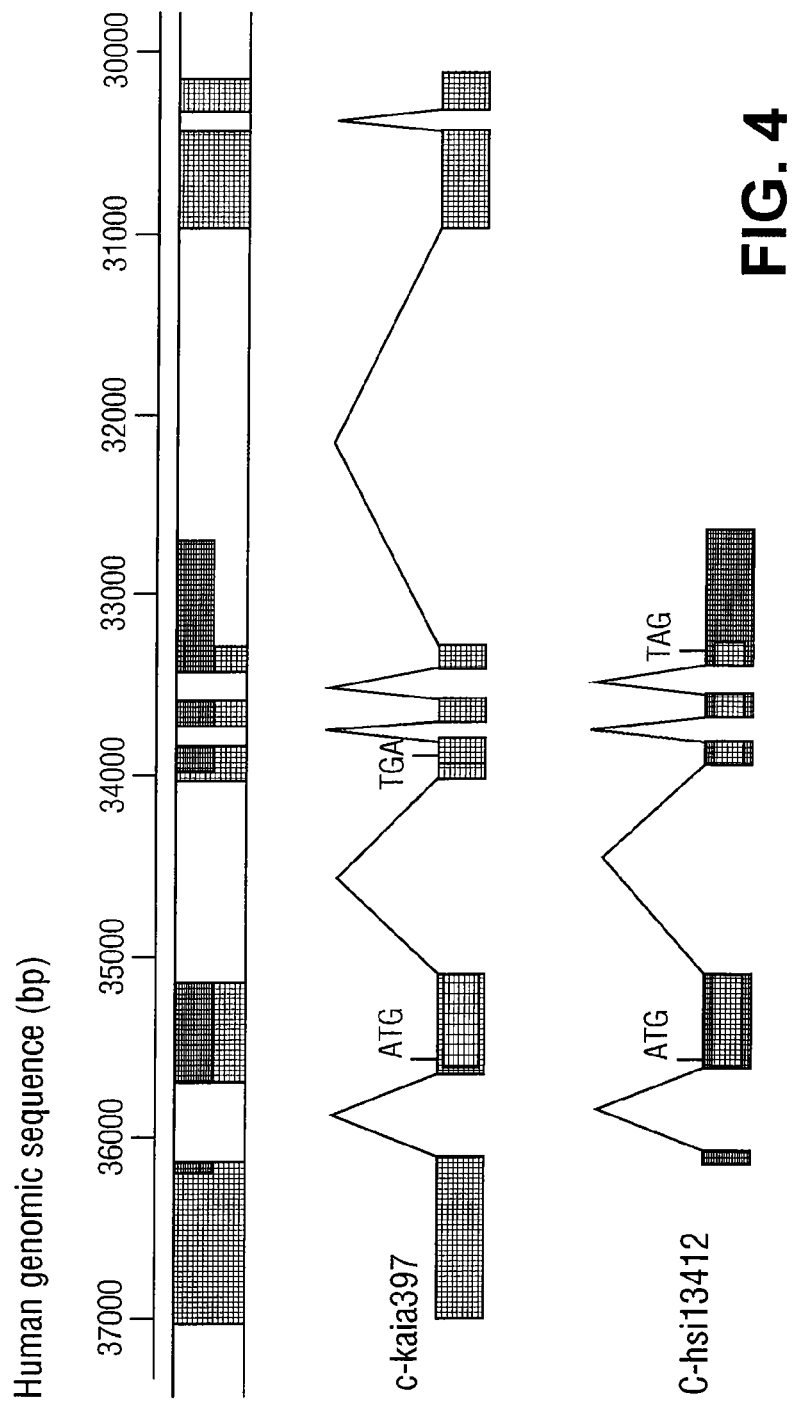
FIG. 4 shows the comparison of C-hsi13412 and C-kaia397, and the human genome sequence.

According to a comparison of the obtained human genomic sequence with the nucleotide sequence shown in SEQ ID NO: 3 and the nucleotide sequence shown in SEQ ID NO: 4, the nucleotide sequence shown in SEQ ID NO: 3 was found to exist separated in 5 parts, and the nucleotide sequence shown in SEQ ID NO: 4 in 7 parts over a span of approximately 7 kb on same human genome, chromosome 10 (FIG. 4). The protein having the amino acid sequence shown in SEQ ID NO: 1 is composed of 5 exons, and the protein having the amino acid sequence shown in SEQ ID NO: 2 is composed of 7 exons, and the 2nd and 4th exons completely coincided. Furthermore, differences observed in the comparison of amino acid sequences shown in SEQ ID NOS: 1 and 2 were found to arise due to the difference in the beginning of the 3rd exon and the end of the 5th exon of C-hsi13412 and C-kaia397. Therefore, the protein having the amino acid sequence shown in SEQ ID NO: 1 and the protein having the amino acid sequence shown in SEQ ID NO: 2 were found to be products of alternately spliced forms derived from the same gene, respectively, with the unique characteristic having different amino acid sequences from each other.

Example 5

Organs Expressing C-hsi13412 and C-kaia397

R30743, which is an EST identical to a part of the nucleotide sequence region encoding the amino acids of C-hsi13412, was isolated from fetal heart. This EST was found to be identical with 11 nucleotide sequences that seemed to be ESTs derived from the same gene by searching the nucleotide sequence of the 3' end noncoding region of a cDNA clone encoding C-hsi13412 in the nucleotide sequence databases GenBank, EMBL, and DDBJ using BLAST2. The GenBank accession numbers of these ESTs are AI658885, W28828, AI377545, AA896981, AA688321, AW370932, AA126609, AQ431640, AQ742986, AI971557, and AL030921. Among them, AI658885, W28828, AI377545, AA896981, AA688321, and AW370932 are registered as UniGene Hs.155234. AI658885 and AA688321 were isolated from prostate gland, and W28828, AA896981, AW370932, and AA126609 were isolated from eyes, spleen, mammary glands, and uterus of a pregnant woman, respectively.

Therefore, C-hsi13412 was presumed to be expressed in fetal heart, prostate gland, eye, spleen, mammary gland, and uterus of pregnant women. Similarly, the nucleotide sequence databases GenBank, EMBL, and DDBJ were searched for the nucleotide sequence of the 3' end noncoding region of a cDNA clone encoding C-kaia397 using BLAST2, and the sequence was revealed to be identical to 7 nucleotide sequences that were suggested to be ESTs derived from the same gene. The GenBank accession numbers of these ESTs are AA937577, AW080122, AA534966, AW374463, AQ394346, F23541, and F23538. AW080122, AA534966, and F23538 were isolated from esophagus, large intestine, and muscles, respectively. Therefore, C-kaia397 was presumed to be expressed in esophagus, large intestine, and muscles.

Example 6

Expression Analysis of C-hsi13412 and C-kaia397 Using RT-PCR cDNA was synthesized using the commercially available SUPER SCRIPT Preamplification System for first strand cDNA Synthesis (GIBCO BRL) according to the attached instructions, and, as a template, 4 µg of total RNA that was prepared by the AGPC method (Analytical Biochemistry, 162, 156 (1987); Experimental Medicine 9, 1937 (1991)) from 4 µg of human organ polyA$^+$ RNA purchased from Clontech and cancer cell line.

PolyA$^+$ RNA derived from brain, kidney, pancreas, pituitary gland, small intestine, bone marrow, heart, liver, lung, lymph node, mammary gland, placenta, prostate gland, skeletal muscle, spleen, stomach, testis, thymus, thyroid gland, and uterus were used as the human organ polyA$^+$ RNA.

T cell lines (Jurkat (Riken Cell Bank; RCB 086); Molt-3 (ATCC CRL-1552)), B cell lines (Namalwa KJM-1 (J. Biol. Chem., 268, 22782, 1993); Daudi (ATCC CCL-213)), monocytic cell line (HL-60 (ATCC CCL-240)), vascular endothelial cell lines (HUVEC (Kurabo); IVEC (J. Cell. Physiol., 157, 41, 1993; N. T. L. FRANCE)), melanoma cell lines (WM266-4 (ATCC CRL-1676); WM115 (ATCC CRL-1675)), neuroblastoma cell lines (SK– N-MC (ATCC HTB-10); SK-N-SH (ATCC HTB-11)), lung cancer cell lines (PC-9 (Immuno-Biological Laboratories); HLC-1 (Osaka University Cancer Research Institute); QG90 (Aichi Cancer Center)), gastric cancer cell line (KATO-III (Immuno-Biological Laboratories)), pancreatic cancer cell lines (Capan-1 (ATCC HTB-79); Capan-2 (ATCC HTB-80)), colon cancer cell lines (Colo 205 (ATCC CCL-222); SW1116 (Aichi Cancer Center); and LS180 (ATCC CCL-187)) were used as cancer cell lines.

Figure 5:
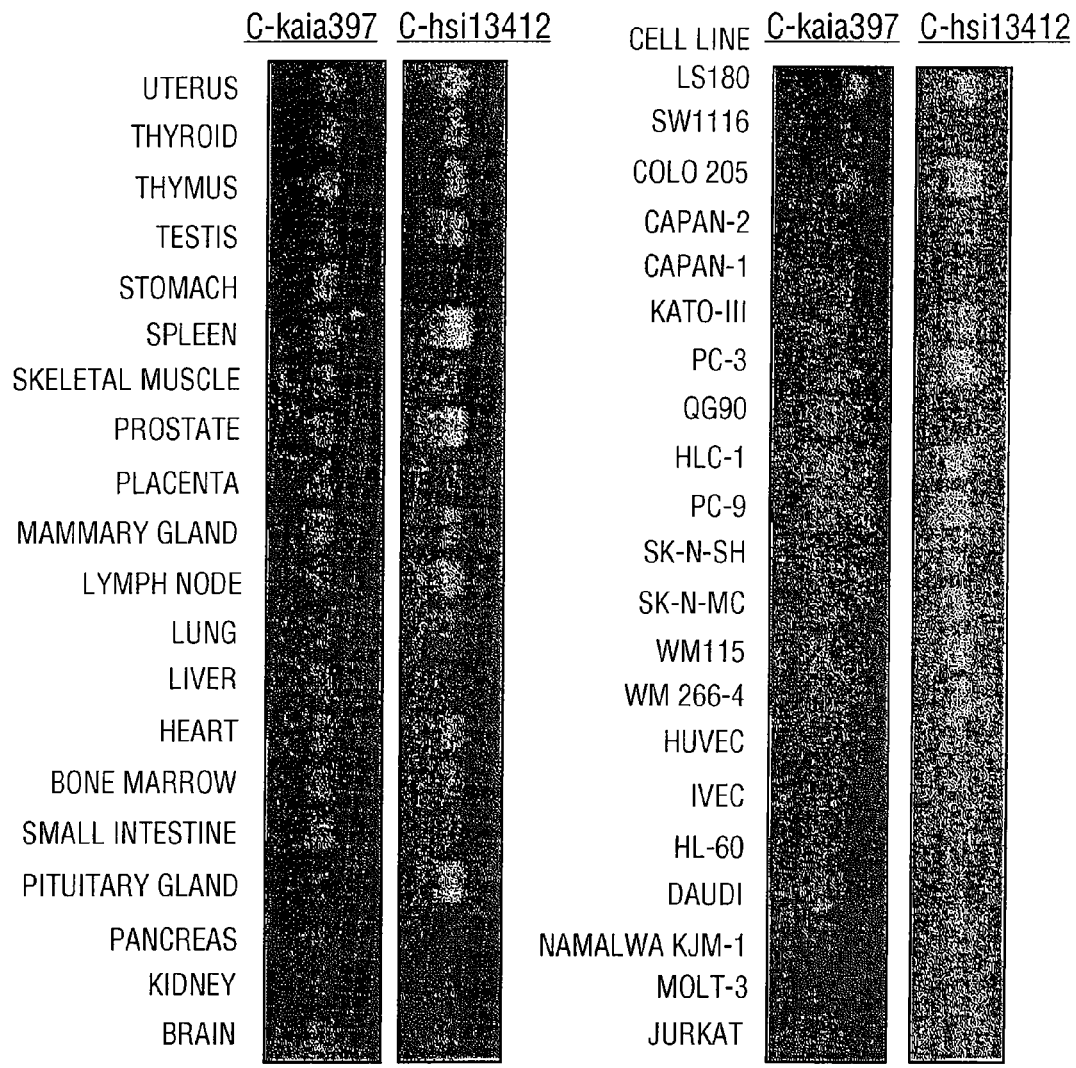
FIG. 5 shows the expression of C-hsi13412 and C-kaia397 by RT-PCR. The first panel shows the expression in each tissue, and the second panel shows the result of analyzing the expression in each cell line.

Next, PCR was performed using the synthesized cDNA as a template. Specifically, using primers containing sequences specific to C-hsi13412 and C-kaia397, and to human β-actin mentioned below, a reaction solution was prepared by a conventional method using a solution of the synthesized cDNA that was diluted 50 times using sterilized water and Advantage™ cDNA PCR kit (Clontech). Then, PCR was performed under a reaction at 94° C. for 7 minutes, repeating 32 cycles, one cycle consisting of reaction at 94° C. for 1 minute and reaction at 68° C. for 3 minutes, and finally 68° C. for 7 minutes. This reaction solution was subjected to agarose gel electrophoresis. By comparing the intensity of the DNA band specific to the used primers, the expression levels were semi-quantitatively compared. As a result, the expression patterns of C-hsi13412 and C-kaia397 were revealed to be different (FIG. 5).

The PCR was carried out using the oligonucleotides consisting of the nucleotide sequences shown in SEQ ID NO: 9 and SEQ ID NO: 10 as the primer set specific for C-hsi13412, the oligonucleotides consisting of the nucleotide sequences shown in SEQ ID NO: 9 and SEQ ID NO: 11 as the primer set specific for C-kaia397, and the oligonucleotides consisting of the nucleotide sequences shown in SEQ ID NO: 12 and SEQ ID NO: 13 as the primer set specific for human β-actin. Primer-specific DNA bands were confirmed in the above-mentioned RT-PCR reactions using these primer sets, and their sizes were approximately 730 bp, 310 bp, and 600 bp for C-hsi13412, C-kaia397, and human β-actin, respectively.

Figure 6:
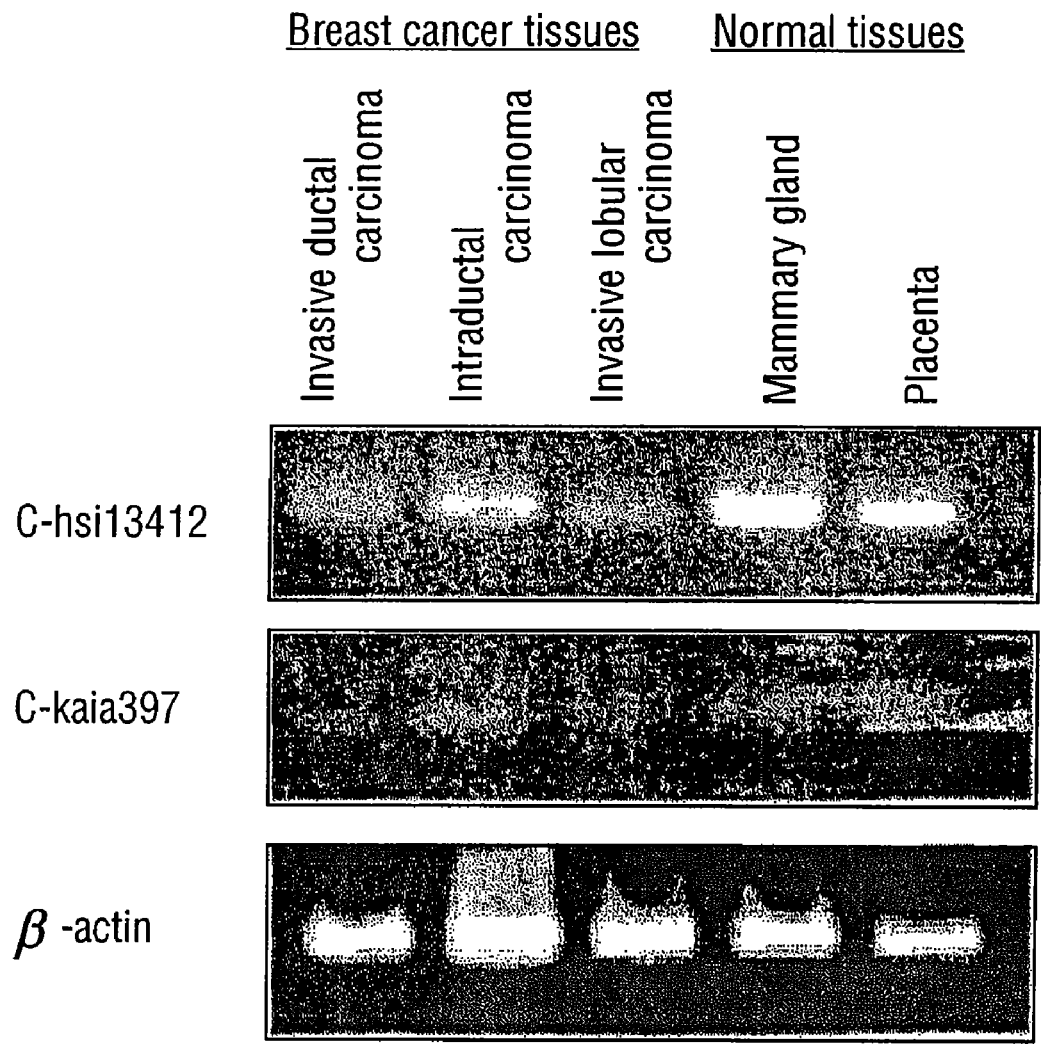
FIG. 6 shows the expression of C-hsi13412 and C-kaia397 by RT-PCR.

Furthermore, regarding the difference in the expression levels between normal tissues and cancer tissues of human, RT-PCR was carried out under the same conditions as mentioned above using Single Tumor Tissue Multi Sample Breast 1 (BioChain) as a template. C-hsi13412 and C-kaia397 were expressed in both normal tissues and cancer tissues. However, a tendency of decreased expression level was observed in the examined breast cancer tissues (FIG. 6).

Example 7

Expression Analysis of C-hsi13412 and C-kaia397 Using Northern Blotting Method

Expression patterns of C-hsi13412 and C-kaia397 among human cancer tissues and normal tissues were examined as follows using 96 Dot Tumor/Normal Tissue Total RNA Dot Blot (BioChain).

(1) Construction of DNA Probes

Using either of the 2 clones produced in Example 2, C-hsi13412 or C-kaia397, as a template, a reaction solution was prepared by a conventional method using a primer set consisting of the nucleotide sequences shown in SEQ ID NO: 9 and SEQ ID NO: 14, and Ex Taq DNA Polymerase (TAKARA). Then, PCR was carried out under a reaction at 94° C. for 10 min; repeating 35 cycles, one cycle consisting of reaction at 94° C. for 1 minute, reaction at 60° C. for 1 minute, and reaction at 72° C. for 2 minutes; and finally at 72° C. for 10 minutes. Then, separating the amplification product of approximately 300 bp by 1% agarose gel electrophoresis to prepare a DNA probe common to C-hsi13412 and C-kaia397.

The primer set consisting of the nucleotide sequences shown in SEQ ID NO: 9 and SEQ ID NO: 14 were designed based on the nucleotide sequence common between the coding region of C-hsi13412 and C-kaia397 set forth in SEQ ID NO: 3 and SEQ ID NO: 4, respectively.

(2) Constriction of Labeled DNA Probes

The DNA probe constructed in above (1) was labeled with a radioisotope (hereinafter, abbreviated as "RI") by the random priming method (Anal. Biochem. 132, 6 (1983), Anal. Biochem. 137, 266 (1984)).

A reaction solution was prepared using 75 ng of the above-mentioned DNA probe of (1), 5 μl of [α-$^{32}$P]dCTP (NEN), and Oligolabelling Kit (Amersham Pharmacia) according to the attached instructions, and the reaction was carried out at 37° C. for 1 hour. Then, the unreacted labeled nucleotides were removed by centrifugation using Centri-Sep Spin Column (PRONCETON SEPARATIONS) at 3,000 rpm for 2 minutes, to prepare RI-labeled DNA probe.

(3) Hybridization

Prehybridization was carried out by soaking the above-mentioned 96 Dot Tumor/Normal Tissue Total RNA Dot Blot membrane in 5 ml of prehybridization solution (6×SSPE (6×(0.15 M NaCl, 8.65 mM NaH2PO4.2H2O, 1.25 mM EDTA)), 2×Denhardt's Solution (Nacalai Tesque), 50% formamide, 0.5% SDS, 100 μg Salmon Sperm DNA (Stratagene)), shaking at 42° C., and then leaving standing for 3 hours. Meanwhile, the labeled DNA probe constructed in above (2) was denatured into single strands by heating at 94° C. for 5 minutes. After 3 hours of prehybridization, the membrane was soaked in 2 ml of fresh prehybridization solution, and the labeled DNA probe denatured into single strands were added so that the specific activity of RI is 2×106 cpmrn/ml. Hybridization was carried out by leaving shaking at 42° C. for 20 hours.

(4) Membrane Washing

The membrane was recovered from the hybridization solution, and shaken twice in 2×SSPE containing 0.1% SDS at 42° C. for 10 minutes with exchange of the solvent and three times at 50° C. for 30 minutes to wash the membrane.

(5) Signal Detection

The washed membrane was placed into a cassette for X-ray films with an X-ray film, and autoradiography was performed by leaving standing at −80° C. for 24 hours to detect the signal.

As a result of the analysis of the signal, in normal cells, the expression was mainly observed in stomach, small intestine, gall bladder, thyroid gland, kidney, bladder, thymus, prostate gland, and mammary gland. On the other hand, in cancer tissues, the expression was mainly observed in stomach, pancreas, bladder, prostate gland, mammary gland, thyroid gland, and thymus. In addition, in kidney, gall bladder, small intestine, and thyroid gland, decrease of expression was observed in cancer tissues compared to normal tissues. However, significant differences were not exactly observed in other tissues. As shown in Example 6, since the expression patterns of C-hsi13412 and C-kaia397 differ depending on the types of tissues and cancer, the importance of expression analysis by Northern Blotting using probes that do not differentiate between C-hsi13412 and C-kaia397, as well as expression analysis that differentiates between C-hsi13412 and C-kaia397 was suggested.

Example 8

Expression of Proteins Encoded by C-hsi13412 or C-kaia397 Using Animal Cells as hosts (1)

(1) Construction of Recombinant Vectors (i) pcDNA3-C-hsi13412

Using the clone C-hsi13412 constructed in Example 2 as a template, and using a primer set consisting of the nucleotide sequences shown in SEQ ID NO: 15 and SEQ ID NO: 16 and KOD DNA Polymerase (TOYOBO), a reaction solution was prepared by a conventional method. Then PCR was performed under a condition of 25 cycles, one cycle consisting of reaction at 98° C. for 15 seconds, reaction at 65° C. for 2 seconds, and reaction at 74° C. for 30 seconds. The primer set consisting of the nucleotide sequences shown in SEQ ID NO: 15 and SEQ ID NO: 16 were designed so that FLAG marker peptide is added to the C-terminus of C-hsi13412. Next, pSK-C-hsi13412 was constructed by inserting the obtained amplification product of approximately 990 bp into the SmaI site of pBluescript II SK− (Stratagene), so that the 5' side of C-hsi13412 is on the side of KpnI site of pBluescript II SK−, and the 3' side of C-hsi13412 on the side of SacI site of pBluescript II SK−.

Next, the EcoRI-NotI fragment (900 bp) of pSK-C-hsi13412 was inserted into the EcoRI-NotI site of pcDNA3 (Invitrogen), an expression vector for animal cells, to construct pcDNA3-C-hsi13412.

(ii) pcDNA3-C-kaia397

Using the clone C-kaia397 constructed in Example 2 as a template, and using a primer set consisting of the nucleotide sequences shown in SEQ ID NO: 15 and SEQ ID NO: 17 and KOD DNA Polymerase (TOYOBO), a reaction solution was prepared by a conventional method. Then PCR was performed under a condition of 25 cycles, one cycle consisting of reaction at 98° C. for 15 seconds, reaction at 65° C. for 2 seconds, and reaction at 74° C. for 30 seconds. The primer set consisting of the nucleotide sequences shown in SEQ ID NO: 15 and SEQ ID NO: 17 were designed so that FLAG marker peptide is added to the C-terminus of C-kaia397. Next, pSK-C-kaia397 was produced by inserting the obtained amplification product of approximately 620 bp into the SmaI site of pBluescript II SK– (Stratagene), so that the 5' side of C-kaia397 is on the side of KpnI site of pBluescript II SK–, and the 3' side of C-kaia397 on the side of SacI site of pBluescript II SK–.

Next, the EcoRI-NotI fragment (600 bp) of pSK-C-kaia397 was inserted into the EcoRI-NotI site of pcDNA3 (Invitrogen), an expression vector for animal cells, to construct pcDNA3-C-kaia397.

(2) Insertion of Vectors into Cells

2 µl of FuGENE™ 6 transfection reagent (Roche Diagnostics) was added to 100 µl of Opti-MEM (Gibco), and was left standing at room temperature for 5 minutes. Then, 1 µl of control plasmid pcDNA3, the C-hsi13412 expression plasmid pcDNA-3-C-hsi13412 constructed in (1)(i) mentioned above, or the C-kaia397 expression plasmid pcDNA3-C-kaia397 constructed in (1)(ii) mentioned above was added, and was left standing at room temperature for another 15 minutes. Meanwhile, 2 ml/well aliquots of DMEM medium containing 10% dFCS were placed into a 6-well plate, and COS-1 cells (Riken Cell Bank; RCB0143) were plated at $3\times10^5$/well. After leaving standing for 15 minutes, 25 µl/well aliquots of a mixed solution of the plasmid and FuGENE™ 6 transfection reagent were added to the 6-well plate, and was cultivated at 37° C. for 72 hours in a $CO_2$ incubator to obtain a transiently transfectant. Hereinafter, the transfected cell lines produced by introducing pcDNA3, C-hsi13412, and C-kaia397 will be referred to as COS-1/mock cell line, COS-1/C-hsi13412 cell line, and COS-1/C-kaia397 cell line, respectively.

(3) Confirmation of Expression (i) Preparation of Culture Supernatants

Culture supernatants were obtained by collecting 4 ml of the culture supernatants of COS-1/mock cell line, COS-1/C-hsi13412 cell line, and COS-1/C-kaia397 cell line produced in above (2), and removing solids by centrifugation at 1,200 rpm for 5 minutes. The obtained culture supernatants were stored at –20° C., and were used in the following experiments upon thawing as necessary.

(ii) Acquisition of Cell Lysate

After detaching cells of COS-1/mock cell line, COS-1/C-hsi13412 cell line, and COS-1/C-kaia397 cell line produced in the above-mentioned (2) from the 6-well plate with a cell scraper (Sumitomo Bakelite), the cells were suspended in 2 ml of Phosphate Buffered Saline (pH 7.2) (hereinafter, referred to as "PBS" (Gibco)), and were centrifuged at 1,200 rpm for 5 minutes to remove the supernatant. Next, the resulting precipitate was suspended in 1 ml of PBS containing 100 µl of protease inhibitor cocktail for animal cells (Sigma), and subjected to ultrasonic homogenization to obtain cell lysate. The obtained cell lysate was stored at –20° C., and was used for the following experiments upon thawing as necessary.

(iii) Detection by Western Blotting

Western Blotting was carried out in 10 µl of the culture supernatant prepared in above (3)(i) or 5 µl of the cell lysate prepared in above (3)(ii) using anti-FLAG M2 monoclonal antibody (Sigma) as the detection antibody according to Example 14.

Figure 7:
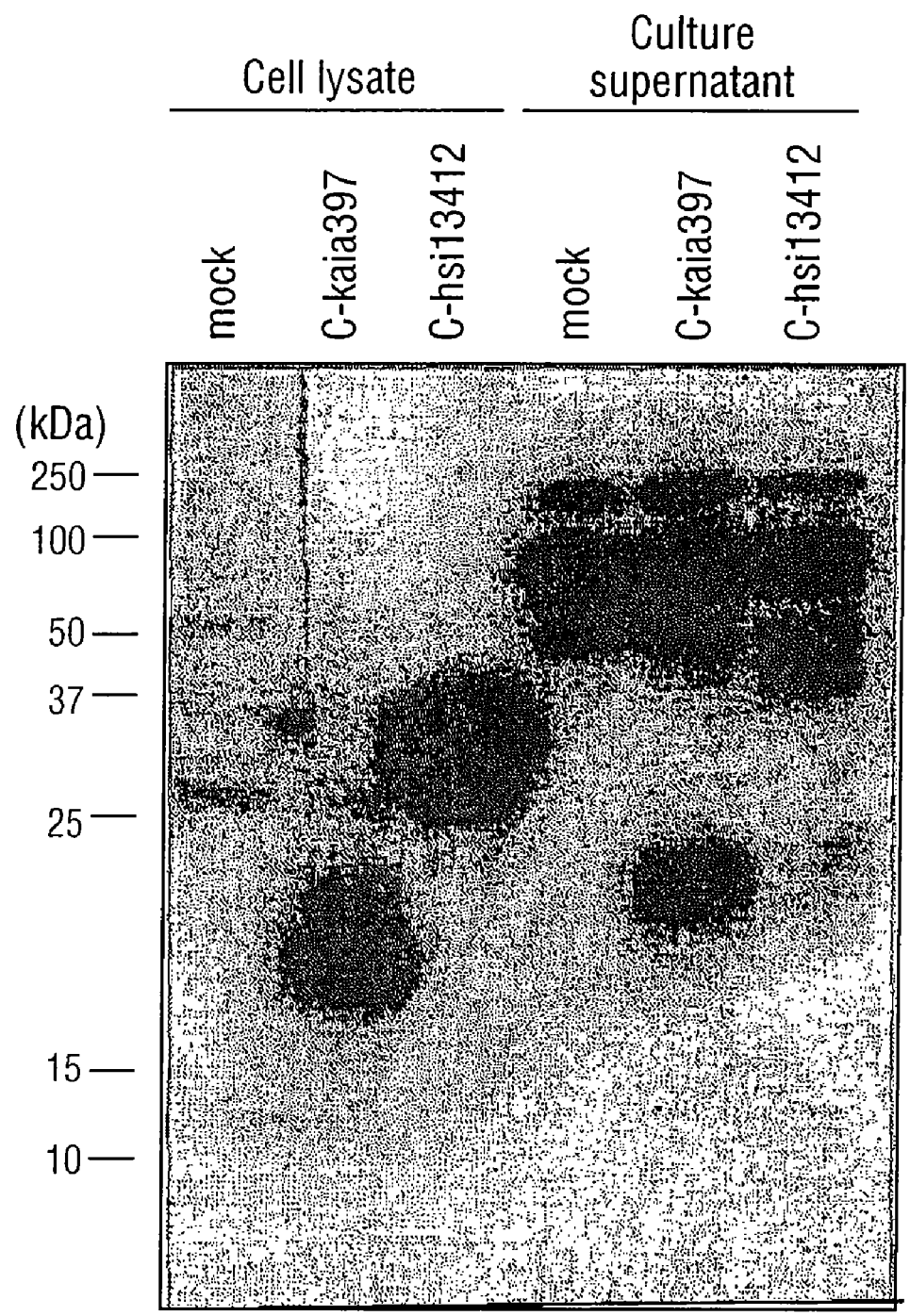
FIG. 7 shows the expression of the proteins encoded by C-hsi13412 and C-kaia397 using COS-1 cells as hosts. Mock represents the control.

Bands that were not observed in COS-1/mock cell line were detected in both the cell lysate and culture supernatant of COS-1/C-hsi13412 cell line and COS-1/C-kaia397 cell line. Therefore, the expression of proteins encoded by C-hsi13412 and C-kaia397 were confirmed in COS-1 cells (FIG. 7).

Example 9

Expression of Proteins Encoded by C-hsi13412 or C-kaia397 Using Animal Cells as Hosts (2)

(1) Construction of Recombinant Vectors (i) Construction of pAGE210-C-hsi13412 and pAGE210-C-hsi13412h Using pSK-C-hsi13412 produced in Example 8 as a template, an oligonucleotide primer set consisting of the nucleotide sequences shown in SEQ ID NO: 18 and SEQ ID NO: 19, or an oligonucleotide primer set consisting of the nucleotide sequences shown in SEQ ID NO: 18 and SEQ ID NO: 20, and native pfu polymerase (STRATAGENE), a reaction solution was prepared by a conventional method. Then PCR was performed under a reaction condition of 94° C. for 5 minutes; 25 repeating cycles, one cycle consisting of reaction at 94° C. for 1 minute, reaction at 55° C. for 1 minute, and reaction at 72° C. for 2 minutes; and finally 72° C. for 7 minutes.

Next, pSK-C-hsi13412c and pSK-C-hsi13412h were constructed by inserting the obtained amplification product of approximately 900 bp into the HindIII-XbaI site of pBluescript II SK–.

Then, the HindIII-XbaI fragments (900 bp) of pSK-C-hsi13412c and pSK-C-hsi13412h were inserted into the HindIII-XbaI site of pAGE210, a vector for animal cell expression (J. Biochem., 101, 1307 (1987)), to construct pAGE210-C-hsi13412 and pAGE210-C-hsi13412h.

(ii) pAGE210-C-kaia397 and pUC-C-kaia397h

Using the pSK-C-kaia397 produced in Example 8 as a template, and an oligonucleotide primer set consisting of the nucleotide sequences shown in SEQ ID NO: 18 and SEQ ID NO: 21 or an oligonucleotide primer set consisting of the nucleotide sequences shown in SEQ ID NO: 18 and SEQ ID NO: 22, PCR was performed as described in above (i).

Next, the obtained amplification product of approximately 600 bp was inserted into the HindIII-XbaI site of pBluescript II SK– to construct pSK-C-kaia397c and pSK-C-kaia397h.

Then, the HindIII-XbaI fragments (600 bp) of pSK-C-kaia397c and pSK-C-kaia397h were inserted into the HindIII-XbaI sites of pAGE210 and pUC18 (Amersham Pharmacia) to construct pAGE210-C-kaia397 and pUC-C-kaia397h.

(2) Introduction of Vectors into Cells pAGE210-C-hsi13412, pAGE210-C-hsi13412h, pAGE210-C-kaia397, and pUC-C-kaia397h constructed in above (1)(i) and (ii) were introduced into CHO cells (Somatic Cell and Molecular Genetics, 12, 555 (1986))) by the electroporation method (Cytotechnology, 3, 133 (1990))) as follows.

pAGE210, pAGE210-C-hsi13412, pAGE210-C-hsi13412h, pAGE210-C-kaia397, and pUC-C-kaia397h were cleaved at FspI, and were linearized. After phenol-chloroform extraction treatment, ethanol precipitation was carried out, and the obtained linearized plasmids were dissolved in TE solution. On the other hand, CHO cells were subcultured in αMEM1900 medium (Gibco) supplemented with 5% fetal calf serum (Gibco), 0.09% sodium bicarbonate (Gibco), and 1% Penicillin-streptomycin (Gibco) (hereinafter, referred to as "A medium") and were used for the experiment. The CHO cells were suspended in K-PBS buffer (137 nmol/l potassium chloride, 2.7 nmol/l sodium chloride, 8.1 mmol/l disodium hydrogen phosphate, 1.5 nmol/l sodium dihydrogen phosphate, 4 mmol/l magnesium chloride buffer) to a concentration of $8 \times 10^6$ cells/ml, and 200 µl of the cell suspension solution (containing $1.6 \times 10^6$ cells) were mixed with 4 µg of the above-mentioned linearized plasmid. The mixed solution was transferred to a cuvette (inter-electrode distance of 2 mm), and using Gene Pulser II (BioRad) apparatus, gene transfer was carried out under a condition of pulse voltage of 0.30 kV, and capacitance of 250 µF. After leaving the cuvette standing on ice, the cell suspension in the cuvette was suspended in 15 ml of A medium, a 5 ml aliquot thereof was placed into a flask and was cultivated in a 5% carbon dioxide gas incubator at 37° C. After cultivating for 1 day, the medium was exchanged to αMEM2000 medium supplemented with 5% fetal calf serum, 0.09% sodium bicarbonate, 1% Penicillin-streptomycin, and 300 µg/ml hygromycin B (Gibco) (hereinafter, referred to as "B medium"), and cultivation was continued. The subculturing was continued with dilution during the process, and approximately 2 weeks after gene transfer, transfected cell line having resistance to hygromycin B was obtained. The transfected cell line was subcultured in B medium. Hereinafter, transfected cell lines produced by introducing pAGE210, pAGE210-C-hsi13412, pAGE210-C-hsi13412h, pAGE210-C-kaia397, and pUC-C-kaia397h will be referred to as CHO/mock cell line, CHO/C-hsi13412 cell line, CHO/C-hsi13412h cell line, CHO/C-kaia397 cell line, and CHO/C-kaia397h cell line, respectively.

(3) Ascertainment of Expression

CHO/mock cell line, CHO/C-hsi13412 cell line, CHO/C-hsi13412h cell line, CHO/C-kaia397 cell line, and CHO/C-kaia397h cell line produced in above (2) were cultivated by static culture using B medium. Cells plated at a cell density of approximately one fifth confluence were grown to a state wherein the cells almost completely filled the surface of a 25 cm²-cultivation container, and the culture supernatant and the cells were collected separately. 100 µl of the collected culture supernatant was subjected to organic solvent precipitation using acetone, and the pellet was resolved in 50 µl of 100 mmol/l Tris-HCl buffer (pH 7.5) to prepare a supernatant fraction. Cells were collected using a cell scraper, suspended into 500 µl of 100 mmol/l Tris-HCl buffer (pH 7.5), and then subjected to ultrasonic homogenization to prepare a cell fraction. After separating 11.25 µl each of the prepared supernatant fraction or the cell fraction by SDS polyacrylamide gel electrophoresis according to the Laemmli method, Western Blotting analysis was carried out according to Example 14 using anti-C-hsi13412/C-kaia397 monoclonal antibody KM2962 produced in Example 13.

In all of the CHO/C-hsi13412, CHO/C-hsi13412h, CHO/C-kaia397, and CHO/C-kaia397h cell lines, expression of C-hsi13412 or C-kaia397 was ascertained in both the culture supernatant and cell fractions. The expression levels were higher in the cell fractions than in the culture supernatants in all of the transfected cell lines. Furthermore, regarding the molecular weight, when COS-1/C-hsi13412 cell line and COS-1/C-kaia397 cell line were expressed using COS-1 cell as the host, nearly identical mobilities were indicated.

Figure 8:
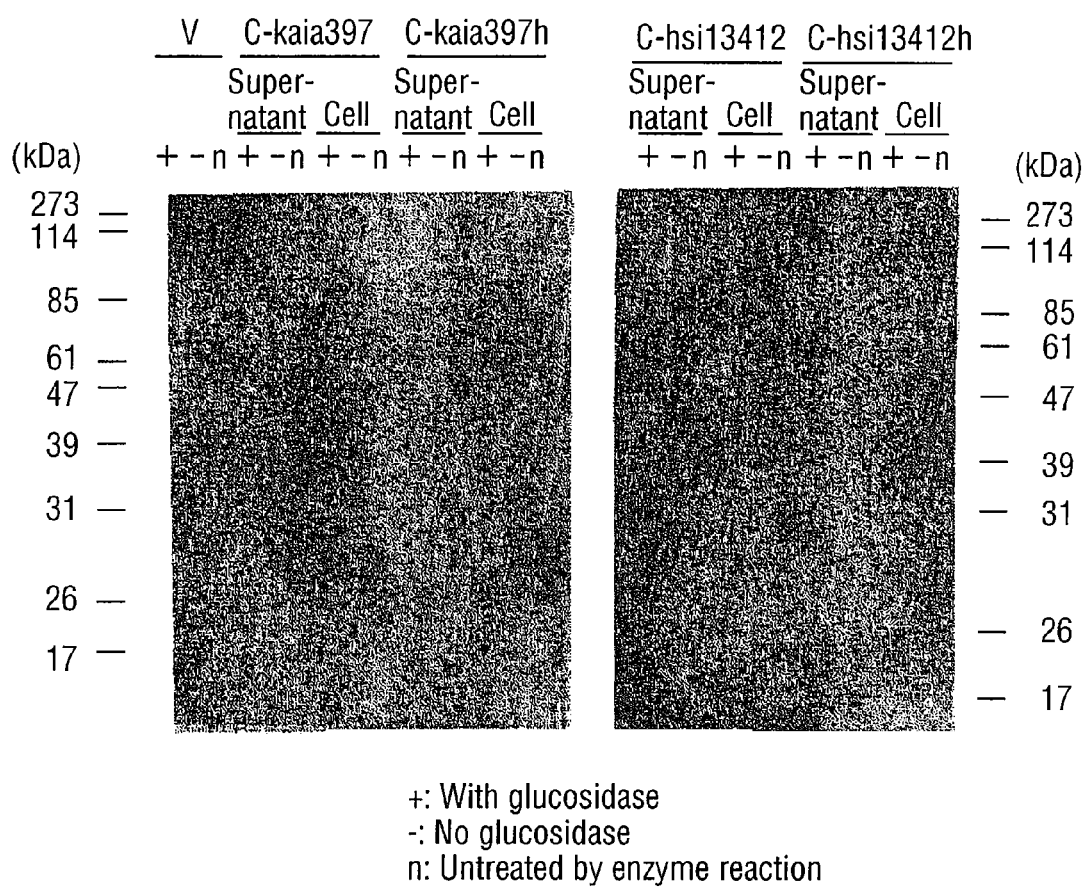
FIG. 8 shows the expression and glycosylation of the proteins encoded by C-hsi13412 and C-kaia397 using CHO cells as hosts. In the figure, V indicates CHO/mock cell line, C-kaia397 indicates CHO/C-kaia397 cell line, C-kaia397h indicates CHO/C-kaia397h cell line, C-hsi13412 indicates CHO/C-hsi13412 cell line, and C-hsi13412h indicates CHO/C-hsi13412h cell line. In addition, + indicates the addition of glycosidase, − indicates the addition of 100 mmol/l of Tris-HCl buffer (pH 7.5) instead of glycosidase, and n indicates cases without enzyme reaction.

As mentioned above, the expression of C-hsi13412 and C-kaia397 in CHO cells was ascertained (FIG. 8).

(4) Ascertainment of Glycosylation

Next, 7.5 µl of 1% SDS was added to 36 µl of the supernatant fraction or 36 µl of the cell fraction prepared in above (3), and was denatured by heating at 95° C. for 5 minutes. After the denaturing, 5 µl of 5% Nonidet P-40 (NP-40; polyoxyethylenenonylphenyl ether (Sigma)), 2 µl of 25 mM/50 µl of Glycopeptidase F (N-type glycosidase (Takara)), and 1 µl of 25 mM/50 µl of o-Glycosidase (o-type glycosidase (Roche Diagnostics)) were added to 14.5 µl of the supernatant fraction or 14.5 µl of the cell fraction, and was reacted at 37° C. overnight. As a control, a reaction solution in which 8 µl of 100 mmol/l Tris-HCl buffer (pH 7.5) was added instead of a glycosidase solution was prepared. Using 11.25 µl of the supernatant fraction or 11.25 µl of the cell fraction after reaction, Western Blotting analysis was performed as in above (3).

Since the molecular weights changed due to the addition of glycosidases, proteins encoded by C-hsi13412 and C-kaia397 produced by the transfected cells were presumed to be glycosylated (FIG. 8).

Example 10

Expression of Protein Encoded by C-hsi13412 Using Insect Cells as the Host

To produce recombinant proteins in insect cells, a recombinant virus wherein the desired gene has been incorporated has to be constructed. Such construction includes the steps of: (1) constructing a specific vector carrying a cDNA encoding the desired protein; (2) cotransfecting a baculovirus DNA and a transfer vector into insect cells to construct a recombinant virus by homologous recombination, and then growing them; and (3) expressing the desired protein by infecting cells with the recombinant virus. The details are described below.

(1) Construction of a Transfer Vector pVL-C-hsi13412, a transfer vector encoding the full length of C-hsi13412 (the amino acid sequence of the amino acid residues at position 1 to 304 of SEQ ID NO: 1), was constructed by inserting the EcoRI-BamHI fragment (900 bp) of plasmid pSK-C-hsi13412 of Example 8 into the EcoRI-BamHI site of insect cell transfer vector pVL1392 (PharMingen).

(2) Construction of a Recombinant Virus

Recombinant baculovirus was constructed by introducing linear baculovirus DNA (BaculoGold Baculovirus DNA (PharMingen)) and the transfer vector constructed in above (1) using the lipofectin method (Protein, Nucleic Acid, and Protein, 37, 2701 (1992)) to insect cells Sf9 (Iwaki Glass) cultivated in ESF921 medium (Protein Expression). The details are described below.

pVL-C-hsi13412 and 15 ng of linear baculovirus DNA were dissolved in 12 µl of sterilized distilled water, a mixture of 6 µl of lipofectin and 6 µl of sterilized distilled water was added thereto, and the mixture was left standing at room temperature for 15 minutes. Meanwhile, $1 \times 10^6$ Sf9 cells were suspended in 2 ml of ESF921 medium, and was placed into a 50 mm diameter plastic Petri dish for cell cultivation. All of the mixed solution of the above-mentioned plasmid DNA, linear baculovirus DNA, and lipofectin were added to the dish, and after cultivation at 27° C. for 3 days, 1 ml of the culture supernatant containing the recombinant virus was collected. 1 ml of ESF921 medium was freshly added to the Petri dish, and the dish was cultivated at 27° C. for additional 3 days to obtain another 1.5 ml of culture supernatant containing the recombinant virus.

Next, a recombinant virus that retains the C-hsi13412 gene was grown by the following procedure.

Sf9 cells were inoculated into 50 ml ESF921 medium at $5 \times 10^5$/ml, and were cultivated with shaking at 125 rpm at 27° C. using a 125 ml Erlenmeyer flask. When the cells grew to $2 \times 10^6$/ml, the cells were infected with the recombinant virus at MOI=10, and were further cultivated for 3 days. The culture solution was centrifuged at 1,200 rpm for 10 minutes to remove the cells, and a recombinant virus solution for protein expression was obtained.

The titer of the recombinant virus solution was measured by the following method.

$6 \times 10^5$ Sf9 cells were suspended in 4 ml of ES F921 medium, placed into a 50 mm diameter plastic Petri dish for cell culture, and adhered to the Petri dish by leaving standing at room temperature for 1 hour. The supernatant was removed, 100 µl of the above-mentioned recombinant virus solution diluted with ESF921 medium and 400 µl of ESF921 medium were added, after leaving standing at room temperature for 1 hour, the medium was removed, and 5 ml of a medium containing 1% low-melting-point agarose (Agar-Plaque Agarose (PharMingen)) (a medium prepared by mixing 1 ml of sterilized 5% aqueous AgarPlaque Agarose solution and 4 ml of TMN-FH Insect Medium (PharMingen), and warming at 42° C.) was poured into the Petri dish. After leaving standing at room temperature for 15 minutes, the Petri dish was sealed with a vinyl tape to prevent drying, was placed into a sealable plastic container, and was cultivated at 27° C. for 5 days. 1 ml of PBS containing 0.01% neutral red was added to the Petri dish, and was cultivated for another day. Then, the number of plaques that appeared was counted, and the preparation of a 0.5 to $2 \times 10^8$/ml recombinant virus solution was confirmed.

(3) Expression of Proteins

Sf9 cells were placed into 100 ml of ESF921 medium at $5 \times 10^5$/ml, and were cultured while shaking at 125 rpm at 27° C. using a 250 ml Erlenmeyer flask. When the cells grew to 3 to $4 \times 10^6$/ml, the cells were subcultured into a flask with a base area of 182 cm² containing 25 ml of ESF921 media, so as to contain $3 \times 10^7$ cells. After adhering the cells by leaving standing at room temperature for 1 hour, the medium was removed, and the recombinant virus carrying the C-hsi13412 gene was added at MOI=5. Then ESF921 medium was further added to a total volume of 10 ml, and was infected at room temperature for 1 hour. Subsequently, 20 ml of ESF921 medium was added, and the desired recombinant protein was expressed by culture at 27° C. for 3 days.

Western Blotting using anti-FLAG M2 monoclonal antibody (Sigma) was carried out according to Example 14, using 5 µl of cell suspension of cells that were infected with the recombinant virus carrying the C-hsi13412 gene and 20 µl of the culture supernatant as samples.

Figure 9:
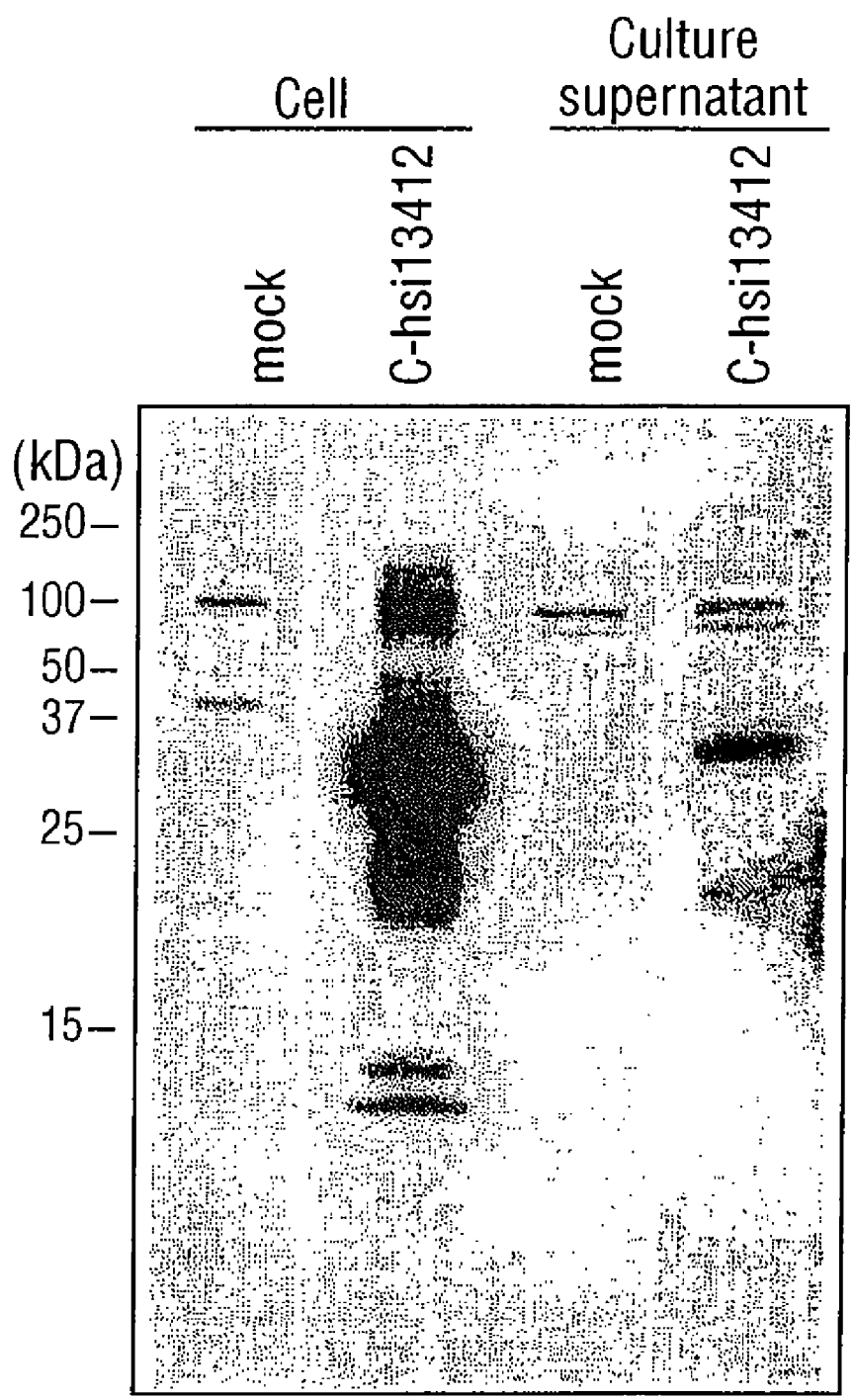
FIG. 9 shows the expression of proteins encoded by C-hsi13412 and C-kaia397 using insect cells as hosts. Mock represents the control.

A band at a molecular weight of approximately 33 kDa, which was not observed in uninfected cells, was detected in both the cell suspension and the culture supernatant of cells that were infected with C-hsi13412 (FIG. 9).

Example 11

Preparation of Antigens for Producing Antibodies Against Proteins Encoded by C-hsi13412 or C-kaia397

The amino acid sequences of the proteins encoded by C-hsi13412 and C-kaia397 were analyzed, and compound 1 (a polypeptide having the amino acid sequence shown in SEQ ID NO: 23), compound 2 (a polypeptide having the amino acid sequence shown in SEQ ID NO: 24), and compound 3 (a polypeptide having the amino acid sequence shown in SEQ ID NO: 25) were selected from highly hydrophilic regions, N-termini, C-termini, regions having a turn structure in their secondary structure, and a region having a random coil structure, as partial sequences that were suggested to be suitable as antigens.

The amino acids used in the present invention and the abbreviations of the protecting groups thereof were in accordance with the recommendations of IUPAC-IUB Joint Commission on Biochemical Nomenclature (European Journal of Biochemistry, 138, 9 (1984)).

The following abbreviations represent the corresponding amino acids mentioned below, unless stated otherwise.

Ala: L-alanine

Asn: L-asparagine

Asp: L-aspartic acid

Asx: L-aspartic acid or L-asparagine

Arg: L-arginine

Cys: L-cysteine

Glu: L-glutamic acid

Glx: L-glutamic acid or L-glutamine

Gly: glycine

Leu: L-leucine

Phe: L-phenylalanine

Pro: L-proline

Ser: L-serine

Thr: L-threonine

Trp: L-tryptophan

Tyr: L-tyrosine

Met: L-methionine

Val: L-valine

The following abbreviations represent the corresponding amino acid protecting groups and side chain protected amino acids mentioned below.

Fmoc: 9-fluorenylmethyloxycarbonyl tBu: t-butyl

Trt: trityl

Boc: t-butoxycarbonyl

Pmc: 2,2,5,7,8-pentamethylchroman-6-sulfonyl

Fmoc-Arg(Pmc)-OH:

N$^\alpha$-9-fluorenylmethyloxycarbonyl-N$^\gamma$-7-2,2,5,7,8-pentamethylchroman-6-sulfonyl-L-arginine Fmoc-Asn(Trt)-OH: N$^\alpha$-9-fluorenylmethyloxycarbonyl-N$^\gamma$-trityl-L-asparagine Fmoc-Asp(OtBu)-OH: N$^\alpha$-9-fluorenylmethyloxycarbonyl-L-aspartic acid-β-t-butylester Fmoc-Cys(Trt)-OH: N$^\alpha$-9-fluorenylmethyloxycarbonyl-5-trityl-L-cysteine Fmoc-Glu(OtBu)-OH: N$^\alpha$-9-fluorenylmethyloxycarbonyl-L-glutamic acid-γ-t-butylester Fmoc-Ser(tBu)-OH: N$^\alpha$-9-fluorenylmethyloxycarbonyl-O-t-butyl-L-serine Fmoc-Thr(tBu)-OH: N$^\alpha$-9-fluorenylmethyloxycarbonyl-O-t-butyl-L-threonine Fmoc-Trp(Boc)-OH: N$^\alpha$-9-fluorenylmethyloxycarbonyl-N$^{ind}$-t-butyloxycarbonyl-L-tryptophan Fmoc-Tyr(tBu)-OH: N$^\alpha$-9-fluorenylmethyloxycarbonyl-O-t-butyl-L-tyrosine The following abbreviations represent the corresponding reaction solvents, reaction reagents, and such mentioned below.

HBTU: 2-(1H-benzotriazole-1-yl)-1,1,3,3-tetramethyluronium hexafluorophosphate

HOBt: N-hydroxybenzotriazole

DIEA: diisopropylethylamine

DMF: N,N-dimethylformamide

TFA: trifluoroacetic acid

The physicochemical properties of the compounds were measured by the following method in Examples below.

Mass spectrometry was carried out by the FAB-MS method using JEOL JMS-HX110A, or by the MALDI-TOFMS method using Brucker Mass Spectrometer REFLEX. Amino acid analysis was carried out by the method of Cohen, S. A. et al (Analytical Biochemistry, 222, 19 (1994)). Hydrolysis was carried out in hydrochloric acid vapor at 110° C. for 20 hours, and the amino acid composition of the hydrolysis product was analyzed using Waters AccQ-Tag amino acid analyzer (Waters).

(1) Synthesis of Compound 1 (a Peptide Comprising the Amino Acid Sequence Shown in SEQ ID NO:23, H-Cys-Arg-Pro-Ser-Pro-Gly-Pro-Asp-Tyr-Leu-Arg-Arg-Gly-Trp-Met-Arg-Leu-NH$_2$)

30 mg of carrier resin (Rink amide MBHA resin, Novabiochem) bound with 18 μmol of Fmoc-NH were placed into a reaction container of automatic synthesizer (Shimadzu). 600 μl of DMF was added thereto, and was stirred for 3 minutes, and the solution was drained. Then, the following procedures were carried out according to a synthesis program of Shimadzu.

(a) 500 μl of 30% piperidine-DMF solution was added, the mixture was stirred for 4 minutes, the solution was drained, and this operation was repeated once again.

(b) The carrier resin was washed with 600 μl of DMF for 1 minute, the solution was drained, and this operation was repeated 5 times.

(c) Fmoc-Leu-OH (165 μmol), HBTU (165 μmol), HOBt monohydrate (165 μmol), and DIEA (330 μmol) were stirred in DMF (660 μl) for 3 minutes, the obtained solution was added to the resin, the mixture was stirred for 60 minutes, and the solution was drained.

(d) The carrier resin was washed with 900 μl of DMF for 1 minute, the solution was drained, and this operation was repeated 5 times.

Fmoc-Leu-NH was synthesized on the carrier by the above-mentioned steps.

Next, Fmoc-Arg(Pmc)-Leu-NH was synthesized on the carrier through the steps (a) and (b), a condensation reaction using Fmoc-Arg(Pmc)-OH in step (c), and the washing step of (d).

A carrier resin bound with side-chain-protected peptides were obtained by repeating the steps (a) through (d) using Fmoc-Met-OH, Fmoc-Trp(Boc)-OH, Fmoc-Gly-OH, Fmoc-Arg(Pmc)-OH, Fmoc-Arg(Pmc)-OH, Fmoc-Leu-OH, Fmoc-Tyr(tBu)-OH, Fmoc-Asp(OtBu)-OH, Fmoc-Pro-OH, Fmoc-Gly-OH, Fmoc-Pro-OH, Fmoc-Ser(tBu)-OH, Fmoc-Pro-OH, Fmoc-Arg(Pmc)-OH, and Fmoc-Cys(Trt)-OH in order in the step (c); followed by the deprotection and washing steps of (a) and (b), washing with methanol and butyl ether in order, and then drying under reduced pressure for 12 hours. 1 ml of a mixed solution comprising TFA containing 2-methylindole at a concentration of 5 mg/mL (82.5%), thioanisole (5%), water (5%), ethyl methyl sulfide (3%), 1,2-ethanedithiol (2.5%), and thiophenol (2%) was added thereto, and was left standing at room temperature for 6 hours. Then the peptides were cleaved from the resin together with the removal of the side-chain protecting groups. After filtering off the resin, approximately 10 ml of ether were added to the obtained solution, the generated precipitates were collected by centrifugation and decantation, and 42.1 mg of crude peptide was obtained. This crude product was dissolved in aqueous acetic acid solution, and then passed through a cartridge filled with reverse-phase silica gel (YMC Dispo SPE C18) to adhere the peptides. Upon washing with an aqueous solution of 0.1% TFA and 15% acetonitrile and eluting with an aqueous solution of 0.1% TFA and 25% acetonitrile, a fraction containing compound 1 was obtained. This was freeze-dried, and 28.9 mg of compound 1 was obtained.

Mass spectrometry [FABMS]; m/z=2058.9 (M+H$^+$)

Amino acid analysis; Asx 1.0 (1), Ser 1.0 (1), Gly 2.0 (2), Arg 3.9 (4), Pro 2.9 (3), Tyr 1.0 (1), Met 1.0 (1), Leu 2.1 (2), Cys 1.2 (1)

(2) Synthesis of Compound 2 (a Peptide Comprising the Amino Acid Sequence Shown in SEQ ID NO: 24, H-Cys-Arg-Pro-Pro-Ala-Phe-Thr-Pro-Arg-Ala-Pro-Asp-Arg-Val-Thr-Ser-Ile-OH)

Using 30 mg of carrier resin (Wang resin, Novabiochem) bound with 14.4 μmol of Fmoc-Ile as the starting material, similarly to (1), Fmoc-Ser(tBu)-OH, Fmoc-Thr(tBu)-OH, Fmoc-Val-OH, Fmoc-Arg(Pmc)-OH, Fmoc-Asp(OtBu)-OH, Fmoc-Pro-OH, Fmoc-Ala-OH, Fmoc-Arg(Pmc)-OH, Fmoc-Pro-OH, Fmoc-Thr(tBu)-OH, Fmoc-Phe-OH, Fmoc-Ala-OH, Fmoc-Pro-OH, Fmoc-Pro-OH, Fmoc-Arg(Pmc)-OH, and Fmoc-Cys(Trt)-OH were condensed in order. Then upon removing Fmoc, washing, and drying, carrier resin bound with side-chain-protected peptides were obtained. 1 ml of a mixed solution comprising TFA (82.5%), thioanisole (5%), water (5%), ethyl methyl sulfide (3%), 1,2-ethanedithiol (2.5%), and thiophenol (2%) was added thereto, and was left standing at room temperature for 8 hours. Then the peptides were cleaved from the resin together with the removal of the side-chain protecting groups. After filtering off the resin, approximately 10 ml of ether were added to the obtained solution. The generated precipitates were collected by centrifugation and decantation, and 29.2 mg of crude peptide was obtained. This crude product was dissolved in aqueous acetic acid solution, and then passed through a cartridge filled with reverse-phase silica gel (YMC Dispo SPE C18) to adhere the peptides. Upon washing with an aqueous solution of 0.1% TFA and 10% acetonitrile, and eluting with an aqueous solution of 0.1% TFA and 25% acetonitrile, a fraction containing compound 2 was obtained. This was freeze-dried, and 24.5 mg of compound 2 was obtained.

Mass spectrometry [TOFMS]; m/z=1883.6 (M+H$^+$)

Amino acid analysis; Asx 1.0 (1), Ser 1.0 (1), Arg 3.0 (3), Thr 1.9 (2), Ala 2.1 (2), Pro 4.0 (4), Val 1.0 (1), Ile 1.0 (1), Phe 1.0 (1), Cys 1.3 (1)

(3) Synthesis of Compound 3 (a Peptide Comprising the Amino Acid Sequence Shown in SEQ ID NO: 25, H-Cys-Asn-Leu-Val-Pro-Glu-Glu-Glu-Ala-Glu-Ser-Glu-Glu-Asn-Asp-Asp-Tyr-Tyr-OH)

Using 30 mg of carrier resin (SynProPep Resin, Shimadzu) bound with 18 μmol of Fmoc-Tyr(tBu) as the starting material, similarly to (1), Fmoc-Asp(OtBu)-OH, Fmoc-Asp(OtBu)-OH, Fmoc-Asn(Trt)-OH, Fmoc-Glu(OtBu)-OH, Fmoc-Glu(OtBu)-OH, Fmoc-Ser(tBu)-OH, Fmoc-Glu(OtBu)-OH, Fmoc-Ala-OH, Fmoc-Glu(OtBu)-OH, Fmoc-Glu(OtBu)-OH, Fmoc-Glu(OtBu)-OH, Fmoc-Pro-OH, Fmoc-Val-OH, Fmoc-Leu-OH, Fmoc-Asn(Trt)-OH, and Fmoc-Cys(Trt)-OH were condensed in order. Upon removing Fmoc, washing, and drying, the carrier resin bound with side-chain-protected peptides were obtained. 1 ml of a mixed solution comprising TFA (90%), thioanisole (5%), and 1,2-ethanedithiol (5%), was added thereto, and was left standing at room temperature for 2 hours. Then the peptides were cleaved from the resin together with the removal of the side-chain protecting groups. After filtering off the resin, approximately 10 ml of ether were added to the obtained solution. The generated precipitates were collected by centrifugation and decantation, and 32.5 mg of crude peptide was obtained. This crude product was dissolved in a mixed solution comprising acetic acid, dithiothreitol, DMF, and water, and then passed through a cartridge filled with reverse-phase silica gel (YMC Dispo SPE C18) to adhere the peptides. Upon washing with an aqueous solution of 0.1% TFA and 10% acetonitrile, and eluting with an aqueous solution of 0.1% TFA and 25% acetonitrile, a fraction containing compound 3 was obtained. This was freeze-dried, and 17.1 mg of compound 3 was obtained.

Mass spectrometry [TOFMS]; m/z=2148 (M+H$^+$)

Amino acid analysis; Asx 4.0 (4), Glx 6.2 (6), Ser 1.0 (1), Ala 1.1 (1), Pro 1.0 (1), Tyr 1.8 (2), Val 0.9 (1), Leu 0.9 (1), Cys 1.0 (1)

Example 12

Production of Polyclonal Antibodies that Recognize Proteins Encoded by C-hsi13412 or C-kaia397

(1) Preparation of Immunogens

Conjugates of compound 2 and compound 3 obtained in Example 11 with KLH (Calbiochem) was prepared by the following method to raise immunogenicity, and were used as immunogens. More specifically, a 10 mg/ml solution was prepared by dissolving KLH in PBS, and 1/10 the volume of 25 mg/ml MBS (N-(m-Maleimidobenzoyloxy)succinimide: Nacalai Tesque) was added drop wise, and this was allowed to react while stirring for 30 minutes. Next, 2.5 mg of KLH-MB, which was obtained by removing free MBS using Sephadex G-25 column (Amersham Pharmacia) pre-equilibrated in PBS, was mixed with 1 mg of the peptide dissolved in 0.1 M sodium phosphate buffer (pH 7.0), and were allowed to react while stirring for 3 hours at room temperature. After the reaction, the product, which was dialyzed with PBS, was used as the immunogen.

(2) Immunization of Animals and Preparation of Antisera

100 μg each of KLH conjugates of compound 2 and compound 3 prepared in above (1) was administered to a 6 to 8 week old female BALB/c mouse, along with 2 mg of Aluminum hydroxide adjuvant (Antibodies-A Laboratory Manual, Cold Spring Harbor Laboratory, p99, 1988) and 1×10$^9$ cells of whooping-cough vaccine (Chiba Prefecture Serum Research Institute). Two weeks after the administration, 100 μg of each KLH conjugates was administered once a week, in total 4 times. Blood samples were collected from the carotid arteries of the mice, and antisera were prepared.

(3) Western Blotting Using Immunized Mouse Antisera

Using 5 μl each of cell lysates of COS-1/C-hsi13412 cell line and COS-1/C-kaia397 cell line obtained in Example 8 as samples of proteins encoded by C-hsi13412 and C-kaia397, Western Blotting was carried out according to Example 14, using 500 μl of the immunized mouse antisera obtained in above (2) as the detection antibody.

Figure 10:
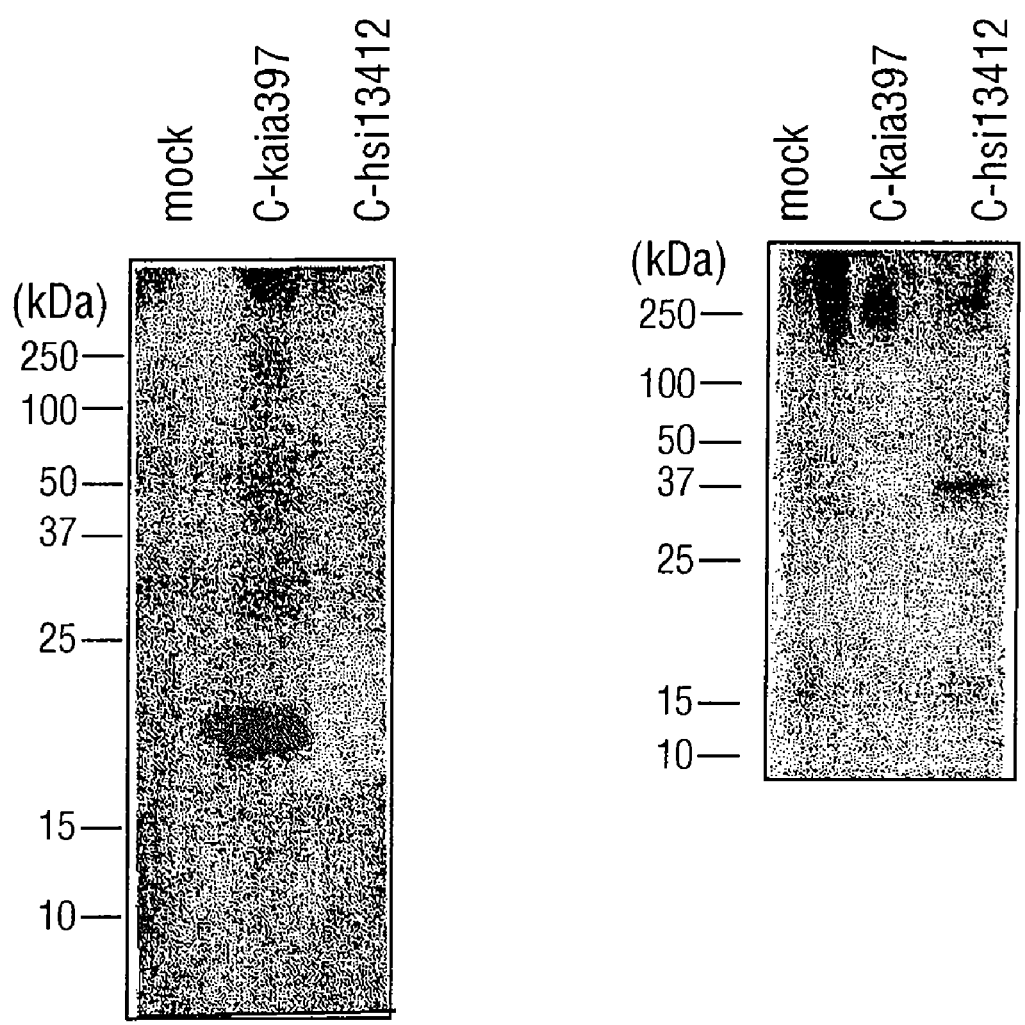
FIG. 10 shows the analysis by Western Blotting using polyclonal antibodies that recognize the proteins encoded by C-hsi13412 and C-kaia397. In the figure, the blotting on the right shows the results with antibodies that were obtained using compound 2 as its immunogen, and the blotting figure on the left shows the result with antibodies that were obtained using compound 3 as its immunogen.

The mouse antisera that were obtained using compound 2 and compound 3 as immunogens were confirmed to be able to specifically recognize proteins encoded by C-hsi13412 and C-kaia397, respectively (FIG. 10).

Example 13

Monoclonal Antibodies Recognizing Proteins Encoded by C-hsi13412 or C-kaia397

(1) Preparation of Immunogens

A conjugate of compound 1 obtained in Example 11 with KLH was prepared according to a method similar to Example 12(1), and was used as the immunogen.

(2) Immunization of Animals and Preparation of Antibody-Producing Cells

100 μg each of the KLH conjugate of compound 1 prepared in above (1) was administered to each of the three 6 to 8 week old female BALB/c mice, along with 2 mg of Aluminum hydroxide adjuvant (Antibodies-A Laboratory Manual, Cold Spring Harbor Laboratory, p 99, 1988) and 1×10$^9$ cells of whooping-cough vaccine (Chiba Prefecture Serum Research Institute). Two weeks after the administration, 100 μg each of the KLH conjugates were administered once a week, in total 4 times. Blood samples were collected from the carotid arteries of the mice, their blood serum antibody titers were examined by enzyme immunoassay method shown below, and the spleen was excised from mice indicating sufficient antibody titers 3 days after final immunization.

The excised spleen was fragmented in MEM (Minimum Essential Medium, NISSUI PHARMACEUTICAL), loosened with tweezers, and then centrifuged (250×g, 5 minutes). Tris-Ammonium chloride buffer (pH 7.6) was added to the obtained precipitate fraction, and upon treatment for 1 to 2 minutes, red blood cells were removed. The obtained precipitate fraction (cell fraction) was washed 3 times in MEM, and was used for cell fusion.

(3) Enzyme Immunoassay (Binding ELISA)

Compound 1 obtained in Example 11 that was conjugated with thyroglobulin (hereinafter, referred to as "THY") was used as an antigen for assays. The production method was carried out similarly to Example 12, except using SMCC (4-(N-Maleimidomethyl)-cyclohexane-1-carboxylic acid N-hydroxysuccinimido ester; Sigma) instead of MBS as the crosslinking agent. For adhesion, 50 μl/well aliquots of the conjugate (10 μg/ml) prepared as mentioned above were dispensed into a 96-well EIA plate (Greiner), and were left standing overnight at 4° C. After washing the plate, the remaining active groups were blocked by adding 100 μl/well aliquots of 1% bovine serum albumin (hereinafter, referred to as "BSA")/Dulbecco's phosphate buffer (Phosphate buffered saline: PBS), and leaving standing at room temperature for 1 hour.

After leaving standing for 1 hour, 1% BSA/PBS was discarded, 50 μl/well aliquots of immunized mouse antisera, culture supernatant of monoclonal antibodies, or purified monoclonal antibodies were dispensed into the plate, and were left standing for another 2 hours. This plate was washed with 0.05% polyoxyethylene (20) sorbitan monolaurate (product name: Span 20 (corresponding ICI trademarked product Tween 20: Wako))/PBS (hereinafter, abbreviated as "Tween-PBS"). Then ABTS substrate solution (2,2-azinobis (3-ethylbenzothiazol-6-sulfonic acid) ammonium, 1 mM ABTS/0.1 M citric acid buffer (pH 4.2)) was added to develop colors, and the absorbance at OD415 nm was measured using plate reader (Emax; Molecular Devices).

(4) Preparation of Mouse Myeloma Cells

By culturing 8-Azaguanine-resistant mouse myeloma cell line P3X63Ag8U.1 (P3-U1: purchased from ATCC) in normal medium (RPMI medium containing 10% fetal calf serum (hereinafter, abbreviated as "FCS")) $2 \times 10^7$ or more cells were obtained, and were used as a parent cell line for cell fusion.

(5) Production of Hybridomas

Mouse splenocytes obtained in above (2) and the myeloma cells obtained in above (4) were mixed at a ratio of 10:1, and the mixture was centrifuged (250× g, 5 minutes). The cell population of the obtained precipitate fraction was loosened well; then, while stirring, 0.5 ml of a mixed solution containing 2 g of polyethylene glycol-1000 (PEG-1000), 2 ml of MEM, and 0.7 ml of dimethyl sulfoxide was added at 37° C. for every 108 mouse splenocytes. After 1 ml each of MEM was added to the suspension several times every 1 to 2 minutes, MEM was added so that the total volume becomes 50 ml.

The suspension was centrifuged (900 rpm, 5 minutes), and after gently loosening the cells of the obtained precipitate fraction, the cells were suspended into 100 ml of HAT media (a 10% FCS-added RPMI media supplemented with HAT/Media Supplement (Roche Diagnostics)) by gentle pipetting with a graduated pipette. 200 μl/well aliquots of the suspension were dispensed into the 96-well culture plate, and were cultured for 10 to 14 days at 37° C. in a 5% $CO_2$ incubator.

Figure 14:
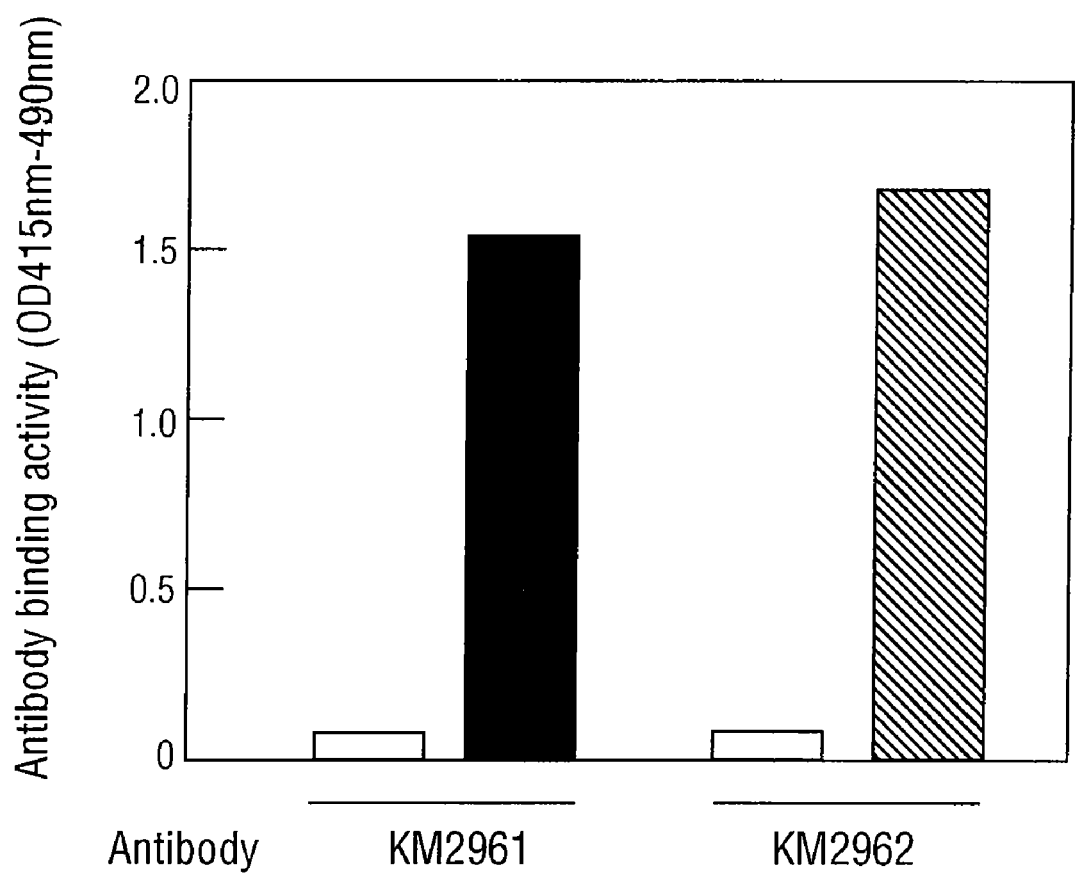
FIG. 14 shows the binding activity against the antigenic peptides of KM2961 and KM2962. In the figure, KM2961 represents the culture supernatant obtained by cultivating, for 3 days, hybridomas that produce the monoclonal antibody KM2961; and KM2961 represents the culture supernatant obtained by cultivating, for 3 days, hybridomas that produce the monoclonal antibody KM2961. The white columns show the reactions between these culture supernatants and plates that are not coated with the antigenic peptides, and the black and shaded columns show the reactions of these culture supernatants with plates coated with the antigenic peptides.

After cultivation, the culture supernatant was examined by the enzyme immunoassay method of (3) mentioned above, and wells that react to the antigenic peptide but not to the control peptide were selected. Using cells included in the selected wells, cloning by the limiting dilution method was repeated twice, and anti-C-hsi13412/C-kaia397 monoclonal antibody-producing hybridoma was established. As a result, using compound 1 as the antigen, two types of anti-C-hsi13412/C-kaia397 monoclonal antibodies, KM2961 and KM2962, were obtained. KM2961 and KM2962 specifically reacted with compound 1, which is the antigenic peptide (FIG. 14).

Hybridoma cell lines that produce anti-C-hsi13412/C-kaia397 monoclonal antibodies, KM2961 and KM2962, have been deposited under the accession numbers FERM BP-7603 and FERM BP-7604, respectively, in the National Institute of Advanced Industrial Science and Technology, Patent Microorganism Depository (AIST Tsukuba Central 6, 1-1-1 Higashi, Tsukuba, Ibaraki, Japan: postal code 305-8366) on May 24, 2001.

(6) Purification of Monoclonal Antibodies

The hybridoma cell lines obtained in (5) mentioned above were injected intraperitoneally at 5 to $20 \times 10^6$ cells/mouse to each pristane-treated 8-week nude female mice (BALC/c). 10 to 21 days after the injection, ascites (1 to 8 ml/mouse) were collected from mice wherein ascites had accumulated due to the formation of ascites carcinoma from the hybridomas.

The ascites were centrifuged (1200×g, 5 minutes), and the solids were removed. The purified IgG monoclonal antibodies were obtained by purification using the caprylic acid precipitation method (Antibodies—A Laboratory Manual, Cold Spring Harbor Laboratory, 1988). The subclasses of the monoclonal antibodies were determined to be IgG1 for KM2961 and IgG3 for KM2962 by the ELISA method using subclass typing kit.

Example 14

Detection of Proteins Encoded by C-hsi13412 or C-kaia397 by Western Blotting Using KM2961 and KM2962

2.5 μl/lane of the cell lysates and 10 μl/lane of the culture supernatant of COS-1/mock cell line, COS-1/C-hsi13412 cell line, and COS-1/C-kaia397 cell line prepared in Example 8 were fractionated by 15% SDS-polyacrylamide gel electrophoresis (Antibodies—A Laboratory Manual, Cold Spring Harbor Laboratory, 1988), and then was blotted onto a PVDF membrane (Millipore) according to a conventional method. After blocking the membrane with 5% skim milk-PBS (hereinafter, referred to as "blocking solution"), anti-C-hsi3412/C-kaia397 monoclonal antibody, KM2961 or KM2962 was added to the membrane at a concentration of 2 μg/ml, and was left standing at room temperature for 1 hour. After washing the membrane well with Tween-TBS, detection was carried out using peroxidase-labeled rabbit anti-mouse immunoglobulin (DAKO) diluted 2,000 times as the secondary antibody.

Figure 11:
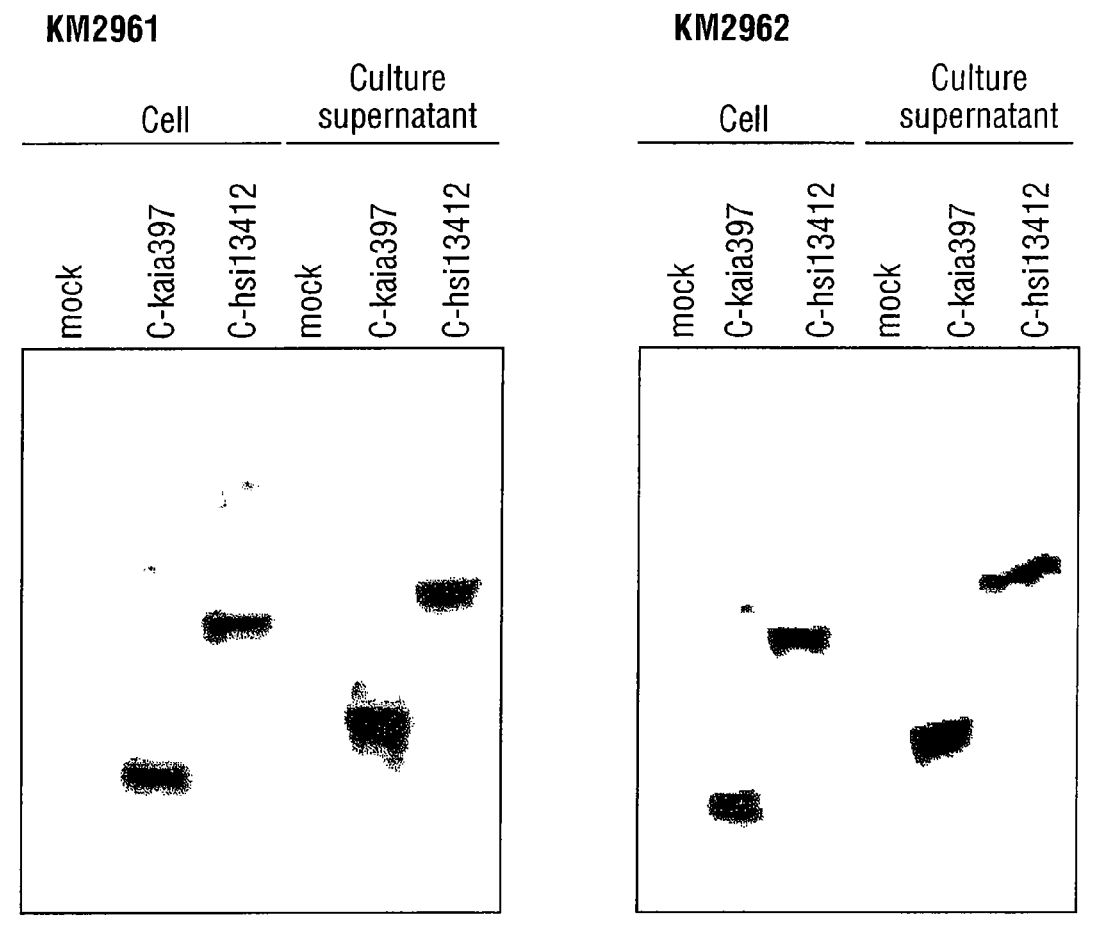

The anti-C-hsi13412/C-kaia397 monoclonal antibody KM2961 and KM2962 were found to specifically recognize proteins encoded by C-hsi13412 or C-kaia397 expressed in COS-1 cells of Example 8 (FIG. 11).

Example 15

Binding of IGF and Proteins Encoded by C-hsi13412 or C-kaia397

To investigate the binding affinity of the proteins encoded by C-hsi13412 and C-kaia397 to IGF, analysis by far-Western (Molecular Cloning—A Laboratory Manual, Third Edition, Cold Spring Harbor Laboratory; Protein Experiment Protocol 1, Shujunsha) was carried out using the cell lysates of COS-1/C-hsi13412 cell line, COS-1/C-kaia397, and, as a control, COS-1/mock cell line obtained in Example 8.

A 5 μl aliquot of the cell lysates of COS-1/mock cell line, COS-1/C-hsi13412 cell line, and COS-1/C-kaia397 cell line was placed into each lane, and according to Example 14, SDS-PAGE was carried out, transferred to a PVDF membrane, and then blocked. Subsequently, 2 μg/ml human IGF-I (Peprotech), 2 μg/ml human IGF-II (Peprotech), or 2 μg/ml of human insulin (Sigma) diluted with the blocking solution was enclosed with the membrane, and was allowed to react at room temperature overnight. Next, anti-human IGF-I monoclonal antibody (Upstate Biotechnology), anti-human IGF-II monoclonal antibody (Upstate Biotechnology), or anti-human insulin polyclonal antibody (Santa Cruz) were added to each of the membranes to a concentration of 2 μg/ml, and was left standing at room temperature for 1 hour. After the membrane was washed well with Tween-TBS, detection was carried out using peroxidase-labeled rabbit anti-mouse immunoglobulin (DAKO) diluted 2,000 times as the secondary antibody.

Figure 12:
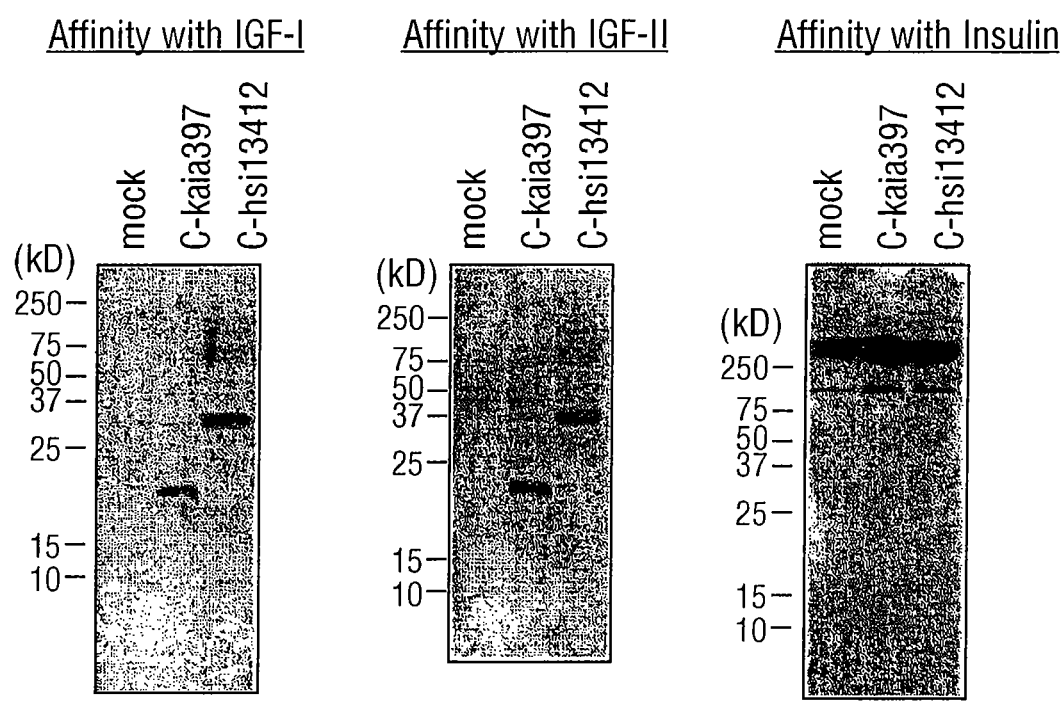
FIG. 12 shows the binding affinity of IGF to the proteins encoded by C-hsi13412 or C-kaia397 by far-Western. Mock represents the control.

With the anti-IGF-I antibody and anti-IGF-II antibody, bands of a molecular weight of approximately 33 kDa and approximately 22 kDa derived from proteins encoded by C-hsi13412 and C-kaia397, respectively, were detected. However, when anti-insulin antibody was used, these bands were not detected. Therefore, the proteins encoded by C-hsi13412 or C-kaia397 were suggested to bind to IGF-I and IGF-II, but not to insulin (FIG. 12).

Example 16

Effects of Proteins Encoded by C-hsi13412 or C-kaia397 on Cancer Cells

To investigate the action of C-hsi13412 and C-kaia397 on cancer cell growth, effects on IGF-dependent growth of human colon cancer cell line HT-29 (ATCC HTB-38) were examined as described below using the culture supernatants of COS-1/mock cell line, COS-1/C-hsi13412 cell line, and COS-1/C-kaia397 cell line obtained in Example 8.

50 μl/well of HT-29 cells that were prepared at a concentration of $1 \times 10^5$ cells/ml in D-MEM/F-12 medium (Gibco) supplemented with 200 μg/ml of bovine serum albumin (Gibco), 10 μg/ml of human transferrin (Gibco), 50 units/ml penicillin (Gibco), and 50 μg/ml of streptomycin (Gibco), were plated onto a 96-well plate. Cultivation was carried out at 37° C. in a $CO_2$ incubator for 3 hours. Next, human IGF-I (Peprotech) or human IGF-II (Peprotech) each at a final concentration of 0.1 ng/ml was added thereto. Subsequently, 5 μl/well of the culture supernatant of COS-1/mock cell line, COS-1/C-hsi13412 cell line, or COS-1/C-kaia397 cell line was added thereto. After cultivating at 37° C. in a $CO_2$ incubator for an additional 3 days, viable cells were counted using Cell Proliferation Reagent WST-1 (Roche Diagnostics).

The culture supernatants of COS-1/C-hsi13412 cell line and COS-1/C-kaia397 cell line were shown to inhibit IGF-dependent growth of human colon cancer cell line HT-29 cells (FIG. 13).

INDUSTRIAL APPLICABILITY

According to the present invention, novel insulin-like growth factor binding proteins, DNAs encoding the proteins, and antibodies recognizing the proteins, as well as determination methods, diagnostic agents, preventive agents, and therapeutic agents for diseases associated with the proteins can be provided.

What is claimed is:

1. An isolated antibody that binds to a polypeptide consisting of the 171st to the 197th amino acid residues in the amino acid sequence represented by SEQ ID NO: 2.

2. A method for producing the antibody of claim 1, wherein a polypeptide comprising an amino acid sequence that includes at least 5 or more continuous amino acids of the 171st to the 197th amino acid residues in the amino acid sequence represented by SEQ ID NO: 2 is used as an antigen.

3. An antibody obtained by the method of claim 2.

4. A method for immunologically detecting or quantifying an insulin-like growth factor binding protein, the method comprising contacting a sample suspected of comprising the protein with the antibody of claim 1, and immunologically detecting or quantifying the protein.

5. A medicament containing the antibody according to claim 1.

6. The antibody according to claim 1, wherein the antibody does not recognize an insulin-like growth factor binding protein which comprises the amino acid sequence represented by SEQ ID NO: 1.

7. A monoclonal antibody produced by a hybridoma with the accession number FERM BP-7604.

8. A method for immunologically detecting or quantifying an insulin-like growth factor binding protein, the method comprising contacting a sample suspected of comprising the protein with a monoclonal antibody produced by a hybridoma with the accession number FERM BP-7604, and immunologically detecting or quantifying the protein.

9. A medicament containing a monoclonal antibody produced by a hybridoma with the accession number FERM BP-7604.

* * * * *

SEQUENCE LISTING

```
<160> NUMBER OF SEQ ID NOS: 35

<210> SEQ ID NO 1
<211> LENGTH: 304
<212> TYPE: PRT
<213> ORGANISM: Homo sapiens
<220> FEATURE:
<223> OTHER INFORMATION: C-hsi13412

<400> SEQUENCE: 1

Met Leu Pro Pro Arg Pro Ala Ala Leu Ala Leu Pro Val Leu
 1               5                  10                  15

Leu Leu Leu Leu Val Val Leu Thr Pro Pro Thr Gly Ala Arg Pro
              20                  25                  30

Ser Pro Gly Pro Asp Tyr Leu Arg Arg Gly Trp Met Arg Leu Leu Ala
         35                  40                      45

Glu Gly Glu Gly Cys Ala Pro Cys Arg Pro Glu Glu Cys Ala Ala Pro
     50                  55                      60

Arg Gly Cys Leu Ala Gly Arg Val Arg Asp Ala Gly Gly Cys Cys Trp
 65                  70                      75                  80

Glu Cys Ala Asn Leu Glu Gly Gln Leu Cys Asp Leu Asp Pro Ser Ala
                 85                      90                  95

His Phe Tyr Gly His Cys Gly Glu Gln Leu Glu Cys Arg Leu Asp Thr
            100                     105                 110

Gly Gly Asp Leu Ser Arg Gly Glu Val Pro Glu Pro Leu Cys Ala Cys
        115                     120                 125

Arg Ser Gln Ser Pro Leu Cys Gly Ser Asp Gly His Thr Tyr Ser Gln
    130                     135                 140

Ile Cys Arg Leu Gln Glu Ala Ala Arg Ala Arg Pro Asp Ala Asn Leu
```

-continued

```
            145                 150                 155                 160

Thr Val Ala His Pro Gly Pro Cys Glu Ser Gly Pro Gln Ile Val Ser
                165                 170                 175

His Pro Tyr Asp Thr Trp Asn Val Thr Gly Gln Asp Val Ile Phe Gly
            180                 185                 190

Cys Glu Val Phe Ala Tyr Pro Met Ala Ser Ile Glu Trp Arg Lys Asp
                195                 200                 205

Gly Leu Asp Ile Gln Leu Pro Gly Asp Pro His Ile Ser Val Gln
            210                 215                 220

Phe Arg Gly Gly Pro Gln Arg Phe Glu Val Thr Gly Trp Leu Gln Ile
225                 230                 235                 240

Gln Ala Val Arg Pro Ser Asp Glu Gly Thr Tyr Arg Cys Leu Gly Arg
                245                 250                 255

Asn Ala Leu Gly Gln Val Glu Ala Pro Ala Ser Leu Thr Val Leu Thr
            260                 265                 270

Pro Asp Gln Leu Asn Ser Thr Gly Ile Pro Gln Leu Arg Ser Leu Asn
            275                 280                 285

Leu Val Pro Glu Glu Glu Ala Glu Ser Glu Glu Asn Asp Asp Tyr Tyr
290                 295                 300

<210> SEQ ID NO 2
<211> LENGTH: 197
<212> TYPE: PRT
<213> ORGANISM: Homo sapiens
<220> FEATURE:
<223> OTHER INFORMATION: C-kaia397

<400> SEQUENCE: 2

Met Leu Pro Pro Pro Arg Pro Ala Ala Ala Leu Ala Leu Pro Val Leu
1               5                   10                  15

Leu Leu Leu Leu Val Val Leu Thr Pro Pro Thr Gly Ala Arg Pro
            20                  25                  30

Ser Pro Gly Pro Asp Tyr Leu Arg Arg Gly Trp Met Arg Leu Leu Ala
            35                  40                  45

Glu Gly Glu Gly Cys Ala Pro Cys Arg Pro Glu Cys Ala Ala Pro
        50                  55                  60

Arg Gly Cys Leu Ala Gly Arg Val Arg Asp Ala Gly Gly Cys Cys Trp
65                  70                  75                  80

Glu Cys Ala Asn Leu Glu Gly Gln Leu Cys Asp Leu Asp Pro Ser Ala
                85                  90                  95

His Phe Tyr Gly His Cys Gly Glu Gln Leu Glu Cys Arg Leu Asp Thr
            100                 105                 110

Gly Gly Asp Leu Ser Arg Gly Glu Val Pro Glu Pro Leu Cys Ala Cys
            115                 120                 125

Arg Ser Gln Ser Pro Leu Cys Gly Ser Asp Gly His Thr Tyr Ser Gln
        130                 135                 140

Ile Cys Arg Leu Gln Glu Ala Ala Arg Ala Arg Pro Asp Ala Asn Leu
145                 150                 155                 160

Thr Val Ala His Pro Gly Pro Cys Glu Ser Asp Trp Met Pro Leu Leu
                165                 170                 175

Gly His Ala Ile Leu Arg Pro Pro Ala Phe Thr Pro Arg Ala Pro Asp
            180                 185                 190

Arg Val Thr Ser Ile
        195
```

<210> SEQ ID NO 3
<211> LENGTH: 1772
<212> TYPE: DNA
<213> ORGANISM: Homo sapiens
<220> FEATURE:
<221> NAME/KEY: CDS
<222> LOCATION: (177)..(1091)
<223> OTHER INFORMATION: C-hsi13412

<400> SEQUENCE: 3

| | | | | | |
|---|---|---|---|---|---|
| aagtcctcag | gacggagcag | aggtggccgg | cgggcccggc | tgactgcgcc | tctgctttct | 60 |
| ttccataacc | ttttctttcg | gactcgaatc | acggctgctg | cgaagggtct | agttccggac | 120 |
| actagggtgc | ccgaacgcgc | tgatgccccg | agtgctcgca | gggcttcccg | ctaaccatgc | 180 |
| tgccgccgcc | gcggcccgca | gctgccttgg | cgctgcctgt | gctcctgcta | ctgctggtgg | 240 |
| tgctgacgcc | gcccccgacc | ggcgcaaggc | catccccagg | cccagattac | ctgcggcgcg | 300 |
| gctggatgcg | gctgctagcg | gagggcgagg | gctgcgctcc | ctgccggcca | gaagagtgcg | 360 |
| ccgcgccgcg | gggctgcctg | gcgggcaggg | tgcgcgacgc | gggcggctgc | tgctgggaat | 420 |
| gcgccaacct | cgagggccag | ctctgcgacc | tggaccccag | tgctcacttc | tacgggcact | 480 |
| gcggcgagca | gcttgagtgc | cggctggaca | caggcggcga | cctgagccgc | ggagaggtgc | 540 |
| cggaacctct | gtgtgcctgt | cgttcgcaga | gtccgctctg | cgggtccgac | ggtcacacct | 600 |
| actcccagat | ctgccgcctg | caggaggcgg | cccgcgctcg | gccgatgcc | aacctcactg | 660 |
| tggcacaccc | ggggccctgc | gaatcggggc | cccagatcgt | gtcacatcca | tatgacactt | 720 |
| ggaatgtgac | agggcaggat | gtgatctttg | gctgtgaagt | gtttgcctac | cccatggcct | 780 |
| ccatcgagtg | gaggaaggat | ggcttggaca | tccagctgcc | aggggatgac | ccccacatct | 840 |
| ctgtgcagtt | taggggtgga | ccccagaggt | ttgaggtgac | tggctggctg | cagatccagg | 900 |
| ctgtgcgtcc | cagtgatgag | ggcacttacc | gctgccttgg | ccgcaatgcc | ctgggtcaag | 960 |
| tggaggcccc | tgctagcttg | acagtgctca | cacctgacca | gctgaactct | acaggcatcc | 1020 |
| cccagctgcg | atcactaaac | ctggttcctg | aggaggagc | tgagagtgaa | gagaatgacg | 1080 |
| attactacta | ggtccagagc | tctggcccat | gggggtgggt | gagcggctat | agtgttcatc | 1140 |
| cctgctcttg | aaaagacctg | gaaaggggag | cagggtccct | tcatcgactg | ctttcatgct | 1200 |
| gtcagtaggg | atgatcatgg | gaggcctatt | tgactccaag | gtagcagtgt | ggtaggatag | 1260 |
| agacaaaagc | tggaggaggg | tagggagaga | agctgagacc | aggaccggtg | gggtacaaag | 1320 |
| gggcccatgc | aggagatgcc | ctggccagta | ggacctccaa | caggttgttt | cccaggctgg | 1380 |
| ggtgggggcc | tgagcagaca | cagaggtgca | ggcaccagga | ttctccactt | cttccagccc | 1440 |
| tgctgggcca | cagttctaac | tgcccttcct | cccaggccct | ggttcttgct | atttcctggt | 1500 |
| ccccaacgtt | tatctagctt | gtttgccctt | tccccaaact | catcttccag | aacttttccc | 1560 |
| tctctcctaa | gccccagttg | cacctactaa | ctgcagtccc | ttttgctgtc | tgccgtcttt | 1620 |
| tgtacaagag | agagaacagc | ggagcatgac | ttagttcagt | gcagagagat | aggtgaggcc | 1680 |
| agctcgagat | cttataccac | tctgtattgg | acaaaggcta | gcacagggct | aggcaccaat | 1740 |
| aaagatttct | aatgaaaaaa | aaaaaaaaaa | aa | | | 1772 |

<210> SEQ ID NO 4
<211> LENGTH: 2698
<212> TYPE: DNA
<213> ORGANISM: Homo sapiens
<220> FEATURE:
<221> NAME/KEY: CDS
<222> LOCATION: (926)..(1519)

<223> OTHER INFORMATION: C-kaia397

<400> SEQUENCE: 4

| | | | | | |
|---|---|---|---|---|---|
| aaagtgccac | ggtggcggtg | gtggcggccg | cgaggccgag | tgtctccggc | cctgccagcc | 60 |
| tcgcaaccgt | aacctgtaat | cccgacccga | gggacgcccg | ccggggaggc | gccagcccgc | 120 |
| ctctccctgc | ggccgctggt | cggctccgac | ctcgaatcac | ccggctcacc | cgcgggtcgc | 180 |
| agcacctgcc | ggatgtgggg | aggaagaagg | aggccagatg | agggaaggcg | gatgtaggcg | 240 |
| cccagtctgt | ccgcgccttg | gtggggcagc | tgggtgggca | agcctgcggt | cgctcccggg | 300 |
| aaccagccct | gggctgcggg | gagacgaagg | tggttggtcc | tgccctccag | gagcgccccg | 360 |
| acatcgacgt | aaaatgactt | ggcaccagag | ctcctgccgc | ctccccctta | tgcagctgcc | 420 |
| ctcgccgacg | ccagggactg | taaaatcaga | tgggacaggg | cctagccgtt | cagccaacac | 480 |
| tttgagcttc | ccagccaaac | tcctaccccc | actccccgcc | tccggtcctc | acccccttcc | 540 |
| tctctcccag | cctcggtgtc | tggttacggc | tcctctgctc | gcattgtgac | tttgggccag | 600 |
| gctgggggaa | atgacccggg | agggtcccat | gcggctacat | aaaattggca | gccttagaac | 660 |
| tagtgggaag | gcgggtgcgc | gaagtcgagg | ggcggagaga | gggggccgga | ggagctgctt | 720 |
| tctgaatcca | agttcgtggg | ctctctcaga | agtcctcagg | acggagcaga | ggtggccggc | 780 |
| gggcccggct | gactgcgcct | ctgctttctt | tccataacct | tttctttcgg | actcgaatca | 840 |
| cggctgctgc | gaagggtcta | gttccggaca | ctagggtgcc | cgaacgcgct | gatgccccga | 900 |
| gtgctcgcag | ggcttcccgc | taaccatgct | gccgccgccg | cggcccgcag | ctgccttggc | 960 |
| gctgctgtg | ctcctgctac | tgctggtggt | gctgacgccg | ccccgaccg | gcgcaaggcc | 1020 |
| atccccaggc | ccagattacc | tgcggcgcgc | ctggatgcgg | ctgctagcgg | agggcgaggg | 1080 |
| ctgcgctccc | tgccggccag | aagagtgcgc | cgcgccgcgg | ggctgcctgg | cgggcagggt | 1140 |
| gcgcgacgcg | ggcggctgct | gctgggaatg | cgccaacctc | gagggccagc | tctgcgacct | 1200 |
| ggaccccagt | gctcacttct | acgggcactg | cggcgagcag | cttgagtgcc | ggctggacac | 1260 |
| aggcggcgac | ctgagccgcg | gagaggtgcc | ggaacctctg | tgtgcctgtc | gttcgcagag | 1320 |
| tccgctctgc | gggtccgacg | gtcacaccta | ctcccagatc | tgccgcctgc | aggaggcggc | 1380 |
| ccgcgctcgg | cccgatgcca | acctcactgt | ggcacacccg | gggccctgcg | aatcggactg | 1440 |
| gatgcctttg | ctgggccatg | ctattctcag | acctcccgcc | ttcaccccca | gggccccaga | 1500 |
| tcgtgtcaca | tccatatgac | acttggaatg | tgacagggca | ggatgtgatc | tttggctgtg | 1560 |
| aagtgtttgc | ctaccccatg | gcctccatcg | agtggaggaa | ggatggcttg | acatccagc | 1620 |
| tgccagggga | tgacccccac | atctctgtgc | agtttagggg | tggaccccag | aggtttgagg | 1680 |
| tgactggctg | gctgcagatc | caggctgtgc | gtcccagtga | tgagggcact | taccgctgcc | 1740 |
| ttggccgcaa | tgccctgggt | caagtggagg | cccctgctag | cttgacagtg | ctcacacctg | 1800 |
| accagctgaa | ctctacaggc | atcccccagc | tgcgatcact | aaacctggtt | cctgaggagg | 1860 |
| aggctgagag | tgaagagaat | gacgattact | actaggtcca | gagctctggc | ccatggggt | 1920 |
| tgctcacacc | cgagatgtga | ggttccagga | gcgccgaccc | agagttgcca | ggcctgaagg | 1980 |
| cgggagaggc | tcagtcgcac | cctacatttc | ccacctccaa | gattttaagt | atagttcgct | 2040 |
| tgaaatccct | ggaatgcgct | ttcttctggc | tcctacccgg | agatccggag | tccggacaaa | 2100 |
| ccggggcagg | aggggtccgt | cggaccagct | cctcccaagc | cgaggcttcc | aggtctcggc | 2160 |
| cgggctcttc | tccctgcttt | tagctgagcc | gggctgggcg | tacctctctc | ctccatctag | 2220 |
| agcagggtgt | gaagaggaag | ccagaggggg | ctgtctgaaa | atgaccctga | ccccctcctc | 2280 |

```
gggctgtcgt gaggaggagg gccgcttcgc ccggctgctc gtcaccgcga aggctccaaa    2340
gaagtgttgc gcagccgtgc tggtataact gagggtgtcc tggcgaagcc cagcccctgg    2400
cgccctggtg accgggggg tcgatgtgcg gactgggcag aactggagcc cgaagctgga    2460
gagcgcccct caaaaagaag cctgggggga tggcgcgggc ggtggcgtgc ggggaagcgc    2520
ctggggaaca cctggctctg caagttttgt gccttagcgg aaagaggcga catctctggc    2580
aagttgggag tacaggaagt agcgaaggag tgccatctgg tggatccttc tggtagtgac    2640
actcagacct gggccagggg ccttgagaca atttacttga ctggaaaaat ctaaaaaa     2698
```

```
<210> SEQ ID NO 5
<211> LENGTH: 30
<212> TYPE: RNA
<213> ORGANISM: Artificial Sequence
<220> FEATURE:
<223> OTHER INFORMATION: Description of Artificial Sequence:oligo-cap
      linker

<400> SEQUENCE: 5
agcaucgagu cggccuuguu ggccuacugg                                    30

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence:oligo dT
      primer

<400> SEQUENCE: 6
gcggctgaag acggcctatg tggcctttt ttttttttt tt                        42

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:5' end sense
      PCR primer

<400> SEQUENCE: 7
agcatcgagt cggccttgtt g                                             21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:3' end
      antisense PCR primer

<400> SEQUENCE: 8
gcggctgaag acggcctatg t                                             21

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:
      oligonucleotide PCR primer specific for C-hsi13412, PCR primer
      based on sequence common between coding regions of
      C-hsi13412 and C-kaia397

<400> SEQUENCE: 9
```
aatgcgccaa cctcgaggg                                              19

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:
      oligonucleotide PCR primer specific for C-hsi13412

<400> SEQUENCE: 10
aagagcaggg atgaacacta tag                                         23

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:
      oligonucleotide PCR primer specific for C-hsi13412

<400> SEQUENCE: 11
ggcgggaggt ctgagaatag catgg                                       25

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:
      oligonucleotide PCR primer specific for C-hsi13412

<400> SEQUENCE: 12
cctcgccttt gccgatcc                                               18

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:
      oligonucleotide PCR primer specific for C-hsi13412

<400> SEQUENCE: 13
ggatcttcat gaggtagtca gtc                                         23

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:PCR primer
      based on sequence common between coding regions of
      C-hsi13412 and C-kaia397

<400> SEQUENCE: 14
cctgtcacat tccaagtgtc                                             20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:PCR primer
      designed for FLAG marker peptide added to
      C-terminus of C-hsi13412 and C-kaia397

-continued

```
<400> SEQUENCE: 15
ttcccgctaa ccatgctgc                                                  19

<210> SEQ ID NO 16
<211> LENGTH: 54
<212> TYPE: DNA
<213> ORGANISM: Artificial Sequence
<220> FEATURE:
<223> OTHER INFORMATION: Description of Artificial Sequence:PCR primer
      designed for FLAG marker peptide added to
      C-terminus of C-hsi13412

<400> SEQUENCE: 16
tcattacttg tcatcgtcat ccttgtagtc gtagtaatcg tcattctctt cact           54

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence:PCR primer
      designed for FLAG marker peptide added to
      C-terminus of C-kaia397

<400> SEQUENCE: 17
tcattacttg tcatcgtcat ccttgtagtc tatggatgtg acacgatctg ggc            54

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 18
aaaaagcttg ccaccatgct gccgccgccg cggcc                                35

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 19
ttttctagat tactagtagt aatcgtcatt ctc                                  33

<210> SEQ ID NO 20
<211> LENGTH: 69
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 20
ttttctagat tactagtgat ggtgatggtg atgcttatcg tcatcgtcgt agtaatcgtc     60
attctcttc                                                             69

<210> SEQ ID NO 21
<211> LENGTH: 33
<212> TYPE: DNA
<213> ORGANISM: Artificial Sequence
<220> FEATURE:
```

-continued

```
<223> OTHER INFORMATION: Description of Artificial Sequence:
      oligonucleotide primer

<400> SEQUENCE: 21
ttttctagat tatcatatgg atgtgacacg atc                                    33

<210> SEQ ID NO 22
<211> LENGTH: 69
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 22
ttttctagat tatcagtgat ggtgatggtg atgcttatcg tcatcgtcta tggatgtgac       60
acgatctgg                                                              69

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence:compound 1
<220> FEATURE:
<221> NAME/KEY: MOD_RES
<222> LOCATION: (17)
<223> OTHER INFORMATION: Xaa = leucinamide

<400> SEQUENCE: 23

Cys Arg Pro Ser Pro Gly Pro Asp Tyr Leu Arg Arg Gly Trp Met Arg
 1               5                  10                  15

Xaa

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence:compound 2

<400> SEQUENCE: 24

Cys Arg Pro Pro Ala Phe Thr Pro Arg Ala Pro Asp Arg Val Thr Ser
 1               5                  10                  15

Ile

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence:compound 3

<400> SEQUENCE: 25

Cys Asn Leu Val Pro Glu Glu Glu Ala Glu Ser Glu Glu Asn Asp Asp
 1               5                  10                  15

Tyr Tyr

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence:insulin-like
      growth factor binding motif (IGFBP motif)
```

```
<220> FEATURE:
<221> NAME/KEY: MOD_RES
<222> LOCATION: (6)..(7)
<223> OTHER INFORMATION: Xaa = an arbitrary amino acid

<400> SEQUENCE: 26

Gly Cys Gly Cys Cys Xaa Xaa Cys
 1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence:sequence
      similar to IGFBP motif

<400> SEQUENCE: 27

Ala Gly Gly Cys Cys Trp Glu Cys
 1               5

<210> SEQ ID NO 28
<211> LENGTH: 78
<212> TYPE: PRT
<213> ORGANISM: Homo sapiens
<220> FEATURE:
<223> OTHER INFORMATION: IGFBP1

<400> SEQUENCE: 28

Met Ser Glu Val Pro Val Ala Arg Val Trp Leu Val Leu Leu Leu Leu
 1               5                  10                  15

Thr Val Gln Val Gly Val Thr Ala Gly Ala Pro Trp Gln Cys Ala Pro
                20                  25                  30

Cys Ser Ala Glu Lys Leu Ala Leu Cys Pro Pro Val Ser Ala Ser Cys
            35                  40                  45

Ser Glu Val Thr Arg Ser Ala Gly Cys Gly Cys Pro Met Cys Ala
        50                  55                  60

Leu Pro Leu Gly Ala Ala Cys Gly Val Ala Thr Ala Arg Cys
 65                  70                  75

<210> SEQ ID NO 29
<211> LENGTH: 108
<212> TYPE: PRT
<213> ORGANISM: Homo sapiens
<220> FEATURE:
<223> OTHER INFORMATION: IGFBP2

<400> SEQUENCE: 29

Met Leu Pro Arg Val Gly Cys Pro Ala Leu Pro Leu Pro Pro Pro
 1               5                  10                  15

Leu Leu Pro Leu Leu Pro Leu Leu Leu Leu Leu Gly Ala Ser Gly
                20                  25                  30

Gly Gly Gly Gly Ala Arg Ala Glu Val Leu Phe Arg Cys Pro Pro Cys
            35                  40                  45

Thr Pro Glu Arg Leu Ala Ala Cys Gly Pro Pro Val Ala Pro Pro
        50                  55                  60

Ala Ala Val Ala Ala Val Ala Gly Gly Ala Arg Met Pro Cys Ala Glu
 65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys
               100                 105
```

<210> SEQ ID NO 30
<211> LENGTH: 88
<212> TYPE: PRT
<213> ORGANISM: Homo sapiens
<220> FEATURE:
<223> OTHER INFORMATION: IGFBP3

<400> SEQUENCE: 30

Met Gln Arg Ala Arg Pro Thr Leu Trp Ala Ala Ala Leu Thr Leu Leu
1               5                   10                  15

Val Leu Leu Arg Gly Pro Pro Val Ala Arg Ala Gly Ala Ser Ser Gly
            20                  25                  30

Gly Leu Gly Pro Val Val Arg Cys Glu Pro Cys Asp Ala Arg Ala Leu
        35                  40                  45

Ala Gln Cys Ala Pro Pro Pro Ala Val Cys Ala Glu Leu Val Arg Glu
    50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys
                85

<210> SEQ ID NO 31
<211> LENGTH: 74
<212> TYPE: PRT
<213> ORGANISM: Homo sapiens
<220> FEATURE:
<223> OTHER INFORMATION: IGFBP4

<400> SEQUENCE: 31

Met Leu Pro Leu Cys Leu Val Ala Ala Leu Leu Leu Ala Ala Gly Pro
1               5                   10                  15

Gly Pro Ser Leu Gly Asp Glu Ala Ile His Cys Pro Pro Cys Ser Glu
            20                  25                  30

Glu Lys Leu Ala Arg Cys Arg Pro Pro Val Gly Cys Glu Glu Leu Val
        35                  40                  45

Arg Glu Pro Gly Cys Gly Cys Cys Ala Thr Cys Ala Leu Gly Leu Gly
    50                  55                  60

Met Pro Cys Gly Val Tyr Thr Pro Arg Cys
65                  70

<210> SEQ ID NO 32
<211> LENGTH: 74
<212> TYPE: PRT
<213> ORGANISM: Homo sapiens
<220> FEATURE:
<223> OTHER INFORMATION: IGFBP5

<400> SEQUENCE: 32

Met Val Leu Leu Thr Ala Val Leu Leu Leu Ala Ala Tyr Ala Gly
1               5                   10                  15

Pro Ala Gln Ser Leu Gly Ser Phe Val His Cys Glu Pro Cys Asp Glu
            20                  25                  30

Lys Ala Leu Ser Met Cys Pro Pro Ser Pro Leu Gly Cys Glu Leu Val
        35                  40                  45

Lys Glu Pro Gly Cys Gly Cys Cys Met Thr Cys Ala Leu Ala Glu Gly
    50                  55                  60

Gln Ser Cys Gly Val Tyr Thr Glu Arg Cys
65                  70

<210> SEQ ID NO 33
<211> LENGTH: 77
<212> TYPE: PRT
<213> ORGANISM: Homo sapiens
<220> FEATURE:
<223> OTHER INFORMATION: IGFBP6

<400> SEQUENCE: 33

Met Thr Pro His Arg Leu Leu Pro Pro Leu Leu Leu Leu Leu Ala Leu
1               5                   10                  15

Leu Ala Ala Ser Pro Gly Gly Ala Leu Ala Arg Cys Pro Gly Cys Gly
            20                  25                  30

Gln Gly Val Gln Ala Gly Cys Pro Gly Gly Cys Val Glu Glu Glu Asp
        35                  40                  45

Gly Gly Ser Pro Ala Glu Gly Cys Ala Glu Ala Glu Gly Cys Leu Arg
    50                  55                  60

Arg Glu Gly Gln Glu Cys Gly Val Tyr Thr Pro Asn Cys
65                  70                  75

<210> SEQ ID NO 34
<211> LENGTH: 81
<212> TYPE: PRT
<213> ORGANISM: Homo sapiens
<220> FEATURE:
<223> OTHER INFORMATION: IGFBP7

<400> SEQUENCE: 34

Met Glu Arg Ala Ser Leu Arg Ala Leu Leu Phe Gly Pro Ala Gly Leu
1               5                   10                  15

Leu Leu Leu Leu Leu Pro Leu Ser Ser Ser Ser Ser Asp Thr Cys
            20                  25                  30

Gly Pro Cys Glu Pro Ala Ser Cys Pro Pro Leu Pro Pro Leu Gly Cys
        35                  40                  45

Leu Leu Gly Glu Thr Arg Asp Ala Cys Gly Cys Cys Pro Met Cys Ala
    50                  55                  60

Arg Gly Glu Gly Glu Pro Cys Gly Gly Gly Ala Gly Arg Gly Tyr
65                  70                  75                  80

Cys

<210> SEQ ID NO 35
<211> LENGTH: 101
<212> TYPE: PRT
<213> ORGANISM: Homo sapiens
<220> FEATURE:
<223> OTHER INFORMATION: C-hsi13412 and C-kaia397

<400> SEQUENCE: 35

Met Leu Pro Pro Arg Pro Ala Ala Ala Leu Ala Leu Pro Val Leu
1               5                   10                  15

Leu Leu Leu Leu Val Val Leu Thr Pro Pro Thr Gly Ala Arg Pro
            20                  25                  30

Ser Pro Gly Pro Asp Tyr Leu Arg Arg Gly Trp Met Arg Leu Leu Ala
        35                  40                  45

Glu Gly Glu Gly Cys Ala Pro Cys Arg Pro Glu Glu Cys Ala Ala Pro
    50                  55                  60

Arg Gly Cys Leu Ala Gly Arg Val Arg Asp Ala Gly Gly Cys Cys Trp
65                  70                  75                  80

-continued

```
Glu Cys Ala Asn Leu Glu Gly Gln Leu Cys Asp Leu Asp Pro Ser Ala
                85                  90                  95
His Tyr Gly His Cys
            100
```